US011071658B2

(12) United States Patent
Zink et al.

(10) Patent No.: US 11,071,658 B2
(45) Date of Patent: *Jul. 27, 2021

(54) ABSORBENT ARTICLES HAVING TEXTURE ZONES FORMING BACKGROUND PATTERNS AND MACRO PATTERNS

(71) Applicant: The Procter & Gamble Company, Cincinnati, OH (US)

(72) Inventors: Ronald Joseph Zink, Blue Ash, OH (US); Sarah Marie Wade, Springfield Township, OH (US); Tina Marie Glahn, West Chester, OH (US); Rachael Eden Walther, Union, KY (US); Gary Dean LaVon, Liberty Township, OH (US); Nicholas Paul Goyette, Cincinnati, OH (US); Kaoru Ishihara, West Chester, OH (US); Amanda Margaret Bicking, Cincinnati, OH (US); Diana Juratovac, Columbus, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 340 days.

This patent is subject to a terminal disclaimer.

(21) Appl. No.: 15/833,166

(22) Filed: Dec. 6, 2017

(65) Prior Publication Data
US 2018/0092785 A1 Apr. 5, 2018

Related U.S. Application Data

(63) Continuation of application No. 15/088,197, filed on Apr. 1, 2016, now Pat. No. 9,867,740, which is a
(Continued)

(51) Int. Cl.
*A61F 13/15* (2006.01)
*A61F 13/49* (2006.01)
(Continued)

(52) U.S. Cl.
CPC .. *A61F 13/49011* (2013.01); *A61F 13/15593* (2013.01); *A61F 13/15699* (2013.01);
(Continued)

(58) Field of Classification Search
CPC .. A61F 2013/49023; A61F 2013/49025; A61F 2013/49026; A61F 2013/49092;
(Continued)

(56) References Cited

U.S. PATENT DOCUMENTS 3,260,778 A 7/1966 Walton
4,041,203 A 8/1977 Brock
(Continued)

FOREIGN PATENT DOCUMENTS

CN 1382083 A 11/2002
EP 397110 B2 3/1990
(Continued)

OTHER PUBLICATIONS

ISR and Written Opinion, PCT/US2013/040886, dated Nov. 27, 2014.
(Continued)

Primary Examiner — Jacqueline F Stephens
(74) Attorney, Agent, or Firm — Christian M. Best

(57) ABSTRACT

An absorbent article comprises first and second substrates and one or more elastic elements disposed at least partially intermediate the substrates. The second substrate is attached to the first substrate and/or to portions of the elastic elements. The absorbent article comprises an adhesive having a first and second pattern of elements disposed on first substrate, and first and second texture zones. The first texture zone comprises a first portion of the substrates, a first portion of the elastic elements, and the first pattern of elements of the adhesive and forms a background pattern in the first portion of the substrates. The second texture zone comprises
(Continued)

a second portion of the substrates, a second portion of the one or more elastic elements, and the second pattern of elements of the adhesive and forms a macro pattern in the second portion of the substrates.

21 Claims, 41 Drawing Sheets

Related U.S. Application Data continuation of application No. 13/893,405, filed on May 14, 2013, now Pat. No. 9,326,899.

(60) Provisional application No. 61/647,061, filed on May 15, 2012, provisional application No. 61/647,071, filed on May 15, 2012, provisional application No. 61/647,078, filed on May 15, 2012.

(51) Int. Cl.
| | |
|---|---|
| *B32B 5/02* | (2006.01) |
| *B32B 5/26* | (2006.01) |
| *B32B 7/12* | (2006.01) |
| *B32B 3/08* | (2006.01) |
| *B32B 3/30* | (2006.01) |
| *A61F 13/514* | (2006.01) |
| *A61F 13/515* | (2006.01) |
| *A61F 13/64* | (2006.01) |
| *D06N 1/00* | (2006.01) |
| *A61F 13/56* | (2006.01) |
| *A61F 13/493* | (2006.01) |
| *A61F 13/72* | (2006.01) |
| *A61F 13/68* | (2006.01) |
| *A61F 13/51* | (2006.01) |
| *A61F 13/496* | (2006.01) |

(52) U.S. Cl.
CPC .... *A61F 13/15731* (2013.01); *A61F 13/4902* (2013.01); *A61F 13/493* (2013.01); *A61F 13/49019* (2013.01); *A61F 13/49058* (2013.01); *A61F 13/49061* (2013.01); *A61F 13/515* (2013.01); *A61F 13/51496* (2013.01); *A61F 13/5655* (2013.01); *A61F 13/64* (2013.01); *B32B 3/08* (2013.01); *B32B 3/30* (2013.01); *B32B 5/022* (2013.01); *B32B 5/26* (2013.01); *B32B 7/12* (2013.01); *D06N 1/00* (2013.01); *A61F 13/496* (2013.01); *A61F 13/565* (2013.01); *A61F 13/68* (2013.01); *A61F 13/72* (2013.01); *A61F 2013/49023* (2013.01); *A61F 2013/49025* (2013.01); *A61F 2013/49026* (2013.01); *A61F 2013/49092* (2013.01); *A61F 2013/51028* (2013.01); *B32B 2555/02* (2013.01); *Y10T 156/10* (2015.01); *Y10T 156/1039* (2015.01)

(58) Field of Classification Search
CPC ...... A61F 2013/51028; A61F 13/49011; A61F 13/15593; A61F 13/15699; A61F 13/15731; A61F 13/49019; A61F 13/4902; A61F 13/49058; A61F 13/49061; A61F 13/493; A61F 13/51496; A61F 13/515; A61F 13/64; B32B 3/08; B32B 3/30; B32B 5/022; B32B 5/26; B32B 7/12; B32B 2555/02; D06N 1/00; Y10T 156/10; Y10T 156/1039
See application file for complete search history.

(56) References Cited

U.S. PATENT DOCUMENTS

| | | | |
|---|---|---|---|
| 4,081,301 A | 3/1978 | Buell | |
| 4,090,385 A | 5/1978 | Packard | |
| 4,205,679 A | 6/1980 | Repke | |
| 4,284,454 A | 8/1981 | Joa | |
| 4,300,967 A | 11/1981 | Sigl | |
| 4,574,022 A | 3/1986 | Johnson | |
| 4,743,241 A | 5/1988 | Igaue | |
| 4,854,984 A | 8/1989 | Ball | |
| 4,977,011 A | 12/1990 | Smith | |
| 5,209,801 A | 5/1993 | Smith | |
| 5,344,516 A | 9/1994 | Tanji | |
| 5,415,649 A | 5/1995 | Watanabe | |
| 5,500,063 A | 3/1996 | Jessup | |
| 5,554,145 A | 9/1996 | Roe | |
| 5,576,090 A | 11/1996 | Suzuki | |
| 5,620,545 A | 4/1997 | Braun | |
| 5,622,581 A | 4/1997 | Ducker | |
| 5,626,574 A | 5/1997 | Sasaki | |
| 5,681,302 A | 10/1997 | Melbye | |
| 5,735,839 A | 4/1998 | Kawaguchi | |
| 5,827,253 A * | 10/1998 | Young | A61F 13/532 604/369 |
| 5,843,057 A | 12/1998 | McCormack | |
| 5,928,211 A | 2/1999 | Gustafsson | |
| 5,914,084 A | 6/1999 | Benson | |
| 6,027,593 A | 2/2000 | Lunt | |
| 6,096,668 A | 8/2000 | Abuto | |
| 6,291,039 B1 | 9/2001 | Combe | |
| 6,383,431 B1 | 5/2002 | Dobrin | |
| 6,458,447 B1 | 10/2002 | Cabell | |
| 6,537,644 B1 | 3/2003 | Kauschke | |
| 6,537,936 B1 | 3/2003 | Busam | |
| 6,547,774 B2 | 4/2003 | Ono et al. | |
| 6,902,793 B2 | 6/2005 | Ukegawa | |
| 7,029,545 B2 | 4/2006 | Suzuki | |
| 7,108,759 B2 | 9/2006 | You | |
| 7,112,193 B2 | 9/2006 | Otsubo | |
| 7,118,558 B2 | 10/2006 | Wu | |
| 7,255,688 B2 | 8/2007 | Sasaki | |
| 7,329,245 B2 | 2/2008 | Torigoshi | |
| 7,361,802 B2 | 4/2008 | Ishikawa | |
| 7,407,557 B2 | 8/2008 | Wada | |
| 7,449,015 B2 | 11/2008 | Otsubo | |
| 7,465,367 B2 | 12/2008 | Day | |
| 7,530,972 B2 | 5/2009 | Ando | |
| 7,534,928 B2 | 5/2009 | Sakamoto et al. | |
| 7,621,900 B2 | 11/2009 | Van Gompel | |
| 7,642,398 B2 | 1/2010 | Järpenberg et al. | |
| 7,682,686 B2 | 3/2010 | Curro | |
| 7,754,627 B2 | 7/2010 | Mukai | |
| 7,763,339 B2 | 7/2010 | Groitzsch | |
| 7,766,887 B2 | 8/2010 | Burns, Jr. et al. | |
| 7,895,718 B2 | 3/2011 | Horn | |
| 8,388,596 B2 | 3/2013 | Horn | |
| 8,450,556 B2 | 5/2013 | Miyamoto et al. | |
| 8,574,211 B2 | 11/2013 | Morita | |
| 8,597,268 B2 | 12/2013 | Sauer | |
| 8,647,319 B2 | 2/2014 | Een | |
| 9,011,404 B2 | 4/2015 | Kobayashi et al. | |
| 9,216,116 B2 | 12/2015 | Roe | |
| D748,932 S | 2/2016 | Puricelli | |
| 9,301,881 B2 | 4/2016 | Ando et al. | |
| 9,326,899 B2 | 5/2016 | Zink et al. | |
| 9,333,119 B2 | 5/2016 | Zink et al. | |
| 9,375,361 B2 | 6/2016 | Zink et al. | |
| 9,510,979 B2 | 12/2016 | Trennepohl | |
| 9,603,750 B2 | 3/2017 | Van De Maele | |
| 9,867,740 B2 | 1/2018 | Zink et al. | |
| 10,575,996 B2 | 3/2020 | Zink et al. | |
| 10,575,997 B2 | 3/2020 | Zink et al. | |
| 2004/0015146 A1 | 1/2004 | Torigoshi et al. | |
| 2004/0102757 A1 | 5/2004 | Olson | |
| 2004/0154767 A1 | 8/2004 | Trokhan | |
| 2004/0243083 A1 | 12/2004 | Matsuda | |
| 2005/0004549 A1 | 1/2005 | Maas et al. | |

(56) References Cited

U.S. PATENT DOCUMENTS

| | | |
|---|---|---|
| 2005/0203479 A1 | 3/2005 | Sakaguchi |
| 2006/0069361 A1 | 3/2006 | Olson |
| 2006/0142728 A1 | 6/2006 | Tabor et al. |
| 2006/0173436 A1 | 8/2006 | Krautkramer |
| 2006/0270302 A1 | 11/2006 | Ando et al. |
| 2007/0249253 A1 | 10/2007 | Angeli |
| 2008/0009817 A1 | 1/2008 | Norrby |
| 2008/0124996 A1 | 5/2008 | Hashimoto |
| 2009/0035527 A1 | 2/2009 | Kobayashi |
| 2009/0061185 A1 | 3/2009 | Hisamoto |
| 2009/0157035 A1 | 6/2009 | Ponomarenko |
| 2009/0157036 A1 | 6/2009 | Ponomarenko et al. |
| 2009/0191779 A1 | 7/2009 | Cree |
| 2009/0275909 A1 | 11/2009 | Sakaguchi |
| 2009/0308524 A1 | 12/2009 | Gunji |
| 2009/0326499 A1 | 12/2009 | Veith |
| 2010/0028638 A1 | 2/2010 | Reichardt et al. |
| 2010/0076394 A1 | 3/2010 | Hayase |
| 2010/0234823 A1 | 9/2010 | Morita |
| 2010/0286646 A1 | 11/2010 | Takino et al. |
| 2011/0106039 A1 | 5/2011 | Saito et al. |
| 2011/0118689 A1 | 5/2011 | Een et al. |
| 2011/0144610 A1 | 6/2011 | Kalson et al. |
| 2011/0213325 A1 | 9/2011 | Gabrielli et al. |
| 2011/0251576 A1 | 10/2011 | Ando et al. |
| 2012/0041407 A1 | 2/2012 | Kamiyama et al. |
| 2012/0238989 A1 | 9/2012 | Tomomi et al. |
| 2012/0251771 A1 | 10/2012 | Wilson |
| 2013/0261589 A1 | 10/2013 | Fujkawa |
| 2013/0306226 A1 | 11/2013 | Zink et al. |
| 2016/0058624 A1 | 3/2016 | Hohm |
| 2016/0220425 A1 | 8/2016 | Zink et al. |
| 2016/0220426 A1 | 8/2016 | Zink et al. |
| 2016/0235599 A1 | 8/2016 | Zink et al. |
| 2020/0155367 A1 | 5/2020 | Zink et al. |
| 2020/0155368 A1 | 5/2020 | Zink et al. |
| 2020/0261283 A1 | 8/2020 | Zink et al. |

FOREIGN PATENT DOCUMENTS

| | | |
|---|---|---|
| EP | 1102571 B1 | 8/1998 |
| EP | 1179330 | 8/2000 |
| EP | 1184012 | 9/2000 |
| EP | 1269955 B1 | 6/2001 |
| JP | 2006-122456 | 5/2006 |
| JP | 2008/173286 | 7/2008 |
| JP | 2008148834 A | 7/2008 |
| JP | 2009034547 A | 2/2009 |
| JP | 2009153841 A | 7/2009 |
| JP | 2009-240694 | 10/2009 |
| JP | 2010284229 A | 12/2010 |
| JP | 2011010839 A | 1/2011 |
| JP | 2011036538 A | 2/2011 |
| JP | 2011062257 A | 3/2011 |
| JP | 2011224046 A | 11/2011 |
| WO | WO2000037003 A2 | 11/1999 |
| WO | 03082168 A1 | 10/2003 |
| WO | WO2009067055 A1 | 11/2007 |
| WO | WO-20100113470 | 7/2010 |

OTHER PUBLICATIONS

All Offices Actions, Responses and Claims for U.S. Appl. No. 13/893,405.
All Offices Actions, Responses and Claims for U.S. Appl. No. 13/893,735.
All Offices Actions, Responses and Claims for U.S. Appl. No. 13/893,634.
All Offices Actions, Responses and Claims for U.S. Appl. No. 13/893,658.
All Offices Actions, Responses and Claims for U.S. Appl. No. 15/088,207.
All Offices Actions, Responses and Claims for U.S. Appl. No. 15/137,041.
All Offices Actions, Responses and Claims for U.S. Appl. No. 15/088,197.
All Offices Actions, Responses and Claims for U.S. Appl. No. 16/751,358.
All Offices Actions, Responses and Claims for U.S. Appl. No. 16/751,228.
All Offices Actions, Responses and Claims for U.S. Appl. No. 16/868,944.

* cited by examiner

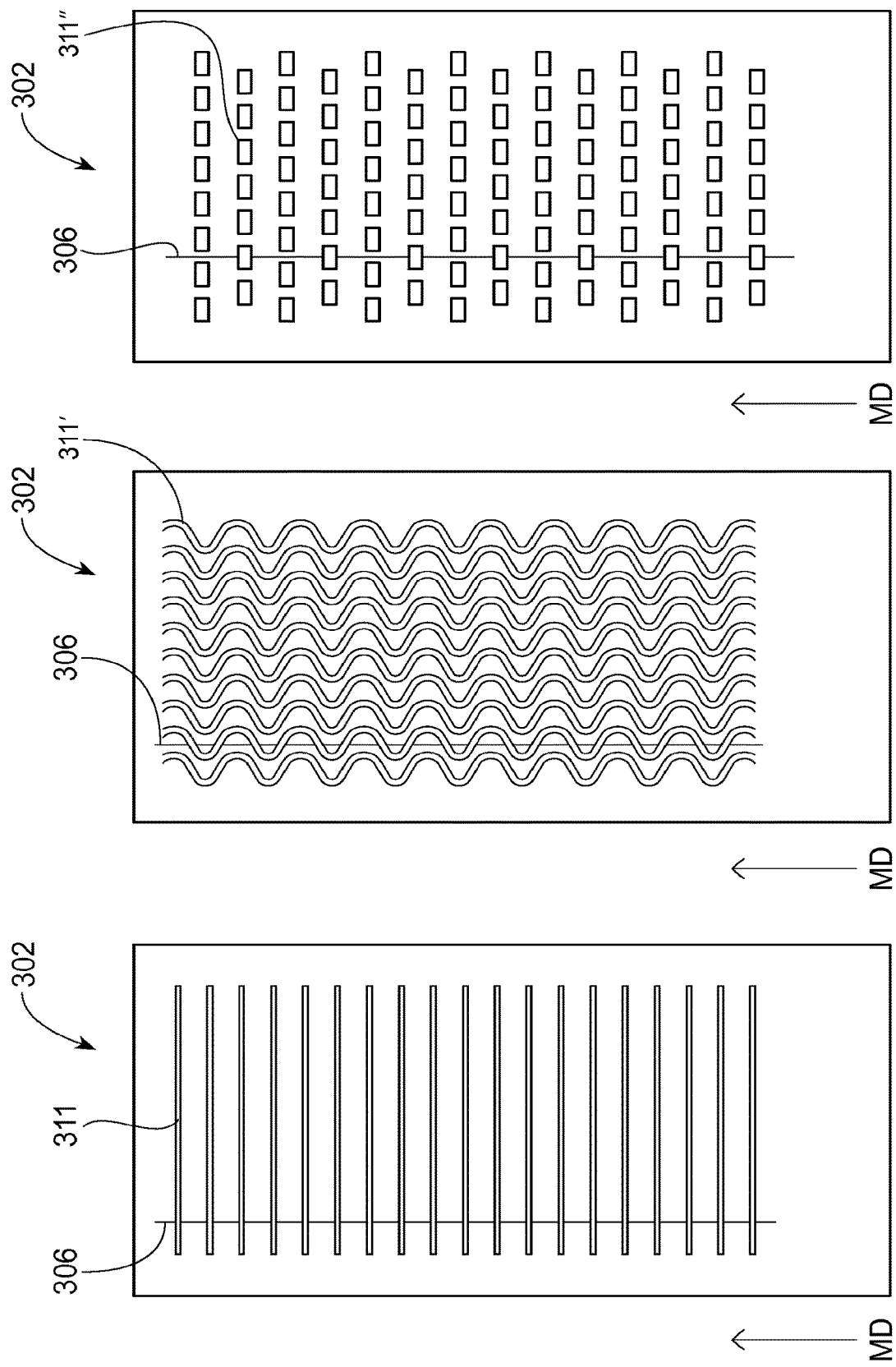

ABSORBENT ARTICLES HAVING TEXTURE ZONES FORMING BACKGROUND PATTERNS AND MACRO PATTERNS

CROSS REFERENCE TO RELATED APPLICATIONS

This application is a continuation of, and claims priority under 35 U.S.C. § 120 to, U.S. patent application Ser. No. 15/088,197, filed on Apr. 1, 2016, which is a continuation of, and claims priority under 35 U.S.C. § 120 to, U.S. patent application Ser. No. 13/893,405, filed on May 14, 2013, now U.S. Pat. No. 9,326,899, granted on May 3, 2016, which claims the benefit, under 35 U.S.C. § 119(e), of U.S. Provisional Patent Application Nos. 61/647,061, 61/647,071, and 61/647,078, all filed on May 15, 2012. All of the above-referenced patent applications are hereby incorporated by reference herein in their entirety.

FIELD

The present disclosure generally relates to absorbent articles having texture zones forming patterns, and more particularly, relates to absorbent articles having texture zones forming background patterns and macro patterns.

BACKGROUND

Infants, children, and other incontinent individuals wear disposable absorbent articles, such as diapers, to receive and contain urine and other body exudates. Tape diapers are popular for infants and young children, while training pants or pull-on diapers have become popular for use on older children (e.g., 3-5 year olds) or other incontinent individuals able to walk and often who are toilet training. Various disposable absorbent articles comprise some type of texture or printed graphics on a portion of a garment-facing surface or backsheet or a wearer-facing surface or topsheet thereof for aesthetic purposes. The textures are usually irregular and generally do not provide an aesthetically pleasing appearance, fit, and comfortable feel. Furthermore, these textures typically appear throughout a garment-facing surface or backsheet or a wearer-facing surface or topsheet of the absorbent articles. Additionally, usually only one texture is provided by using additional material(s). It would be desirable to provide absorbent articles that provide an improved fit and comfortable feel, have an aesthetically pleasing appearance, and more closely resemble clothing or underwear without adding cost, or significant cost, to absorbent article manufacturing.

SUMMARY

In one form, the present disclosure is directed, in part, to an absorbent article comprising a chassis comprising a topsheet, a backsheet, and a core disposed intermediate the topsheet and the backsheet. The absorbent article comprises a belt portion extending from the chassis. The belt portion comprises a first substrate, a second substrate, and one or more elastic elements disposed at least partially intermediate the first substrate and the second substrate. Portions of the elastic elements are joined to the first substrate and the second substrate is joined to the first substrate and/or to portions of the elastic elements. The absorbent article comprises a first texture zone comprising a plurality of rugosities formed in the first substrate. The plurality of the rugosities have a first frequency range. The first texture zone forms a background pattern in the belt portion. The absorbent article comprises a second texture zone comprising a plurality of rugosities formed in the first substrate. The plurality of the rugosities have a second, different frequency range. The second texture zone forms a macro pattern in the belt portion.

In another form, the present disclosure is directed, in part, to an absorbent article comprising a core, a first substrate, a second substrate, and one or more elastic elements disposed at least partially intermediate the first substrate and the second substrate. The second substrate is attached to the first substrate and/or portions of one or more of the elastic elements. The absorbent article comprises an adhesive having a first pattern of elements and a second pattern of elements disposed on first substrate and/or on portions of the elastic elements, a first texture zone, and a second texture zone. The first texture zone comprises a first portion of the substrates, a first portion of the one or more elastic elements, and the first pattern of elements of the adhesive. The first texture zone forms a background pattern in the first portion of the substrates. The second texture zone comprising a second portion of the substrates, a second portion of the one or more elastic elements, and the second pattern of elements of the adhesive. The second texture zone forms a macro pattern in the second portion of the substrates.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIGS. 22A-22F are example adhesive patterns on a substrate and/or on portions of elastic elements in accordance with various non-limiting embodiments;

DETAILED DESCRIPTION

Figure 1:
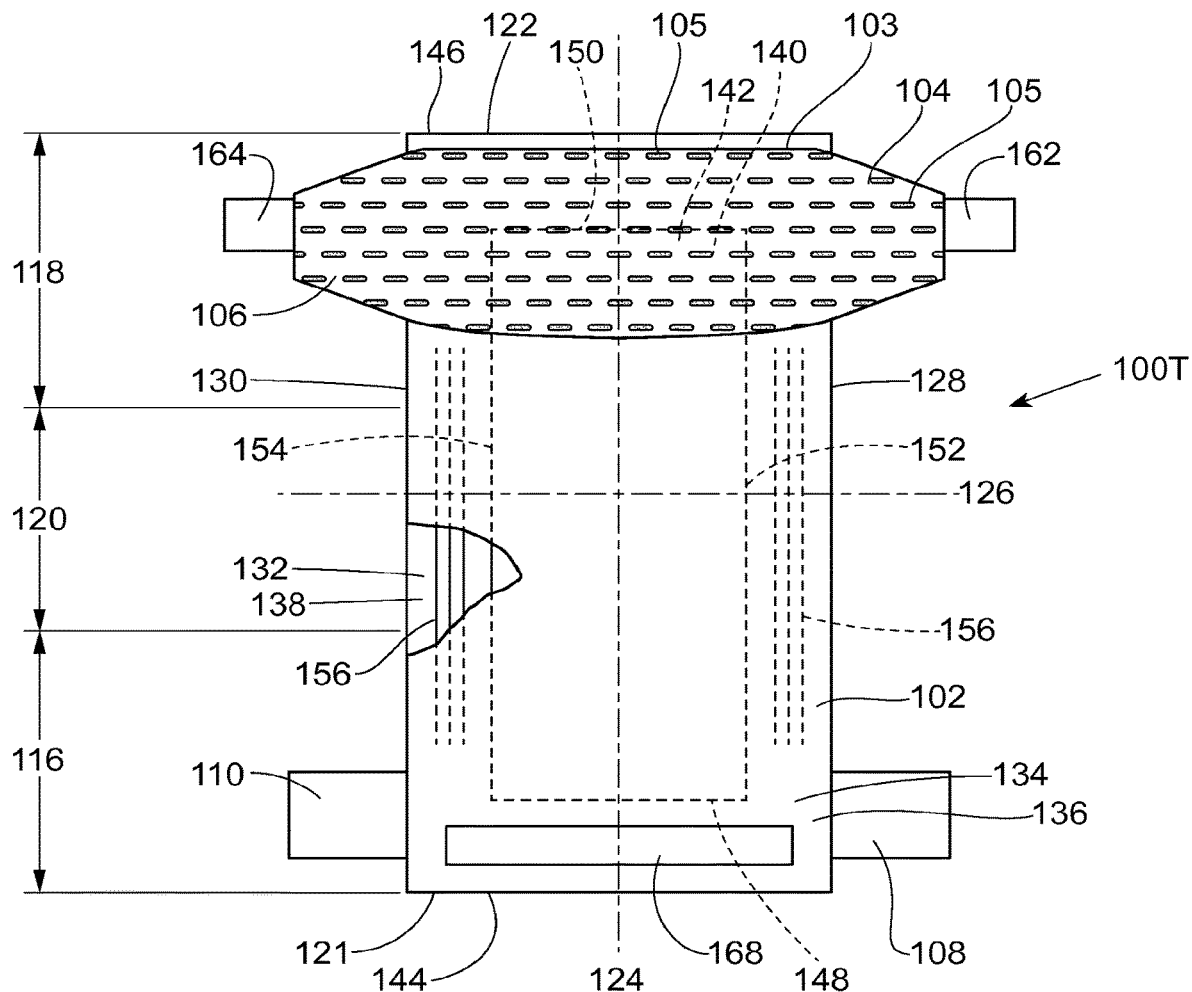
FIG. 1 is a partially cut away plan view of a taped diaper with the garment-facing surface oriented towards the viewer in accordance with one non-limiting embodiment.

Various non-limiting embodiments of the present disclosure will now be described to provide an overall understanding of the principles of the structure, function, manufacture, and use of the absorbent articles having texture zones forming background and macro patterns and methods for making the same disclosed herein. One or more examples of these non-limiting embodiments are illustrated in the accompanying drawings. Those of ordinary skill in the art will understand that the absorbent articles having texture zones forming background and macro patterns and methods for making the same described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

The following term explanations may be useful in understanding the present disclosure:

"Absorbent article(s)" is used herein to refer to consumer products whose primary function is to absorb and retain soils and wastes. Absorbent articles may refer to pants and/or taped diapers. The terms "diaper" and "pants" are used herein to refer to absorbent articles generally worn by infants, children, and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "elastic element" is used herein to refer to materials exhibiting elastic properties, which include any material that upon application of a force when in its relaxed, initial length may stretch or elongate to an elongated length equal to or greater than 10% more than its initial length and will substantially recover back to about its initial length upon release of the applied force.

The terms "joined," "attached," or "engaged with" encompass configurations wherein an element is directly secured to another element by affixing the element directly to the other element, and configurations wherein an element is indirectly secured to another element by affixing the element to intermediate member(s) which in turn are affixed to the other element.

The term "longitudinal" is used herein to refer to a direction running substantially perpendicular from a first waist opening edge to a longitudinally opposing second waist opening edge of an absorbent article when the absorbent article is in a flat out, uncontracted state, or from a waist opening edge to the bottom of the crotch region (i.e., the fold line, in a bi-folded absorbent article). Directions within 45 degrees of the longitudinal direction are considered to be "longitudinal."

The term "lateral" is used herein to refer to a direction running from a first longitudinally extending side edge to a laterally opposing longitudinally extending second side edge of an absorbent article and generally at a right angle to the longitudinal direction. Directions within 45 degrees of the lateral direction are considered to be "lateral."

The term "substrate" is used herein to describe a material which is primarily two-dimensional (i.e., in an XY plane) and whose thickness (in a Z direction) is relatively small (i.e. 1/10 or less) in comparison to its length (in an X direction) and width (in a Y direction). Non-limiting examples of substrates comprise a web, layer or layers or fibrous materials, nonwovens, films and foils, such as polymeric films or metallic foils, for example. These materials may be used alone or may comprise two or more layers laminated together. As such, a web is a substrate.

The terms "nonwoven" or "nonwoven material" are used herein to refer to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" is used herein to refer to disposable absorbent articles having an initial front or first waist region and an initial back or second waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" (also referred to herein as "diaper pants" or "pant diapers") is used herein to refer to disposable absorbent articles having a continuous perimeter waist opening and continuous perimeter leg openings designed for infant or adult wearers. A pant may be configured with a continuous or closed waist opening and at least one continuous, closed, leg opening prior to the absorbent article being applied to the wearer. A pant may be preformed by various techniques including, but not limited to, joining together portions of the article using any refastenable and/or permanent closure member (e.g., seams, heat bonds, pressure welds, adhesives, cohesive bonds, mechanical fasteners, etc.). A pant may be preformed anywhere along the circumference of the absorbent article in the waist region (e.g., side fastened or seamed, front waist fastened or seamed, rear waist fastened or seamed). A pant may be opened about one or both of the side seams and then refastened. Example diaper pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

The term "initial waist opening circumference" is used herein to refer to the circumference of the waist opening at the time the pant is placed in the package and subsequently when it is removed from the package by the consumer.

The term "texture zone" or "elasticized texture zone" is used herein to refer to an elasticized region of the absorbent article comprising a plurality of rugosities which may be described by a range of frequencies, amplitudes, and/or surface geometries in one or both of the machine direction and the cross direction in its relaxed state. In an elongated state, the frequencies of the rugosities of a texture zone may decrease proportionally to the induced elongation. Each texture zone may comprise at least one substrate and at least one elastic element. In certain instances, a texture zone may comprise two substrates and a plurality of elastic elements.

The term "background pattern" as used herein refers to a texture zone that forms a backdrop or base pattern in a portion of an absorbent article. The background pattern may surround, or at least partially surround, a texture zone forming a macro pattern in the portion of the absorbent article. The background pattern may be thought of as the secondary pattern in the portion of the absorbent article.

The term "macro pattern" as used herein refers to a texture zone that forms main portions or elements of a pattern in an absorbent article and that is surrounded by, or at least partially surrounded by, the background pattern.

The term "rugosity" or "rugosities" as used herein may mean ridges, wrinkles, and/or creases formed in a substrate proximate to elastic elements attached to or otherwise engaged with the substrate when the elastic elements are in a relaxed state or a partially relaxed state. Each rugosity has a minimum amplitude of 0.25 mm.

Various substrates may be used to construct various components of the absorbent articles, such as backsheets, topsheets, belt portions, and absorbent cores. Example descriptions of absorbent article components with respect to both taped diapers and pant diapers are provided below.

Figure 1A:
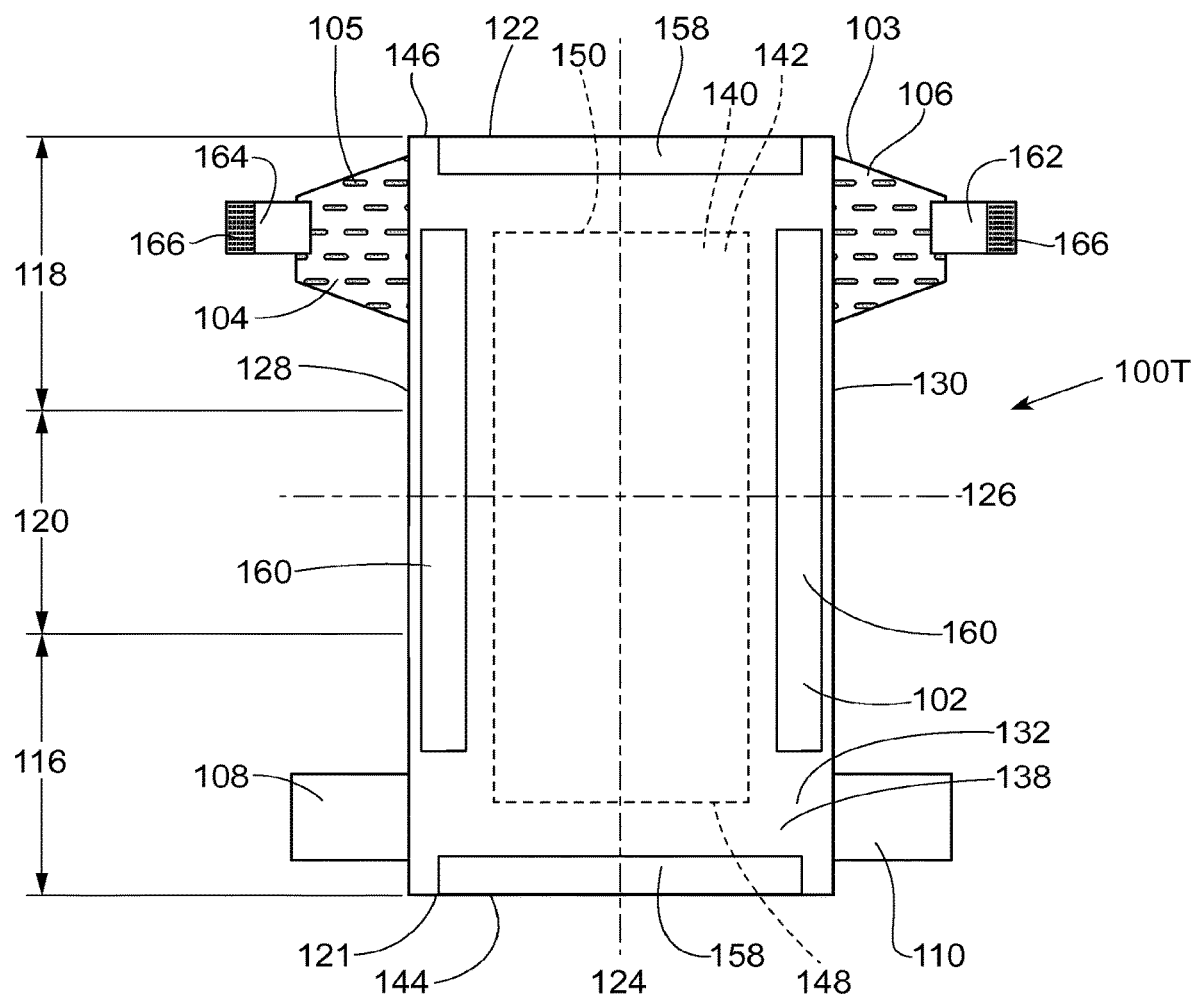
FIG. 1A is a plan view of the taped diaper of FIG. 1 with the wearer-facing surface oriented towards the viewer in accordance with one non-limiting embodiment.
Figure 2:
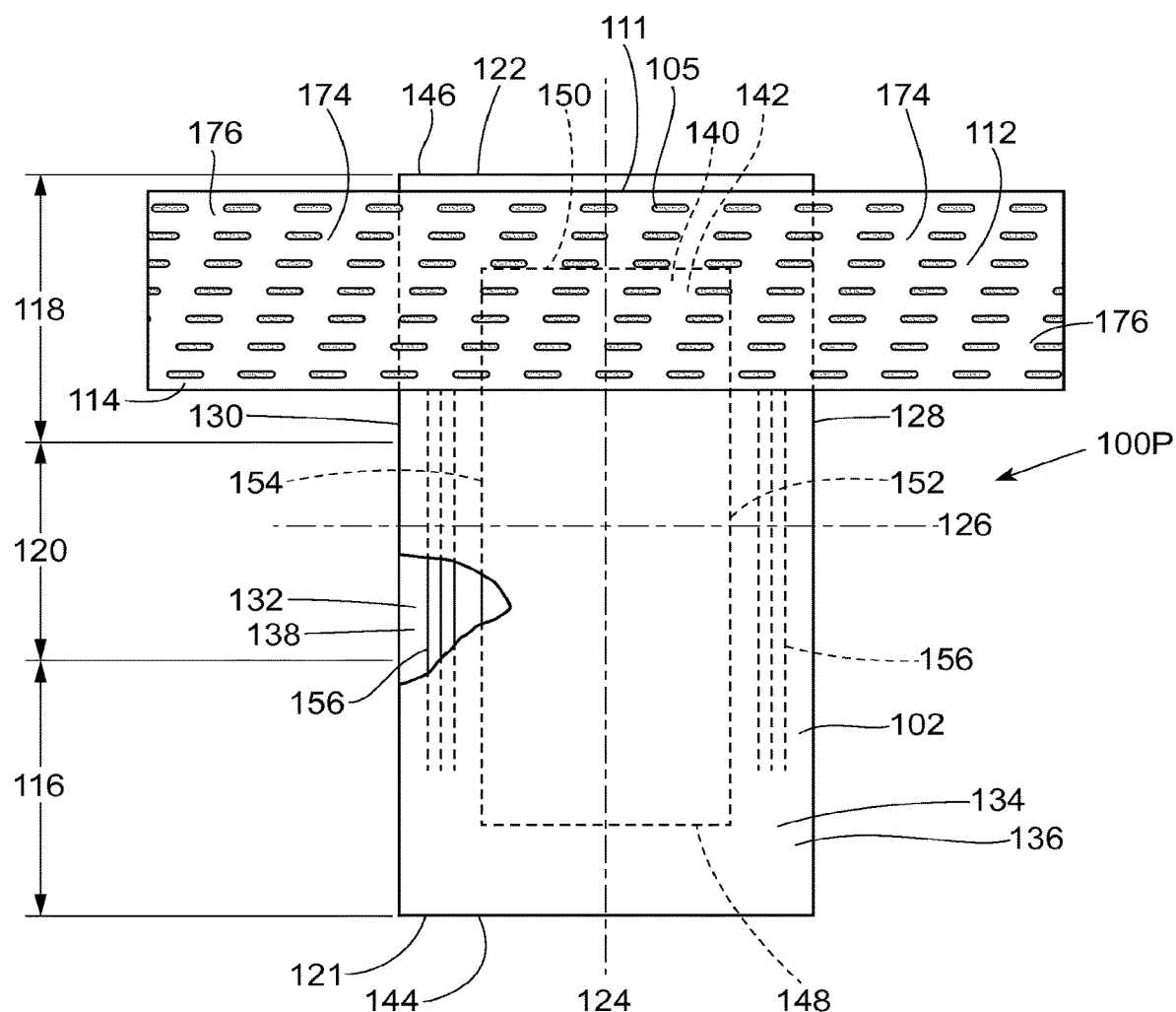
FIG. 2 is a partially cut away plan view of a pant diaper with a belt portion extending from a first end portion of a chassis thereof in accordance with one non-limiting embodiment.
Figure 3:
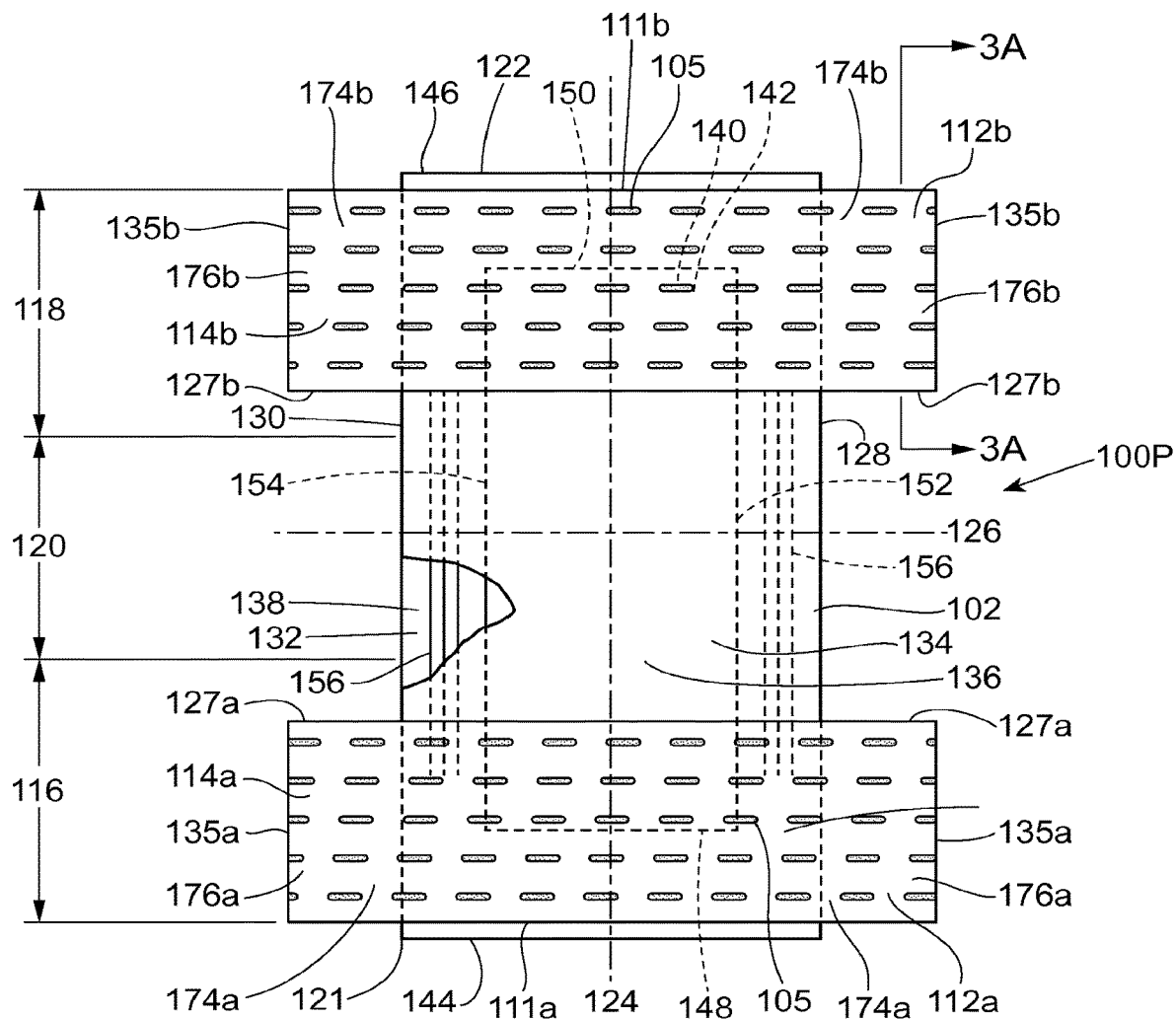
FIG. 3 is a partially cut away plan view of a pant diaper with a first belt portion extending from a first end portion of a chassis and a second belt portion extending from a second end portion of the chassis in accordance with one non-limiting embodiment.

The following provides a general description of various types of taped diapers and pant diapers. FIG. 1 shows one example of a plan view of a taped diaper 100T, with the garment-facing surface oriented towards the viewer. FIG. 1A shows a plan view of the taped diaper 100T with the wearer-facing surface oriented towards the viewer. The taped diaper 100T shown in FIGS. 1 and 1A may comprise a chassis 102, a belt portion 103 comprising first and second back ears 104 and 106, and first and second front ears 108 and 110. The first and second back ears 104 and 106 may be integrally formed with the belt portion 103. The belt portion 103 may comprise one or more elastic elements or elastic stands 105 therein. Although not illustrated, the front ears 108 and 110 may be formed from a second belt portion comprising elastic elements or strands. FIG. 2 shows a plan view of a diaper pant 100P in a flat, unfolded condition, with the garment-facing surface oriented towards the viewer. The pant diaper 100P shown in FIG. 2 also comprises a chassis 102 and a belt portion 111 comprising or forming first and second belt ears 112 and 114. The belt portion 111 may also comprise elastic elements or elastic strands 105 positioned therein. FIG. 3 shows a diaper pant 100P and chassis 102 in a flat, unfolded condition, with the garment-facing surface oriented towards the viewer. However, the diaper pant 100P of FIG. 3 comprises first and second rear belt ears 112*b* and 114*b* formed in a second belt portion 111*b*, and first and second front belt ears 112a and 114a formed in a first belt portion 111a. In various embodiments, the belt portions 111b and 111a may extend from the chassis 102 in both the lateral and longitudinal directions, may be joined to the chassis 102 either on the wearer-facing surface or garment-facing surface thereof, or may be formed integrally with one or more of the materials used to form a portion of the chassis 102.

Although pant and taped diapers may have distinctly different features and components, it is to be appreciated that taped and pant diapers may comprise many features and components that are the same, substantially the same, or similar with regard to disposition, structure, dimension, physical appearance, etc. For the purposes of a specific illustration, various common components of taped and pant diapers shown in FIGS. 1-6 are described below before discussing different features and/or components between the taped and pant diapers.

As shown in FIGS. 1-3, the diapers 100T and 100P are shown as having a first waist region 116, a second waist region 118, and a crotch region 120 disposed intermediate the first and second waist regions 116 and 118. The first waist region 116 may be configured as a front waist region, and the second waist region 118 may be configured as back waist region. In some embodiments, the length of each of the front waist region 116, the back waist region 118, and the crotch region 120 may be ⅓ of the length of the absorbent article 100P and 100T. The absorbent articles 100P and 100T, particularly the belt portions, may each comprise a laterally extending front waist opening edge 121 in the front waist region 116 and a longitudinally opposing and laterally extending back waist opening edge 122 in the back waist region 118. In an embodiment, the front waist opening edge 121 and the back waist opening edge 122 may be formed by edges of the longitudinally spaced belt portions. To provide a frame of reference for the present discussion, the diapers 100T and 100P in FIGS. 1-3 are shown with a longitudinal axis 124 and a lateral axis 126. The longitudinal axis 124 may extend through a midpoint of the front waist opening edge 121 and through a midpoint of the back waist opening edge 122. The lateral axis 126 may extend through a midpoint of a first longitudinal or right side edge 128 and through a midpoint of a second longitudinal or left side edge 130.

As shown in FIGS. 1-3, the absorbent articles 100T and 100P may each comprise an inner, wearer-facing surface 132, and an outer, garment-facing surface 134. The chassis 102 may comprise a backsheet 136 and a topsheet 138. An absorbent assembly 140 including an absorbent core 142 may be disposed intermediate a portion of the topsheet 138 and a portion of the backsheet 136. The chassis 102 may comprise a first end portion in the first waist region 116 and a second end portion in the second waist region 118. The one or more belt portions may extend from, be attached to, be joined to, or be formed with one or both of the first end portion and the second end portion of the chassis 102 depending on a particular desired configuration of an absorbent article.

As discussed in more detail below, the diapers 100T and 100P may also comprise other features, such as leg elastics, an elastic or extensible waist region, and/or flaps (e.g., belt ears) to enhance the fit around the legs and waist of the wearer. Referring specifically to FIG. 3, as an example, the first waist region 116 of the chassis 102 may form a portion of the front waist opening edge 121 and/or the second waist region 118 of the chassis 102 may form a portion of the back waist opening edge 122. Alternatively, the belt portion 111a may form a portion of, or all of, the front waist opening edge 121 and/or the belt portion 111b may form a portion of, or all of, the back waist opening edge 122. Those of skill in the art will understand that this may depend on the placement of the belt portions 111a and 111b on the chassis 102. The belt portion 111a may comprise first and second leg opening edges 127a and the belt portion 111b may comprise first and second leg opening edges 127b. The belt portion 111a may comprise side edges 135a and the belt portion 111b may comprise side edges 135b.

Figure 3A:
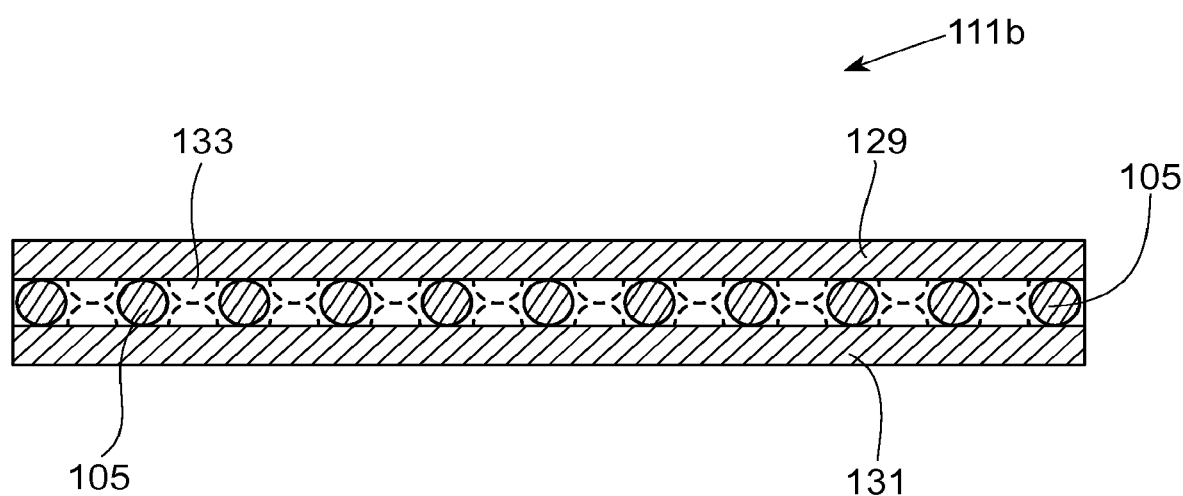
FIG. 3A is an example cross-sectional view of the first belt portion taken about line 3A-3A of FIG. 3 in accordance with one non-limiting embodiment.

In an embodiment, referring to FIG. 3A, which is an example cross-sectional view taken about line 3A-3A of FIG. 3, each belt portion 111a or 111b may comprise a first substrate 129 and a second substrate 131. The first substrate 129 may be attached to the second substrate 131. In an embodiment, one or more elastic elements or elastic strands 105 may be positioned or disposed intermediate the first substrate 129 and the second substrate 131. The first substrate 129 may be attached to the second substrate 131 by one or more of the elastic elements or elastic strands 105. In other words, one or both of the substrates 129 and 131 may be attached, or adhesively attached, to one or more of the elastic elements 105. In other embodiments, only one of the first and second substrates 129 and 131 may be attached to the elastic elements 105 and the first substrate 129 may be bonded to, joined to, attached to, or adhesively attached to the second substrate 131 (see e.g., bonds 133 in dash). In an embodiment, the first and second substrates 129 and 131 may comprise woven or nonwoven materials or various types of films as described in further detail herein.

In an embodiment, referring to FIGS. 1-3, the periphery of the chassis 102 may be defined by the first longitudinal side edge 128, the second longitudinal side edge 130, a first laterally extending end edge 144 disposed in the first waist region 116, and a second laterally extending end edge 146 disposed in the second waist region 118. Alternatively, the first laterally extending end edge 144 disposed in the first waist region 116 and the second laterally extending end edge 146 disposed in the second waist region 118 may be overlapped by the belt portions 111a and 111b. Both side edges 128 and 130 extend longitudinally at least partially between the front waist edge 121 and the back waist edge 122. The laterally extending end edges 144 and 146 of the chassis 102 may form a portion of the laterally extending front waist edge 121 in the front waist region 116 and a portion of the longitudinally opposing and laterally extending back waist edge 122 in the back waist region 118, unless overlapped by the belt portions. When either the taped diaper 100T or the pant diaper 100P is worn on a lower torso of a wearer, the front waist edge 121 and the back waist edge 122 may encircle a portion of the waist of the wearer. At the same time, the chassis side edges 128 and 130 and the leg opening edges 127a and 127b (see FIG. 3) may encircle a portion of the legs of the wearer. The crotch region 120 may be generally positioned between the legs of the wearer with the absorbent core 142 extending from the front waist region 116 through the crotch region 120 to the back waist region 118.

As previously mentioned, the taped and pant diapers 100T and 100P may comprise a backsheet 136. The backsheet 136 may define the outer surface or garment-facing surface 134 of the chassis 102. The backsheet 136 may be impervious, or substantially impervious, to fluids (e.g., menses, urine, and/or runny feces) and may be manufactured from a thin plastic film, although other flexible liquid impervious materials may also be used. The backsheet 136 may prevent, or at least inhibit, the exudates absorbed and contained in the absorbent core 142 from wetting articles which contact the diapers 100T and 100P, such as bedsheets, pajamas, and undergarments, for example. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet 136 may also comprise an elastomeric film. An example backsheet 136 may be a polyethylene film having a thickness of from about 0.012 mm (0.5 mils) to about 0.051 mm (2.0 mils). Example polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more cloth-like appearance. Further, the backsheet 136 may permit vapors to escape from the absorbent core 142 (i.e., the backsheet is breathable) while still preventing, or at least inhibiting, exudates from passing through the backsheet 136. The size of the backsheet 136 may be dictated by the size of the absorbent core 142 and/or particular configuration or size of the diapers 100T and 100P.

As also described above, the taped and pant diapers 100T and 100P may comprise a topsheet 138. The topsheet 138 may define all or part of the inner surface or wearer-facing surface 132 of the chassis 102. The topsheet 138 may be compliant, soft feeling, and/or non-irritating to the wearer's skin. It may be elastically stretchable in one or two directions. Further, the topsheet 138 may be liquid pervious, permitting liquids (e.g., menses, urine, and/or runny feces) to penetrate through its thickness. A suitable topsheet 138 may be manufactured from a wide range of materials such as woven and nonwoven materials, apertured or hydroformed thermoplastic films, apertured nonwovens, porous foams, reticulated foams, reticulated thermoplastic films, and thermoplastic scrims. Suitable woven and nonwoven materials may comprise natural fibers such as wood or cotton fibers, synthetic fibers such as polyester, polypropylene, or polyethylene fibers, or combinations thereof. If the topsheet 138 comprises fibers, the fibers may be spunbond, carded, wet-laid, meltblown, hydroentangled, or otherwise processed as is generally known in the art.

Topsheets 138 may be selected from high loft nonwoven topsheets, apertured film topsheets and apertured nonwoven topsheets. Apertured film topsheets may be pervious to bodily exudates, yet non-absorbent, and have a reduced tendency to allow fluids to pass back through and rewet the wearer's skin. Example apertured films may comprise those described in U.S. Pat. Nos. 5,628,097, 5,916,661, 6,545,197, and 6,107,539.

As mentioned above, the taped and pant diapers 100P and 100T may also comprise an absorbent assembly 140 that is joined to the chassis 102. As shown in FIGS. 1-3, the absorbent assembly 140 may comprise a laterally extending front edge 148 in the front waist region 116 and may have a longitudinally opposing and laterally extending back edge 150 in the back waist region 118. The absorbent assembly 140 may comprise a longitudinally extending right side edge 152 and a laterally opposing and longitudinally extending left side edge 154. Both absorbent assembly side edges 152 and 154 may extend longitudinally between the front edge 148 and the back edge 150. The absorbent assembly 140 may additionally comprise one or more absorbent cores 142 or absorbent core layers. Each of the one or more absorbent cores 142 or absorbent core layers may be at least partially disposed between the topsheet 138 and the backsheet 136 and may be formed in various sizes and shapes that are compatible with the diapers 100T and 100P. Example absorbent structures for use as the absorbent core of the present disclosure are described in U.S. Pat. Nos. 4,610,678, 4,673, 402, 4,888,231, and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such an absorbent core may comprise primarily absorbent gelling material (AGM) in amounts of at least about 60%, 70%, 80%, 85%, 90%, 95%, or even about 100%, where the remainder of the absorbent core comprises a microfiber glue (if applicable). Such cores, microfiber glues, and absorbent gelling materials are described in U.S. Pat. Nos. 5,599,335, 5,562,646, 5,669,894, 6,790,798, and 7,521,587, as well as U.S. Patent Publication No. 2004/0158212.

As previously mentioned, the taped diapers 100T and pant diapers 100P may also comprise elasticized leg cuffs 156 on the chassis 102. It is to be appreciated that the leg cuffs 156 may be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may comprise those described in U.S. Pat. Nos. 3,860,003, 4,909,803, 4,695,278, 4,795,454, 4,704,115, 4,909,803, 7,931,636, and U.S. Patent Publication No. 2009/0312730A1.

As shown in FIG. 1A, the chassis 102 may have longitudinally extending and laterally opposing side flaps 160 that are disposed on the interior surface or wearer-facing surface 132 of the chassis 102. Each of the side flaps 160 may have a proximal edge. The side flaps 160 may also overlap the absorbent assembly 140 (i.e., the proximal edges extend laterally inward of the respective side edges of the absorbent assembly 152 and 154). In some configurations, the side flaps 160 may not overlap the absorbent assembly 140. It is to be appreciated that the side flaps 160 may be formed in various ways, such as for example, by folding portions of the chassis 102 laterally inward (i.e., toward the longitudinal axis 124) to form both the respective side flaps 160 and the side edges 128 and 130 of the chassis 102. In another example, the side flaps 160 may be formed by attaching an additional layer or layers to the chassis 102 at or adjacent to each of the respective side edges and of the chassis 102. Each of the side flaps 160 may be joined to the wearer-facing surface 132 of the chassis 102 and/or the absorbent assembly 140 in side flap attachment zones in the front waist region 116 and in side flap attachment zones in the back waist region 118. The side flaps 160 may extend to the same longitudinal extent as the absorbent article or alternatively the side flaps 160 may have a longitudinal extent that is less than the absorbent article.

As previously mentioned, pant and taped diapers 100T and 100P may have distinct different features and/or components. The following provides a general discussion of some such features and components with reference to accompanying figures showing embodiments of taped and pant diapers.

Figure 4:
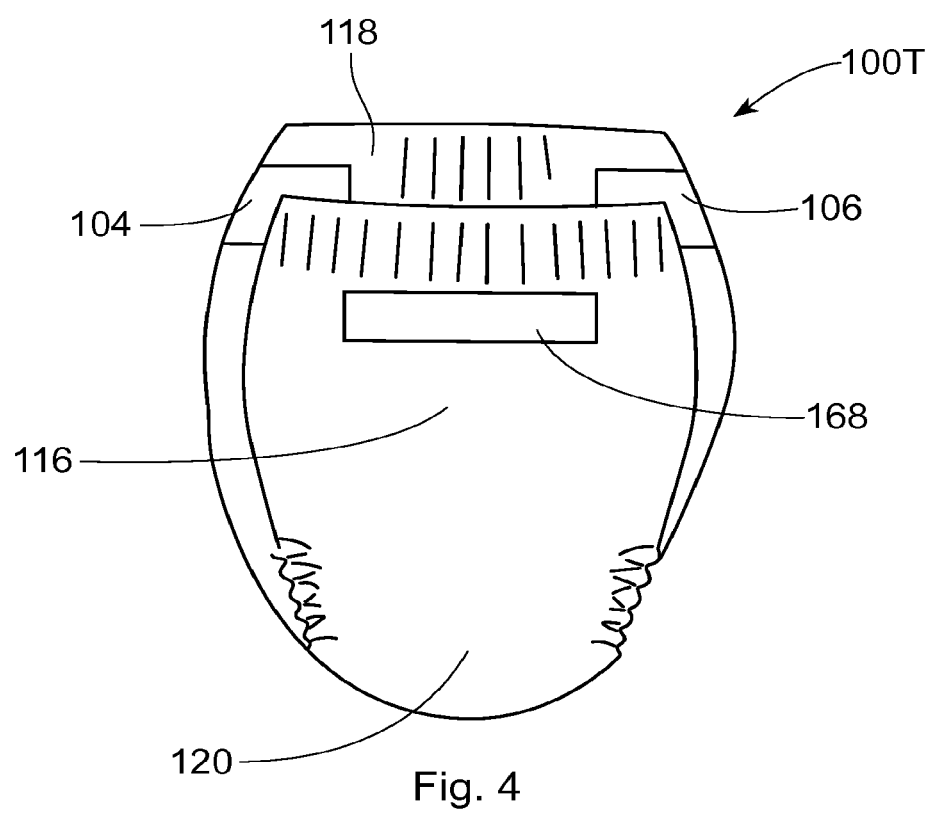
FIG. 4 is a front perspective view of the taped diaper of FIG. 1 in a folded configuration in accordance with one non-limiting embodiment.

Taped diapers may be manufactured and provided to consumers in a configuration where the front waist region 116 and the back waist region 118 are not fastened, pre-fastened, joined, or connected to each other as packaged, prior to being applied to the wearer. As shown in FIG. 4, for example, the taped diaper 100T may be folded about a lateral centerline with the wearer-facing surface 132 of the first waist region 116 in surface to surface contact with the wearer-facing surface 132 of the second waist region 118 without fastening or joining the waist regions together. The back ears 104 and 106 formed in the belt portion 103 and/or the front ears 108 and 110 when present may also be folded laterally inward toward the inner or wearer-facing surfaces 132 of the first and second waist regions 116 and 118.

The taped diaper 100T may comprise various configurations of fastening elements to enable fastening of the front waist region 116 and the back waist region 118 together to form a closed waist circumference and leg openings once the taped diaper is positioned on a wearer. For example, as shown in FIG. 1A, the taped diaper 100T may comprise first and second back ears 104 and 106 formed in the belt portion 103 and first and second front ears 108 and 110, wherein the first and second back ears 104 and 106 are configured to comprise fastening components 162 and 164. The first and second front ears 108 and 110 may also be formed in a belt portion in some embodiments. Each fastening component 162 and 164 may form a portion of or may be permanently bonded, adhered or otherwise joined directly or indirectly to one of the substrates 129 and 131 of the belt portion 103, in the back waist region 118. In other embodiments, the fastening components 162 and 164 may each be attached or joined to the front ears 108 and 110. The fastening components may also be permanently bonded or joined at or adjacent the side edges 128 and 130 of the absorbent article in various ways, such as for example, by adhesive bonds, sonic bonds, pressure bonds, thermal bonds or combinations thereof.

The first fastening component 162 and/or the second fastening component 164 may comprise various types of releasably engageable fasteners and may also comprise various types of refastenable fastening structures. For example, the first and second fastening components 162 and 164 may comprise mechanical fasteners, 166, in the form of hook and loop fasteners, hook and hook fasteners, macro-fasteners, buttons, snaps, tab and slot fasteners, tape fasteners, adhesive fasteners, cohesive fasteners, magnetic fasteners, hermaphrodidic fasteners, and the like. Some examples of fastening systems and/or fastening components 162, 164 are discussed in U.S. Pat. Nos. 3,848,594, 4,662,875, 4,846, 815, 4,894,060, 4,946,527, 5,151,092, 5,221,274, 6,251,097, 6,669,618, 6,432,098, and 7,799,006 and U.S. Patent Publication No. 2007/0078427.

As previously mentioned, the fastening components 162 and 164 may be configured to releasably and/or refastenably engage or connect with another portion of the diaper 100T. For example, as shown in FIG. 1, the diaper 100T may comprise a connection zone 168, sometimes referred to as a landing zone, in the first waist region 116. In an embodiment, the connection zone 168 may be formed on or attached to a belt portion in the front waist region 116. As such, when the taped diaper 100T is placed on a wearer, the fastening components 162 and 164 may be pulled around a portion of the waist of the wearer and connected with the connection zone 168 in the first waist region 116 to form a closed waist circumference and a pair of laterally opposing leg openings. It is to be appreciated that the connection zone 168 may be constructed from a separate substrate that is connected with the chassis 102 or belt portion of the taped diaper 100T. In some embodiments, the connection zone 168 may be integrally formed as part of the backsheet 136 or a belt portion of the diaper 100T or may be formed as part of the first and second ears in one or both of the waist regions, such as described in U.S. Pat. Nos. 5,735,840 and 5,928,212.

The taped diaper 100T may comprise a non-engagement zone disposed on the same surface and in the same waist region as the fastening components 162 and 164. The non-engagement zone may be configured to help prevent the fastening components 162 and 164 from becoming engaged with other elements of the absorbent article prior to use of the absorbent article. The non-engagement zone may comprise a film, coating, or other material that does not attach to or engage with the fastening components 162 and 164. In certain embodiments, the non-engagement zone may be in surface to surface contact with the fastening surface of the fastening components 162 and 164 when the taped diaper 100T is packaged.

In contrast to taped diapers, pant diapers may be manufactured and provided to consumers in a configuration wherein the front waist region 116 and the back waist region 118 are fastened, pre-fastened, joined, or connected to each other as packaged, prior to being applied to the wearer. As such pant diapers may have a continuous perimeter waist opening and continuous perimeter leg openings designed for infant, child, and/or adult wearers. As discussed in more detail below, a diaper pant may be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers may be preformed anywhere along the circumference of the waist region (e.g., side fastened or connected, front waist fastened or connected, rear waist fastened or connected).

Figure 5:
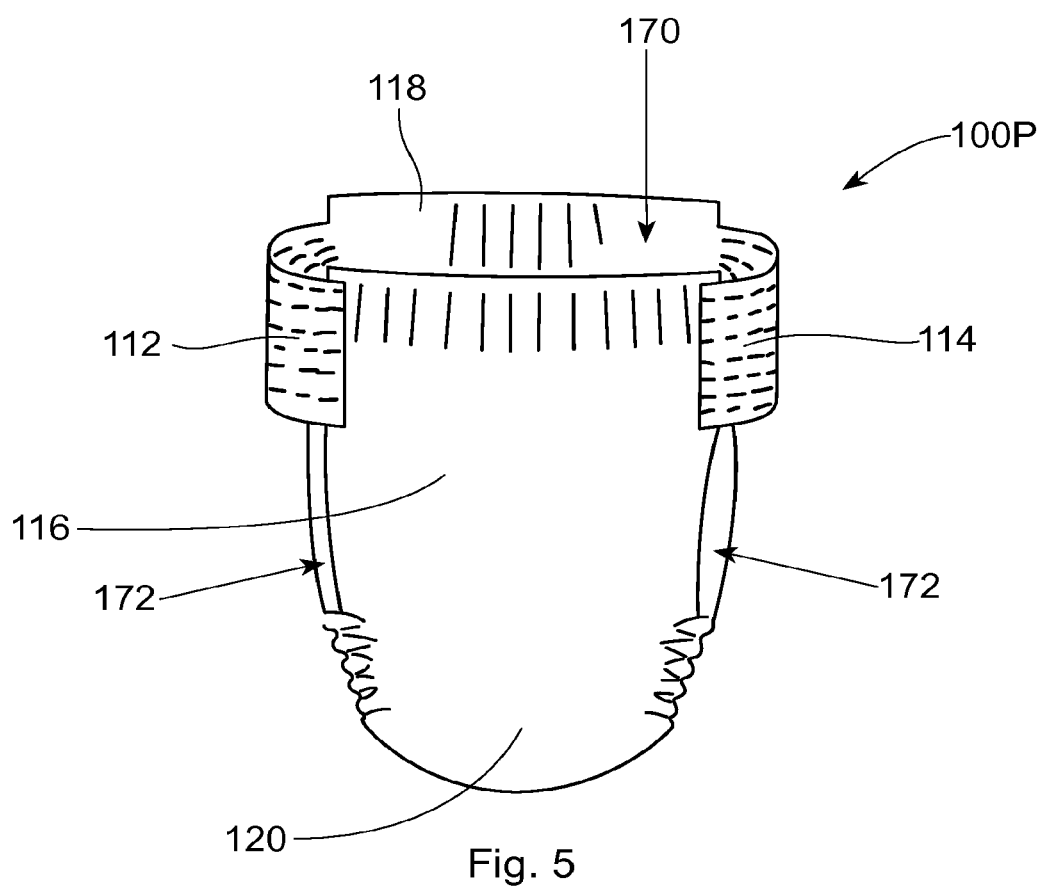
FIG. 5 is a perspective view the pant diaper of FIG. 2 with the belt portion joining opposing waist regions in accordance with one non-limiting embodiment.

In some embodiments, pant diapers 100P may be configured with belt ears 112 and 114 that may be formed with or attached to a belt portion in one or both of the waist regions 116 and 118 or to the chassis 102. For example, FIGS. 2 and 5 show a pant diaper 100P including first and second belt ears 112 and 114 in the rear waist region 118. The belt ears 112 and 114 may be formed in the belt portion 111 or be joined to the belt portion 111 or joined to chassis 102. The belt ears 112 and 114 may be substantially rectangular in shape or the belt ears 112 and 114 may be shaped in such a way as to provide an integral tab for ease of opening and refastening. The belt ears 112 and 114 may be also be extensible or elastically extensible in the lateral direction and/or the longitudinal direction. The belt ears 112 and 114 may comprise one or more films, nonwovens, or a combination of films and nonwovens. The element elements 105 may be elastically extensible in at least the lateral direction.

As previously mentioned and with reference to FIGS. 2 and 5, the first and second belt ears 112 and 114 formed on the belt portion 111 or joined to the belt portion 111 or joined to the chassis 102 may connect the first waist region 116 with the second waist region 118 of the chassis 102 to form a waist opening 170 and two leg openings 172. For example, proximal end regions 174 of the first and second belt ears 112 and 114 are formed with the belt portion 111 and distal end regions 176 of the first and second belt ears 112 and 114 are connected with the front waist region 116 of the chassis 102 to the form the pant diaper 100P.

It is to be appreciated that the distal end regions 176 of one or both the belt ears 112 and 114 may be connected with the front waist region 116 of the chassis 102 in various ways. For example, in some configurations, the belt ears 112 and 114 may be permanently connected with opposing waist regions and cannot be refastened once broken. Such permanent seams are pre-closed to provide a product that looks like underwear and may be applied like underwear (i.e., a pant that may be pulled-on over the legs). Disposable pant diapers with permanent seams may require a separate element for disposal such as a disposal tape disposed on the outer surface of the absorbent article. Other disposable pant diapers may have non-permanent seams and may be refastenable, thereby allowing the caregiver to open the initial waist opening circumference and leg openings and reclose them to facilitate application similar to a traditional tape style diaper. As such, the distal end regions 176 of the belt ears 112 and 114 may be permanently bonded, releasably connected, and/or refastenably connected with the opposing waist region of the chassis 102, with for example, adhesives, cohesives, thermal bonding, ultrasonic bonding, mechanical bonding and mechanical fastening (e.g., hook and loop type fasteners). For example, one or more fastener elements may be located on or form a portion of the belt ears and may be adapted to refastenably connect with one or more corresponding fastening elements located in the first or second waist regions 116 and 118 or alternatively the fastener elements may be adapted to refastenably connect with one or more components of the absorbent article including the belt ears 112 and 114. It should be appreciated that the belt ears may also be formed as continuous extensions of the first and second waist regions of the chassis 102.

The ability to refasten an initially pre-fastened pant diaper may offer convenience to the caregiver. In some instances, it may be more convenient to apply the absorbent article like a traditional tape style diaper when away from home or when it is inconvenient to remove the clothing and/or shoes. Because it is difficult to predict when a change will be necessary and therefore when a particular mode of application will be needed, it is beneficial to have a disposable pant diaper that is adaptable to being applied either as a traditional tape style diaper or as a disposable pant diaper, pull-on. In addition, an absorbent article that may be applied like a traditional tape style diaper or a disposable pant diaper also permits inspection of the interior of the product without having to pull the product down. These refastenable structures may also provide dual functionality enabling the wrapping and disposal of the used product.

Figure 6:
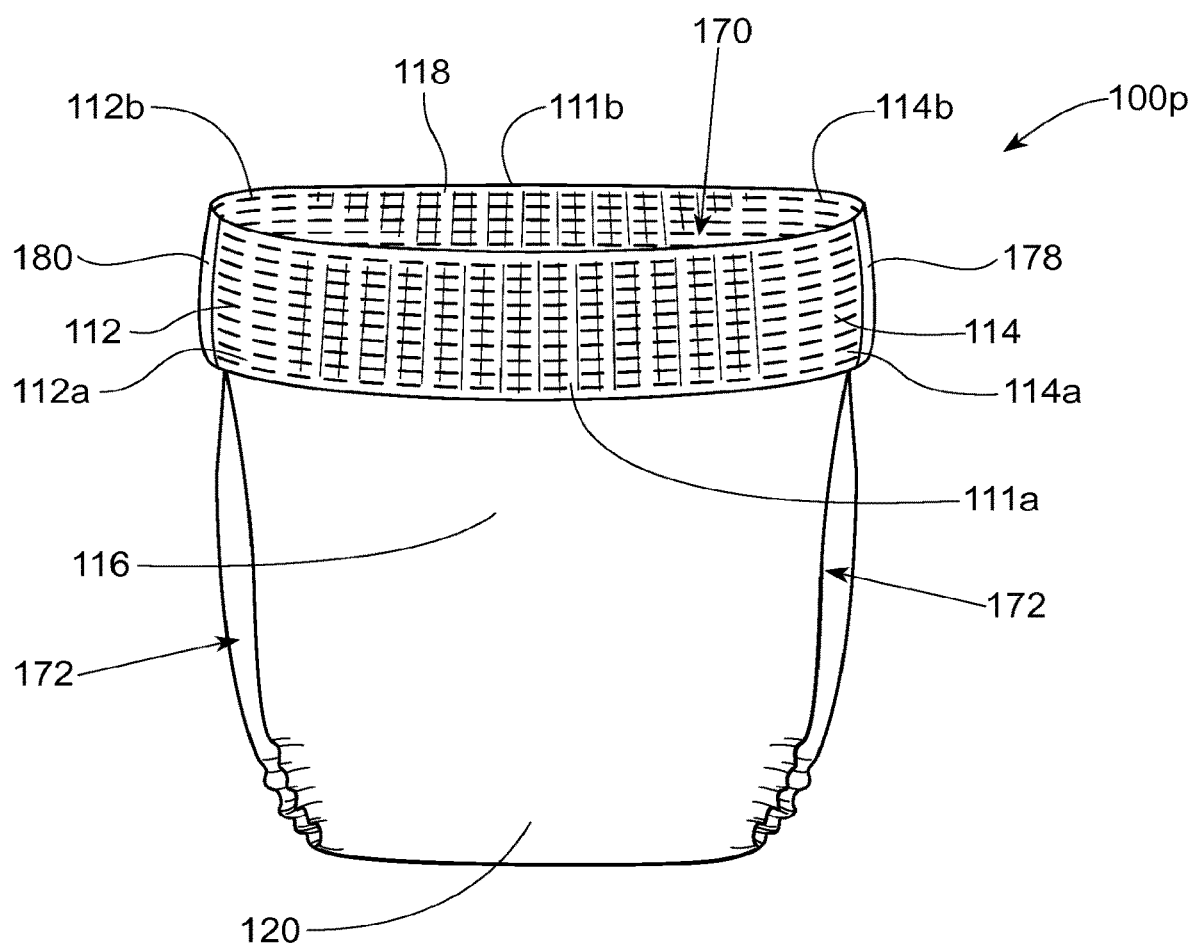
FIG. 6 is a perspective view the pant diaper of FIG. 3 with the belt portions joining the opposing waist regions in accordance with one non-limiting embodiment.

As previously mentioned, the belt ears formed in the belt portions of pant diapers may be configured in different ways. It is to be appreciated that the belt ears may be formed by connecting ear panels formed in the belt portions 111a and 111b together. In some embodiments, pant diapers may be configured with belt ears formed with the belt portions 111a and 111b in both of the waist regions 116 and 118. For example, FIGS. 3 and 6 show a pant diaper 100P, wherein the first belt ear 112 formed in the belt portion 111a comprises a first ear panel 112a connected with a second ear panel 112b, and the second belt ear 114 formed in the belt portion 111a comprises a first ear panel 114a connected with a second ear panel 114b. The first ear panels 112a, 114a each comprise proximal regions 174a formed in the belt portion 111a, which is connected to, joined to, or formed with the chassis 102. Second ear panels 112b, 114b may each comprise proximal regions 174b formed in the belt portion 111b, which is connected to, joined to, or formed with the second waist region 118 of the chassis 102. A distal region 176a of the first ear panel 112a and a distal region 176b of the second ear panel 112b may be connected with each other along a first side seam 178 to form the first belt ears 112. Likewise, a distal region 176a of the first ear panel 114a and a distal region 176b of the second ear panel 114b may be connected with each other along a second side seam 180 to form the second belt ear 114.

It should also be appreciated that the ear panels in one waist region may have the same lateral extent from the side edge of the chassis 102 to the distal edge of the ear panel as the longitudinally opposed ear panels in the opposite waist region or alternatively the ear panels disposed in a first waist region 116 may have different lateral extent as measured from the side edge of the chassis 102 to the distal edge of the ear panel than the ear panels disposed in a second waist region 118.

As such, for a pant diaper including side seams, portions of the pant diaper 100P adjacent the side edges 135a and 135b on the first and second belt portions 111a and 111b may be connected or joined to form a first permanent side edge seam 178 and a second permanent side edge seam 180. The connection of the side edge seams 178 and 180 define the initial waist opening 170 and a pair of leg openings 172. In another configuration, a pant diaper 100P may comprise a first mating fastening component having a fastening surface and an opposing attachment surface, wherein the attachment surface is joined directly to the interior or exterior surface of the pant diaper in a first waist region 116. The pant diaper may further comprise a second mating fastening component having a fastening surface and an opposing attachment surface, wherein the attachment surface may be joined directly to the same surface or opposing surface of the pant diaper as the first fastening component. The second mating fastening component may be joined to or may form a portion of the surface to which the attachment surface of the first mating fastening component is joined or may be joined to or may form a portion of an opposing surface relative to the surface to which the attachment surface of the first mating fastening component is joined.

In yet another configuration, the pant diaper may comprise a frangible separation zone that may be disposed laterally inward of the side edge seams 178 and 180 that allows the initial waist opening circumference 170 and leg openings 172 of the pant 100P to be opened for removal or to enable application as a traditional tape style diaper. As discussed above, the pant diaper may further comprise a first fastening component and a second fastening component disposed in one of the front or back waist regions 116 and 118. Each of the fastening components may be disposed on the same surface of the pant diaper 100P (e.g., the outer or garment-facing surface 134) or on opposing surfaces. The fastening components may be capable of being fastened in a traditional tape style diaper fashion or fastened to reform a secondary waist opening circumference and leg openings after the initial waist opening circumference and leg openings have been broken. In addition, the fastening components may be used to aid disposal of a soiled pant.

As previously mentioned, the bonds of the side edge seams 178 and 180 may be permanent and may be formed in various ways appropriate for the specific materials employed. Thus, example bond types may comprise discrete bonds such as sonic sealed bonds, heat sealed bonds, high pressure bonds, radio frequency bonds, adhesive or cohesive bonds, sewed bonds, autogenous bonds, and combinations thereof. In accordance with one aspect of the present disclosure, the permanent side edge seams 178 and 180 may be joined by a predetermined pattern of heat/pressure or ultrasonic welds which withstands the forces and stresses exacted onto the side edge seams 178 and 180 during application and wear of the pant 100P. The permanent side edge seams 178, 180 may be formed as disclosed in U.S. Pat. Nos. 5,779,831, 5,772,825, 5,607,537, 5,622,589, 5,662,638, 6,042,673, and 6,726,792.

Because the pant diaper 100P may be configured with permanent side edge seams 178 and 180, both permanent side edge seams may be pre-closed, meaning that the side edge seams are closed prior to removal of the diaper pant 100P from its package, and therefore prior to being donned on the lower torso of the wearer. The pre-closed permanent side edge seams 178 and 180 may form an initial waist opening circumference and leg circumferences. The initial waist opening circumference and leg circumferences may be opened at predetermined frangible separation zones. In an embodiment, the permanent side edge seams cannot be reclosed to form the secondary waist opening circumference and leg openings.

Additionally, various diaper pant configurations are disclosed in U.S. Pat. Nos. 5,246,433, 5,569,234, 6,120,487, 6,120,489, 4,940,464, 5,092,861, 5,897,545, 5,957,908, 7,101,359, 7,407,468, 7,820,875, and 7,799,006 and U.S. Patent Publication Nos. 2003/0233082, 2003/0088220, 2003/0233082, 2005/0215970, 2007/0078427, 2007/0074381, 2007/0078426, and 2008/0107861.

Figure 7:
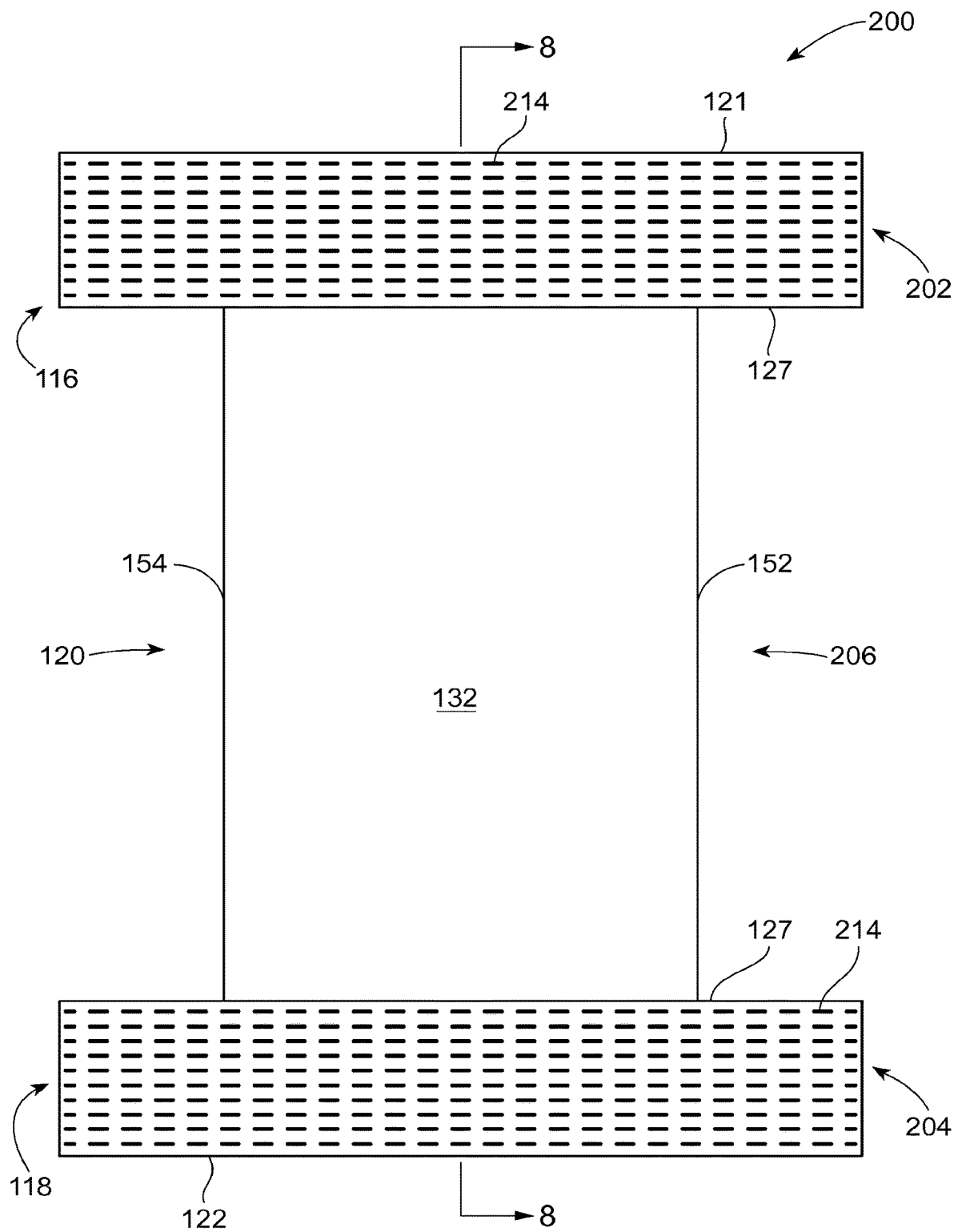
FIG. 7 is a plan view of a pant diaper comprising a chassis and two belt portions extending from first and second end portions of the chassis in accordance with one non-limiting embodiment.

In an embodiment, referring to FIG. 7, a simplified absorbent article 200, such as a pant, for example, is illustrated in FIG. 7. Various components have been removed for clarity in illustration. The absorbent article 200 may comprise a front or first belt portion 202 and a rear or second belt portion 204. The first belt portion 202 may be positioned in the first waist region 116, while the second belt portion 204 may be positioned in the second waist region 118. The first belt portion 202 and the second belt portion 204 are together intended to encircle at least a portion of the waist of the wearer when portions of the first belt portion 202 are joined or releasably joined to portions of the second belt portion 204. The first and second belt portions 202 and 204 may be connected to each other by a chassis 206. The chassis 206 may form the crotch region 120 in the absorbent article 200. The chassis 206 may also form portions of the first and second waist regions 116 and 118. In various embodiments, the first and second belt portions 202 and 204 may overlap first and second end portions of the chassis 206. This overlap may occur on the wearer-facing surface or on the garment-facing surface of the chassis 206. In the illustration of FIG. 7, the wearer-facing surface of the chassis 206 is oriented towards the viewer. In other embodiments, there may not be any overlap or very limited overlap of the first and second belt portions 202 and 204 with the chassis 206. In such an embodiment, the first and second belt portions 202 and 204 may be joined to the first and second end portions of the chassis 206 at or near the point of intersection between the end portions and the belt portions 202 and 204. FIGS. 8a-8g are some example structural cross-sections taken about line 8-8 of FIG. 7 in various embodiments. Also, the number of elastic elements in the cross-sections is not limiting and more or less elastic elements may be used. Various features of absorbent articles are eliminated in FIGS. 8a-8g for clarity in illustration.

Figure 8A:
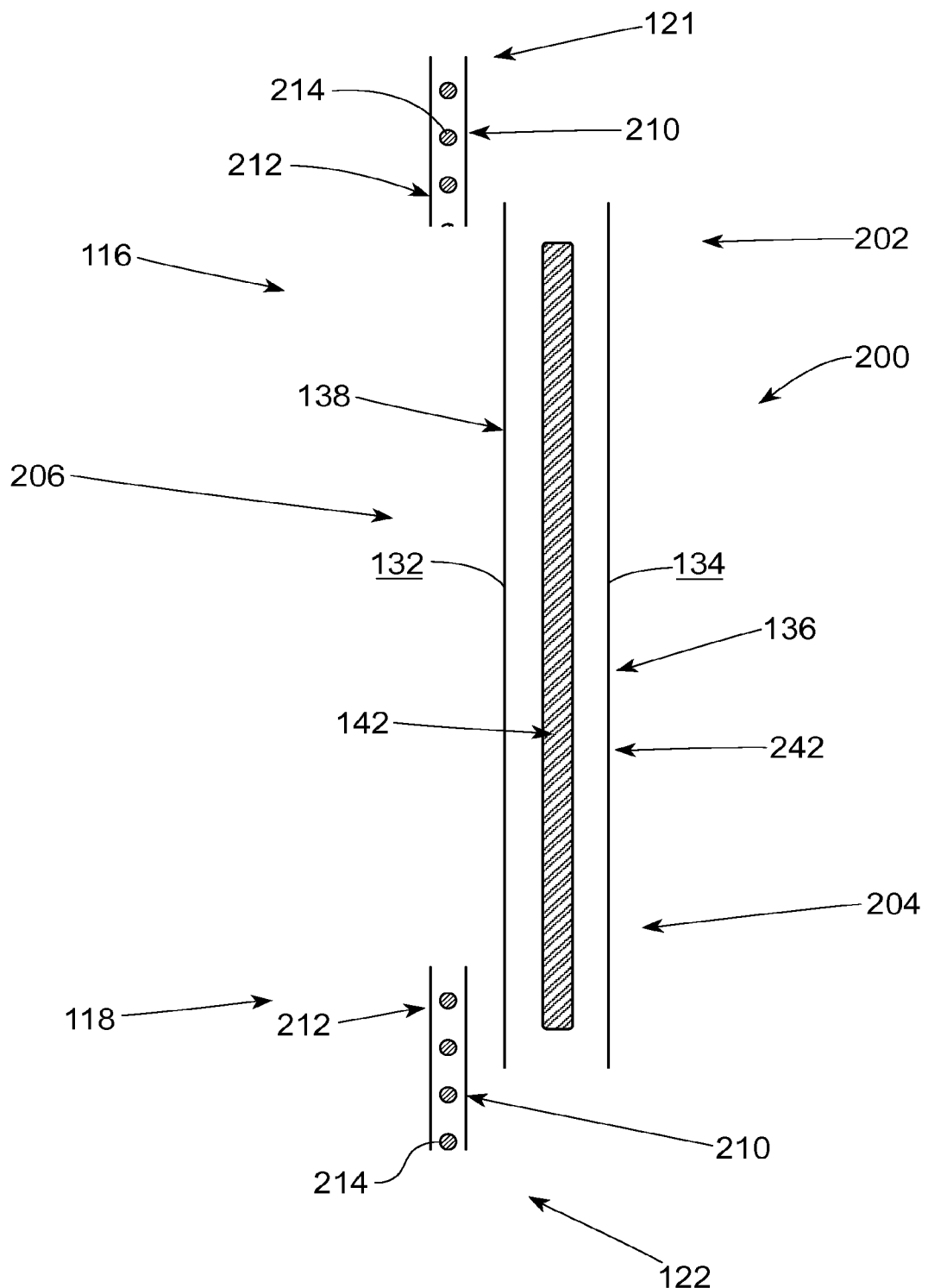
FIGS. 8a-8g are example cross-sectional structures taken about line 8-8 of FIG. 7. in accordance with various non-limiting embodiments.
Figure 8B:
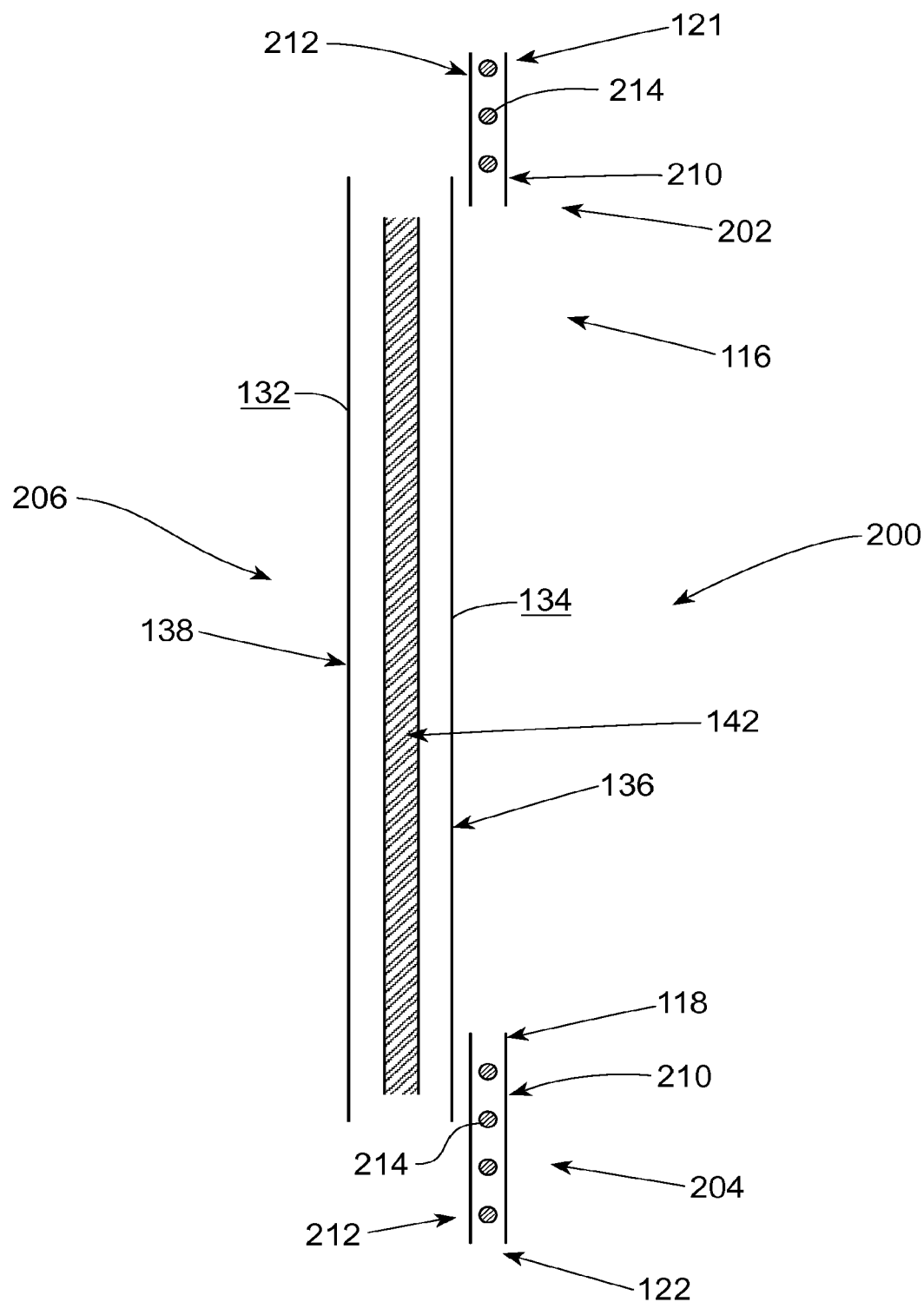

In an embodiment, referring to FIGS. 8a and 8b, the absorbent articles 200 may comprise the first and second belt portions 202 and 204 intended to encircle at least a portion of the waist of the wearer. The first and second belt portions 202 and 204 may be connected by the chassis 206 of the absorbent article 200. The first and second belt portions 202 and 204 may comprise a first substrate 210 forming a portion of the outer, garment-facing surface 134 of the absorbent article 200. The first substrate 210 on the belt portions 202 and 204 may be formed of two longitudinally spaced webs of material. The first and second belt portions 202 and 204 may also comprise a second substrate 212 forming a portion of the inner, wearer-facing surface 132 of the absorbent article 200. The second substrate 212 on the belt portions 202 and 204 may also be formed of two longitudinally spaced webs of material. The second substrate 212 may also be discontinuous and spaced apart in a transverse direction.

The first and second substrates 210 and 212 may be formed of the same, or substantially the same, material or may comprise different materials. The first and second substrates 210 and 212 may be formed from nonwovens, films, foams, elastics, nonwovens, or combinations thereof. The first and second belt portions 202 and 204 may also comprise the elastic elements 214 disposed at least partially between the first and second substrates 210 and 212. Any suitable number of elastic elements 214 may be provided in each belt portion. The elastic elements 214 may comprise one or more elastic strands, elastomeric films, elastomeric ribbons, elastomeric nonwovens, elastomeric filaments, elastomeric adhesives, elastomeric foams, scrims, or combinations thereof. A portion of the elastic elements 214 may be directly combined with the outer, garment-facing surface or layer 134. The chassis 206 may comprise at least a portion of the outer, garment-facing surface 134, the backsheet 136, at least a portion of the inner, wearer-facing surface 132, the topsheet 138, and the absorbent core 142 disposed between the topsheet 138 and the backsheet 136. The backsheet 136 may be formed of a nonwoven material, a woven material, and/or films or laminates comprising a combination of one or more of these materials. In an embodiment, the backsheet 136 may be a film and nonwoven laminate, wherein the nonwoven of the laminate may be an outer cover substrate 242 of the absorbent article 200. In addition, the chassis 206 may comprise elasticized barrier leg cuffs 156 (see e.g., FIG. 3) disposed at or adjacent the side edges 152 and 154 (see e.g., FIG. 3) of the chassis 206. The first and second substrates 210 and 212 may overlap at least a portion of the chassis 206 and one or both of the belt portions 202 and 204 may be disposed on the outer, garment-facing surface 134 of the chassis 206 or on the inner, wearer-facing surface 132 of the chassis 206. A portion of the first or second substrates 210 and 212 may be directly attached to the outer cover substrate 242. Alternatively, the first and second substrates 210 and 212 may comprise longitudinally spaced webs of material forming a first surface of one or more of the belt portions 202 and 204, wherein the webs are folded along the waist opening edges 121 or 122 or the leg opening edges 127 of one or more of the belt portions 202 and 204 to wrap the elastic elements 214 and form at least a portion of the second surface of one or more of the belt portions 202 and 204. Stated another way, at least a portion of the inner, wearer-facing surface 132 and at least a portion of the outer, garment-facing surface 134 of each of the belt portions 202 and 204 may be formed from a single web of material.

Figure 8C:
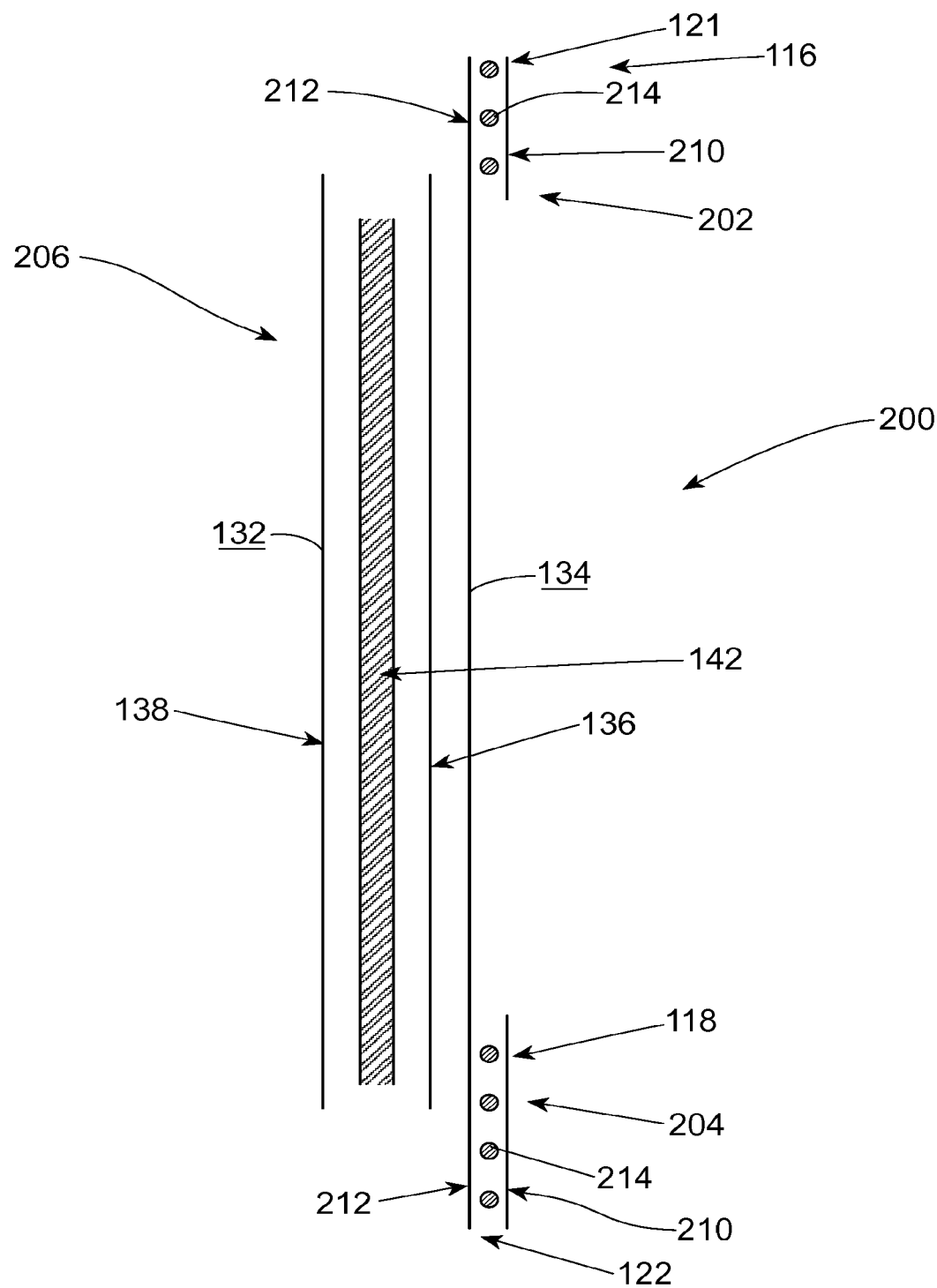
Figure 8D:
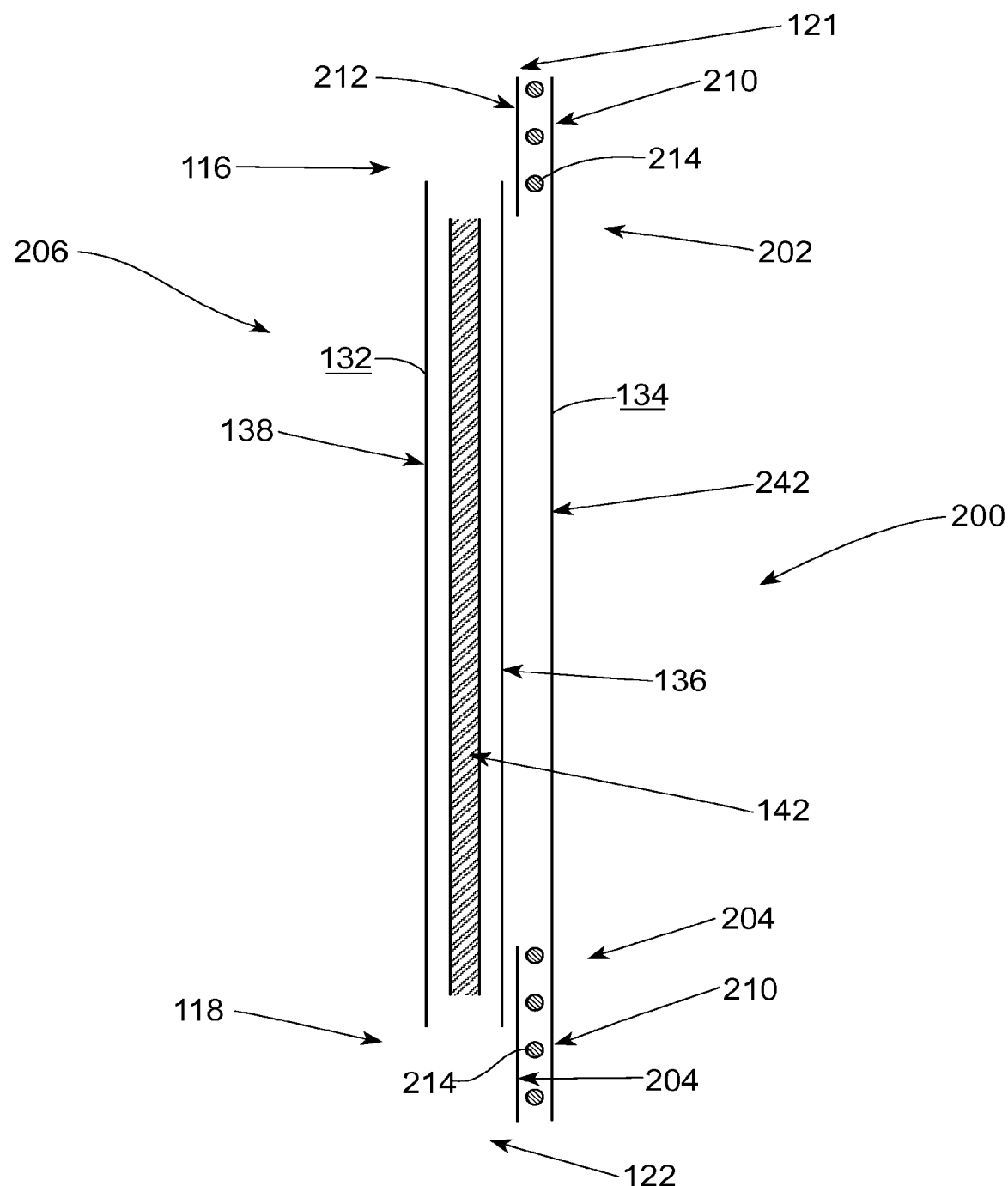

In an embodiment, referring to FIGS. 8c and 8d, the first and second belt portions 202 and 204 may comprise a first substrate 210 extending from a first waist opening edge 121 in a first waist region 116 through the chassis 206 to a longitudinally opposing second waist opening edge 122 in a second waist region 118 and forming a portion of the outer, garment facing surface 134 of the absorbent article 200. The first and second belt portions 202 and 204 may comprise a second substrate 212 forming a portion of the inner, wearer-facing surface 132 of the absorbent article 200. The second substrate 212 may extend from the first waist opening edge 121 to the second waist opening edge 122. In other embodiments, the second substrate 212 may be formed of two longitudinally spaced webs of material. The first and second belt portions 202 and 204 may also comprise a plurality of elastic elements 214 disposed at least partially between the first and second substrates 210 and 212. The elastic elements 214 may be the same as described above. The chassis 206 may comprise at least a portion of an outer, garment facing surface 134, a backsheet 136, at least a portion of an inner, wearer-facing surface 132, a topsheet 138, and an absorbent core 142 disposed between the topsheet 138 and the backsheet 136. The first substrate 210 or the second substrate 212 may form a portion of the outer, garment-facing surface 134. In addition, the chassis 206 may comprise elasticized barrier leg cuffs 156 disposed at or adjacent the side edges 152 and 154 of the chassis 206. The second substrate 212 may overlap at least a portion of the chassis 206 and one or both of the second substrate webs may form the outer surface of the first substrate 210 or the inner surface of the first substrate 210. Alternatively, the front portion and/or the rear portion of the first substrate 210 may be folded along one of the waist opening edges 121 or 122 of one of the waist regions 116 or 118 to wrap the elastic elements 214 and form a portion of the second substrate 212 of one or both of the first and second belt portions 202 and 204. Stated another way, the inner surface and outer surface of each of the first and second belt portions 202 and 204 may be formed from a single web of material.

Figure 8E:
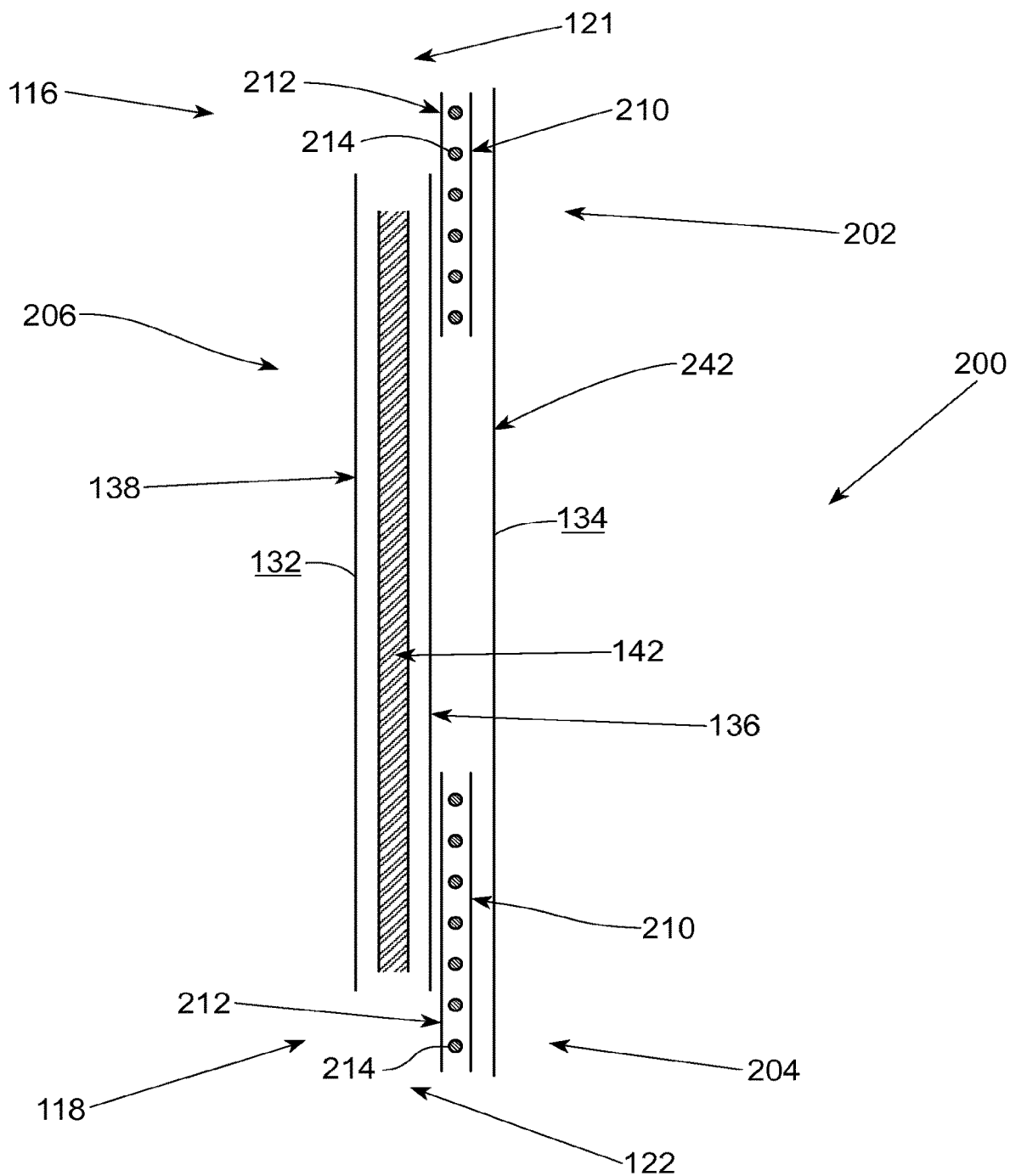
Figure 8F:
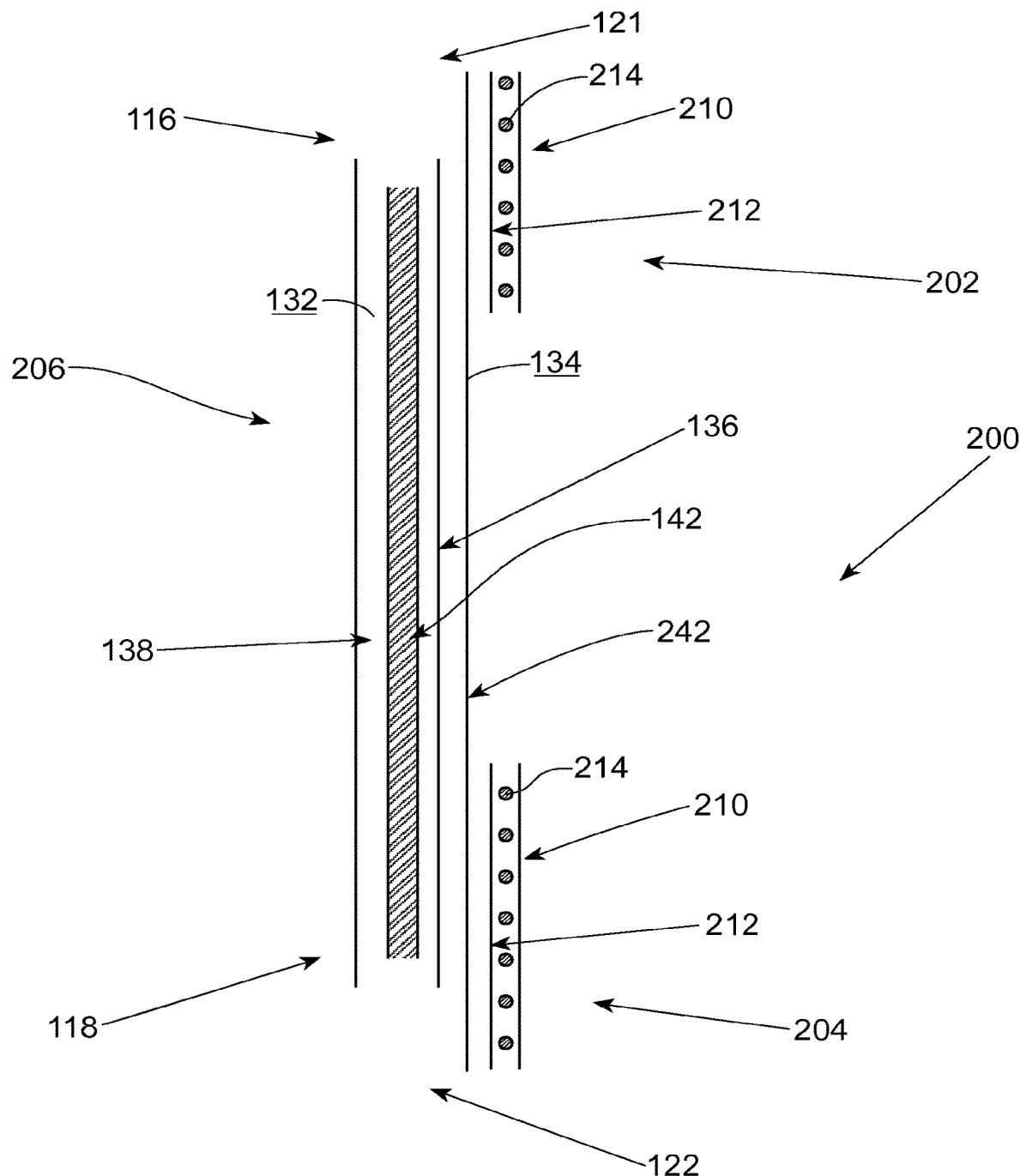

In an embodiment, referring to FIGS. 8e and 8f, the absorbent articles 200 may comprise a full outer cover substrate 242, extending from a first waist opening edge 121 in a first waist region 116, through the chassis 206 and to the longitudinally opposing second waist opening edge 122 in a second waist region 118. The absorbent article 200 may also comprise first and second belt portions 202 and 204 intended to encircle the waist of the wearer. The first and second belt portions 202 and 204 may be connected to the outer cover substrate 242 and/or to the chassis 206 of the absorbent article 200. The first and second belt portions 202 and 204 may comprise a first substrate 210 forming a portion of the outer, garment-facing surface 134 of the belt 202 or 204. The first substrate 210 may be formed of two longitudinally spaced webs of material. The first and second belt portions 202 and 204 may comprise a second substrate 212 forming a portion of the inner, wearer-facing surface 132 of the absorbent article 200. The second substrate 212 may also be formed of two longitudinally spaced webs of material. The first and second substrates 210 and 212 may be formed of substantially the same material or may comprise different materials. The first and second substrates 210 and 212 may be formed from nonwovens, films, foams, or combinations thereof. The first and second belt portions 202 and 204 may also comprise an elastic elements 214 disposed between the first and second substrates 202 and 204. The elastic elements 214 may be the same or similar to that described above. The first and second belt portions 202 and 204 may be disposed on the interior surface of the outer cover substrate 242. Alternatively, the first and second belt portions 202 and 204 may be disposed on the outer surface, or garment-facing surface 134 of the outer cover substrate 242. In such an embodiment, the outer cover substrate 242 may form a portion of the inner, garment-facing surface 132 of the absorbent article 200 in the waist regions 116 and 118 and the first substrate 210 may form a portion of the outer, garment-facing surface 134 of the absorbent article 200. The second substrate 212, when present, may be disposed between the first substrate 210 and the outer cover substrate 242. The chassis 206 of the absorbent article 200 may comprise at least a portion of an outer, garment-facing surface 134, a backsheet 136, at least a portion of an inner, wearer-facing surface 132, a topsheet 138, and an absorbent core 142 disposed between the topsheet 138 and the backsheet 136. In addition, the chassis 206 may comprise elasticized barrier leg cuffs 156 (see e.g., FIG. 3) disposed at or adjacent the side edges 152 and 154 (see e.g., FIG. 3) of the chassis 206. One or both of the first and second belt portions 202 and 204 may overlap at least a portion of the chassis 206 and one or both of the belt portions 202 and/or 204 may be disposed on the outer, garment-facing surface 134 of the chassis 206 or on the inner, wearer-facing surface 132 of the chassis 206. One or both of the first and second belt portions 202 and/or 204 may be disposed on the interior surface of the outer cover substrate 242 or on one or both of the belt portions 202 and/or 204 may be disposed on the exterior surface of the outer cover substrate 242. One or both of the first and second belt portions 202 and/or 204 may comprise longitudinally spaced webs of material forming a first surface of the belt portion 202 or 204, wherein the webs may be folded along the waist opening edge 121 or 122 of the belt portion 202 or 204 to wrap the elastic elements 214 and form at least a portion of the second surface of the belt portion 202 or 204. Stated another way, a portion of or the entirety of the inner surface and outer surface of one or both of the belt portions 202 or 204 may be formed from a single web of material. The rugosities, wrinkles, folds, pleats, or textures in one or both of the front and rear belt portions 202 and 204 may have a different configuration, size, orientation, shape, etc., than that of the outer cover substrate 242 and/or the backsheet 136.

Figure 8G:
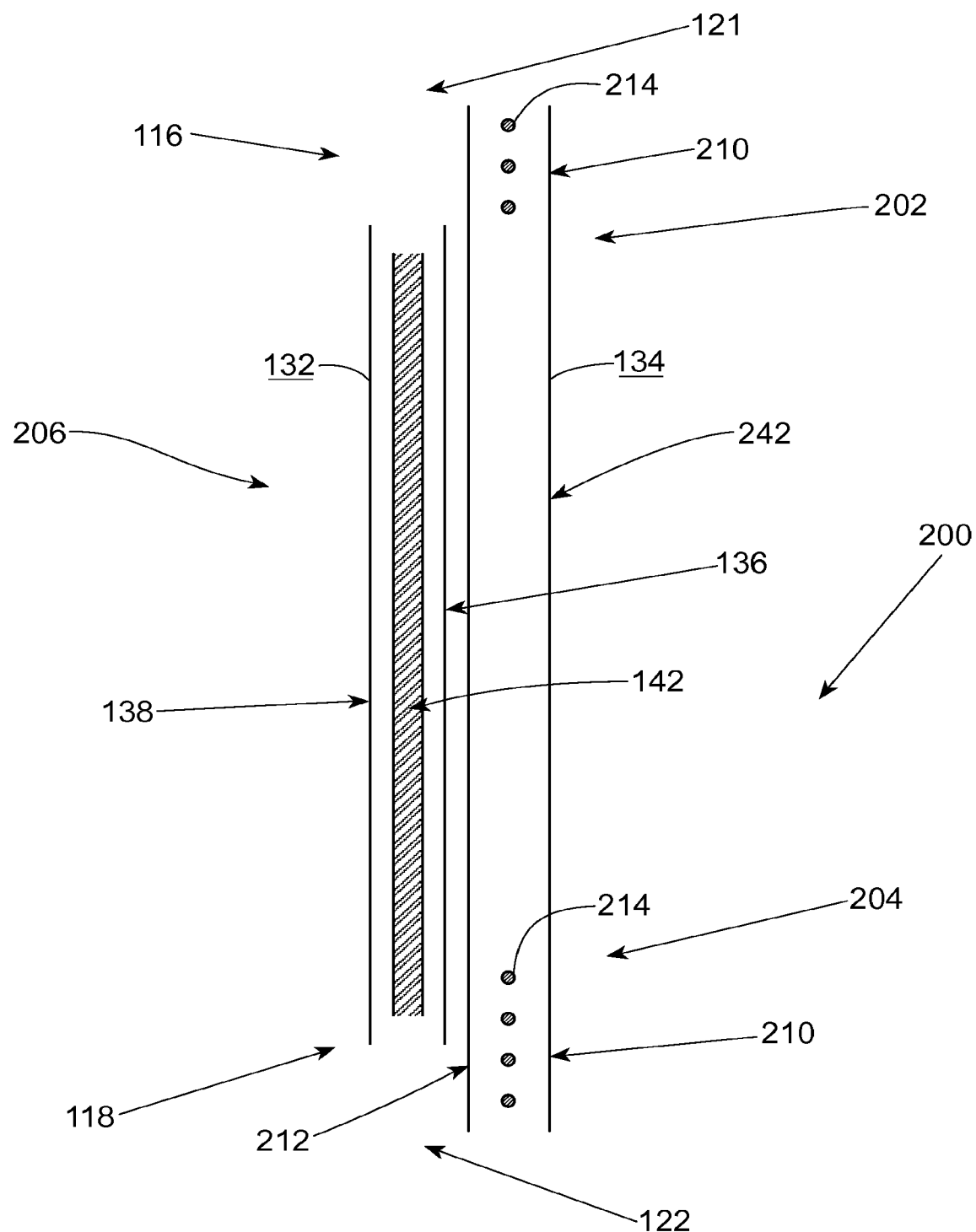

In an embodiment, referring to FIG. 8g, the first and second belt portions 202 and 204 may comprise a first substrate 210 forming a portion of the outer, garment-facing surface 134 of the absorbent article 200 and a second substrate 212 forming a portion of the inner, wearer-facing surface 132 of the absorbent article 200. The second substrate 212 may be laterally discontinuous and spaced apart in a transverse direction. The first and second substrates 210 and 212 may be formed of the same, or substantially the same material, or may comprise different materials. The first and second substrates 210 and 212 may be formed from nonwovens, films, foams or combinations thereof. The first and second belt portions 202 and 204 may also comprise elastic elements 214 disposed between the first and second substrates 210 and 212. The elastic elements 214 may be the same as or to similar to that described above. A portion of the elastic elements 214 may be directly combined with the outer cover substrate 242. The chassis 206 may comprise at least a portion of an outer, garment-facing surface 134, a backsheet 136, at least a portion of an inner, wearer-facing surface 132, a topsheet 138, and an absorbent core 142 disposed between the topsheet 138 and the backsheet 136. In an embodiment, the backsheet 136 may be a nonwoven and film laminate, wherein the nonwoven may be formed by the outer cover substrate 242. In addition, the chassis 206 may comprise elasticized barrier leg cuffs 156 (see e.g., FIG. 3) disposed at or adjacent the side edges 152 and 154 (see e.g., FIG. 3) of the chassis 206. The first and second belt portions 202 and 204 may overlap at least a portion of the chassis 206 and one or both of the belt portions 202 and/or 204 may be disposed on the outer, garment-facing surface 134 of the chassis 206 or on the inner, wearer-facing surface 132 of the chassis 206. A portion of the first and/or second substrates 210 and/or 212 may be directly attached to the outer cover substrate 242. The first and second belt portions 202 and 204 may be formed from a first belt substrate extending from the first waist opening edge 121 in the first waist region 116 through the crotch region 120 to the second waist opening edge 122 in the second waist region 118 and forming a portion of the outer, garment-facing surface 134 of the absorbent article 200. The first and second belt portions 202 and 204 may also comprise a second substrate 212 extending from the first waist opening edge 121 in the first waist region 116 through the crotch region 120 to the second waist opening edge 122 in the second waist region 118 and forming a portion of the inner, wearer-facing surface 132 of the absorbent article 200. The first and second substrates 210 and 212 may be formed of the same or substantially the same material or may comprise different materials. The first and second substrates 210 and 212 may be formed from nonwovens, films, foams, woven materials, or combinations thereof. The first and second belt portions 202 and 204 may also comprise elastic elements 214 disposed between the first and second substrates 210 and 212 in one or both of the first and second waist regions 116 and 118. The elastic elements 214 may be the same as or similar to that described above. The chassis 206 may comprise at least a portion of an outer, garment-facing surface 134, a backsheet 136, at least a portion of an inner, wearer-facing surface 132, a topsheet 138, and an absorbent core 142 disposed between the topsheet 138 and the backsheet 136. One or both of the first and second substrates 210 and 212 may form a portion of the outer, garment-facing surface 134. In addition, the chassis 206 may comprise elasticized barrier leg cuffs 156 (see e.g., FIG. 3) disposed at or adjacent the side edges 152 and 154 (see e.g., FIG. 3) of the chassis 206. A portion of one or both of the first and second belt portions 202 and 204 may overlap at least a portion of the chassis 206. Alternatively, the first and second belt portions 202 and 204 may comprise a substrate forming a first surface of the belt portion 202 or 204, wherein the substrate may be folded along the waist opening edge 121 or 122 of the belt portion 202 or 204 to wrap the elastic elements 214 and overlap a portion of the opposing substrate 210 or 212. Stated another way, a portion of the inner surface and a portion of the outer surface of each of the belt portions 202 and 204 may be formed from a single web of material.

In an embodiment, a portion of or the whole of the chassis 206 of the various absorbent articles 200 may be made extensible to a degree greater than the inherent extensibility of the material or materials from which the chassis 206 is made (e.g., the topsheet 138, the backsheet 136). The additional extensibility may be desirable in order to allow the chassis 206 to conform to the body of a wearer during movement by the wearer and in order to allow the wearer of the absorbent article 200, including a chassis 206 having a particular size before extension, to extend the first waist region 116, the second waist region 118, or both of the waist regions 116 and 118 of the chassis 206 to provide additional body coverage for wearers of differing size (i.e., to tailor the absorbent article 200 to the individual wearer). Such extension of the waist region or regions 116 or 108 may give the chassis 206 a generally hourglass shape, so long as the crotch region 120 is extended to a relatively lesser degree than the waist region or regions 116 and 118, and may impart a tailored appearance to the absorbent article 200 when it is worn. In addition, the additional extensibility may be desirable in order to minimize the cost of the absorbent article 200. For example, an amount of material that would otherwise be sufficient only to make a relatively smaller absorbent article lacking this extensibility may be used to make an absorbent article capable of being extended to adequately cover a lower torso of a wearer that is larger than the unextended smaller absorbent article would fit.

In various embodiments, a portion of the chassis 206, for example, a portion of the chassis 206 in one or both of the waist regions 116 and/or 118 may be made laterally extensible to a maximum extensibility greater than a maximum extensibility of the crotch region 120 of the chassis 206 such that a lateral extension of each of the portions to its maximum extensibility imparts an hourglass shape to the chassis 206. In an embodiment, the portion of the chassis 206 underlying and/or immediately adjacent the first and/or second belt portions 202 and/or 204 may be made laterally extensible to a maximum extensibility greater than a maximum extensibility of another portion of the chassis 206, for example the crotch region 230, such that a lateral extension of each of the portions to its maximum extensibility facilitates application of the absorbent article 200 onto the body of a wearer by enabling the waist regions 116 and 118 to be extended to fit over the wearer's hips and, in addition, opening and orienting the leg openings 172 enabling the wearer to place the legs through the openings 172 more effectively.

Additional lateral extensibility in the chassis 206 may be provided in a variety of ways. For example, a material or materials from which the chassis 206 is made may be pleated by any of a plurality of methods. Alternatively, all or a portion of the chassis 206 may be made of a formed web material or a formed laminate of web materials similar or the same as those described in U.S. Pat. No. 5,518,801, issued on May 21, 1996, to Chappell et al. This formed web material may comprise distinct laterally extending regions in which the original material has been altered by embossing, or another method of deformation, to create a pattern of generally longitudinally oriented alternating ridges and valleys. The formed web material may also comprise laterally extending unaltered regions between the laterally extending altered regions. The formed web material may be extended in a direction perpendicular to the ridges up to the point where the ridges and valleys flatten, or substantially flatten, with substantially less force than is required to extend beyond that point. In addition to lateral extensibility, the creation of a formed laminate web, as described above, may provide a backsheet with improved texture and a cloth-like appearance and feel. The deformation may create a cloth-like pattern in the film and may increase the loft of the nonwoven in multi-layer film and nonwoven laminate backsheets.

Alternatively, a portion of the absorbent article 200 may be ring-rolled and, thus, rendered highly extensible as described in U.S. Pat. No. 5,366,782, issued Nov. 22, 1994, to Curro, et al. Specifically, a ring-rolling apparatus may comprise opposing rolls having intermeshing teeth that incrementally stretch and, thereby, plastically deform the material forming the absorbent article 200 (or a portion thereof), thereby rendering the absorbent article 200 extensible in the ring-rolled regions. In an embodiment, an absorbent article may be ring-rolled in a portion of at least one of the first or second waist regions 116 or 118 or in a portion of the chassis 206 underlying and/or immediately adjacent one or both of the first and second belt portions 202 and 204, while other regions or portions may comprise a structured elastic-like formed web material. The absorbent article 200 may be ring-rolled across the entire width in one or both of the waist regions 116 and/or 118 or may be ring-rolled over only a portion of the chassis width.

The front laterally central portion and the back laterally central portion of the chassis 206 may have a different range of extensibility from other portions of the chassis 206. Additionally or alternatively, the laterally central portions may be extensible to a greater or lesser degree when subjected to a given level of opposing tensile forces (i.e., may be more easily or less easily extensible, than other portions of the chassis 206).

Figure 9:
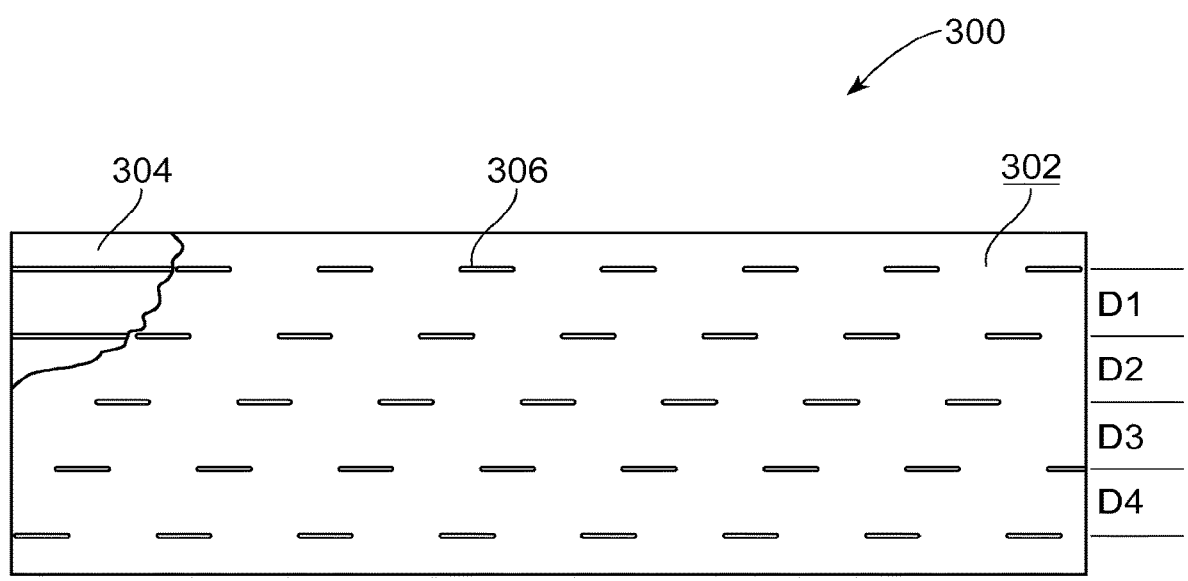
FIG. 9 is a belt portion configured for use as part of an absorbent article in accordance with one non-limiting embodiment.
Figure 10A:
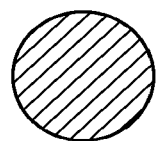
FIGS. 10A-10F illustrate cross-sectional views of elastic elements for use in belt portions of the present disclosure in accordance with various non-limiting embodiments.
Figure 10B:
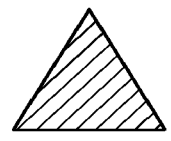
Figure 10C:
Figure 10D:
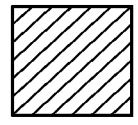
Figure 10E:
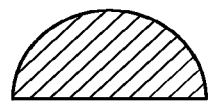
Figure 10F:
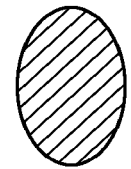
Figure 11:
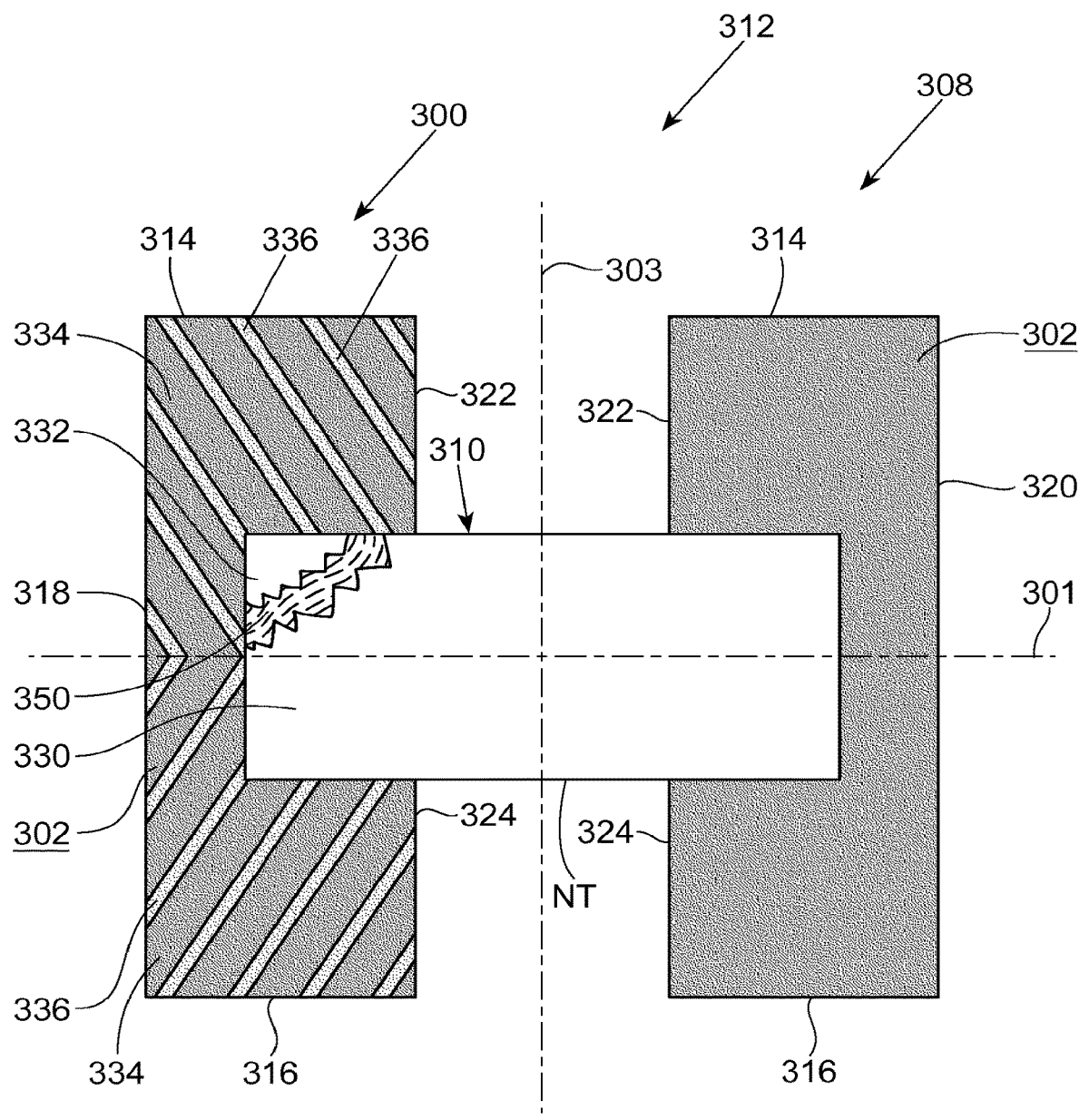
FIGS. 11-15 are schematic illustrations of absorbent articles with belt portions comprising texture zones, forming background patterns and macro patterns, and non-texture zones in accordance with various non-limiting embodiments.

In an embodiment, referring to FIGS. 9 and 11, a belt portion 300 may be formed with, be attached to, be joined to, overlap, and/or extend from a first end portion and/or a second end portion of a chassis 310 of an absorbent article 312. The belt portion 300 may be disposed on a wearer-facing surface or on a garment-facing surface of the chassis 310 or intermediate the garment-facing surface and the wearer-facing surface. The garment-facing surface is facing the viewer in FIGS. 9 and 11. The belt portion 300, in various embodiments, may comprise a first substrate 302, a second substrate 304, and one or more elastic elements, strands, or strips 306 disposed at least partially between the two substrates 302 and 304. The elastic elements 306 may be elongate. The belt portion 300 may comprise one or more texture zones or a single uniform or non-uniform texture zone. The elastic elements 306 may be elongate and may be adhesively joined, or otherwise joined, to a portion of the first substrate 302 and/or to a portion of the second substrate 304. The adhesive may be applied to the portion of the first substrate 302 and/or to the portion of the second substrate 304 in a pattern that defines a rugosity frequency in the one or more texture zones, as described in more detail below. The elastic elements 306 may be intermittently or continuously adhesively or otherwise joined to the portion of the first substrate 302 and/or to the portion of the second substrate 304. In FIGS. 9 and 11, the first substrate 302 is facing the viewer. The first and second substrates 302 and 304 may be comprised of nonwoven materials or other suitable materials as described above. A longitudinal axis 301 and a lateral axis 303 may be defined through the chassis 310.

In an embodiment, referring to FIG. 9, one of or both of the first and second substrates 302 and 304, or portions thereof, may not be provided. In one example, only portions of the elastic elements 306 may be disposed intermediate the first and second substrates 302. One or both of the substrates 302 and/or 304 may be non-continuous or have cut-outs so as to not extend fully about the belt portion 300. In an embodiment, portions of one of the substrates 302 or 304 may not be provided in some non-wearer contacting areas or other areas of the wearing-facing surface, and the elastic elements 306 may be attached to the remaining substrate 302 or 304 at least in those portions. In such an embodiment, the remaining full substrate 302 or 304 may be disposed on or form a portion of the garment-facing surface of the absorbent article 312.

Referring to FIGS. 10A-10F, the elastic elements 306 may be formed of any suitable materials as described above and may have any suitable cross-sectional shape, such as round, triangular, generally flat, rectangular or square, half-moon shaped, or ovate, for example. Those of skill in the art will recognize that other suitable cross-sectional shapes for the elastic elements 306 are also within the scope of the present disclosure. In various embodiments, the elastic elements 306 may vary in width and/or thickness about their length. In an embodiment, the dimensions (e.g., thickness, length, cross-sectional profile, width) of one elastic element 306 may be different than or the same as the dimensions of another elastic element 306 within the same belt portion. In an embodiment, the elastic elements 306 may comprise strips of an elastic film material, for example. In some embodiments, the elastic elements may have different pre-strain levels when attached to the substrates.

In general, referring again to FIG. 9, the elastic elements 306 may be linear and extend parallel to each other, or substantially linear and extend substantially parallel to each other, and may have equal or uniform, or substantially equal or uniform, distant spacing therebetween. For instance, distances D1, D2, D3, and D4 may all be equal or substantially equal (e.g., within 0.5-3.0 mm or 1.0-2.0 mm) to each other. Different texture zones having different textures, whether forming background or macro patterns, may be created even with equal, or substantially equal, spacing or distances between the elastic elements 306. In other embodiments, at least some of the distances D1, D2, D3, and D4 may be different than each other (i.e., non-uniform) within at least one texture zone, while other distances may be the same or substantially the same (i.e., uniform or substantially uniform) as each other. The spacing of the elastic elements 306 may be the same, substantially the same or different throughout all texture zones, as the texture zones are described herein. In an embodiment, some elastic elements 306 may be curved, such that at least some of the elastic elements 306 may be concentric with each other and have equal or substantially equal spacing therebetween. Alternatively, the elastic elements, whether curved or straight, may not be parallel to each other, and the spacing therebetween may not be uniform. In yet other embodiments, at least two of the elastics elements may intersect or overlap.

In related art belt portions, as the distance between the elastic elements decreases, the rugosity frequency increases and as the distance between the elastic elements increases, the rugosity frequency decreases. In the present disclosure, however, this is not necessarily true. In fact, the rugosity frequency may increase with the same distance or increasing the distance between the elastic elements or the rugosity frequency may decrease as the distance between the elastic elements decreases. Without being bound by any particular theory, it is believed that this occurs because the buckles or pleats formed in the rugosities are controlled, at least in part, by the amount and rigidity of the substrate(s) between the elastic members. The present disclosure provides for alteration of the local stiffness (e.g., densified regions) of a substrate or laminate of substrates to better define buckling or pleating points in interstitial areas between the elastic members, thereby controlling the resulting textures.

In addition to the belt portion 300, referring again to FIG. 11, a second belt portion 308 may be attached to, joined to, overlap with, and/or extend from the second end portion of the chassis 310 of the absorbent article 312. The second belt portion 308 is positioned across the lateral axis 303 from the first belt portion 300 and longitudinally opposes the first belt portion 300. The first belt portion 300 may form a portion of a first waist region while the second belt portion 308 may form a portion of a second waist region. The second belt portion 308 may be similar to or have at least the same features as the first belt portion 300. In other embodiments, the second belt portion 308 may be different than the first belt portion 300 (e.g., different size or texture zone locations). Each of the belt portions 300 or 308 may comprise a first side edge 314 and a laterally opposed second side edge 316. The first side edge 314 is positioned across the longitudinal axis 301 from the second side edge 316 and laterally opposes the second side edge 316. At least a portion of, or all of, the first side edge 314 of the belt portion 300, or the first belt portion 300, may be joined to at least a portion of, or all of, the first side edge 314 of the second belt portion 308. At least a portion of, or all of, the second side edge 316 of the first belt portion 300 may be joined to at least a portion of, or all of, the second side edge 316 of the second belt portion 308 to form a waist opening and two leg openings in the absorbent article 312. Instead of, or in addition to, the various side edges being joined to each other, side edge regions of the belt portions 300 and 308 proximate to the various side edges may be joined to each other to form a waist opening and two leg openings in the absorbent article 312. An example absorbent article having a waist opening and two leg openings is illustrated in FIG. 6. In an embodiment, this joining may be permanent to form a pant or a releasable or disengageable taped diaper. In an embodiment, the belt portion 300 may comprise a first waist opening edge 318 and the second belt portion 308 may comprise a longitudinally opposed second waist opening edge 320. The first waist opening edge 318 is positioned across the lateral axis 303 from the second waist opening edge 320. Each of the belt portions 300 and 308 may comprise a first leg opening edge 322 and a second, laterally opposed second leg opening edge 324. The first leg opening edges 322 are positioned across the longitudinal axis 301 from the second leg opening edges 324.

In an embodiment, the belt portions 300 and 308 and/or other elasticized portions of the absorbent articles disclosed herein may comprise texture zones forming background and macro patterns, single uniform or non-uniform textures, or other patterns therein. The texture zones forming the background and macro patterns, single uniform or non-uniform textures, or other patterns may be formed by the first substrate 302, the second substrate 304, and the elastic elements 306. In an embodiment, the texture zones may be formed by one of the substrates 302 or 304 and the elastic elements 306. As discussed above, the first substrate 302 and/or the second substrate 304 of the belt portions 300 and 308 may be portions of continuous materials, such as a nonwoven materials, that also cover central portions of the chassis 310 or may be separate layers of material covering a garment-facing and/or wearing-facing surface of the belt portions 300 and 308. In other embodiments, the first substrate 302 and the second substrate 304 may be a backsheet and a topsheet of an absorbent article 312, for example. In various embodiments, each absorbent article 312 and/or each belt portion 300 or 308 may comprise two or more texture zones, wherein the first texture zone forms a background pattern 334, and wherein the second texture zone forms a macro pattern 336. In other embodiments, the belt portions may only comprise a single uniform or non-uniform texture. A plurality of second texture zones may be provided to form a plurality of macro patterns or to create multiple macro pattern elements in one macro pattern. If more than two texture zones are provided, the additional texture zones may form other patterns in the absorbent article and/or in one or both of the belt portions. In an embodiment, the other patterns may be formed in or on the macro pattern 336 or in the background pattern 334. The absorbent articles may also comprise one or more non-texture zones "NT" (see e.g., FIGS. 11 and 12) in addition to the texture zones. In an embodiment, one or more of the macro patterns 336 or background patterns 334 may indicate, at least in part, to a wearer the appropriate orientation of the absorbent article about a lower torso of a wearer (see e.g., FIG. 13).

In an embodiment, a first texture zone forming a background pattern may comprise a first portion or area of the first and/or second substrates 302 and 304 and the elastic elements 306. A second texture zone forming a macro pattern may comprise a second portion or area of the first and/or second substrates 302 and 304 and the elastic elements 306. Furthermore, three or more other texture zones forming any suitable patterns in the belt portions may comprise a third portion or area or other portion or area of the first and/or second substrates 302 and 304 and the elastic elements 306. Stated another way, each texture zone formed in the absorbent article 312 may comprise a portion or area of at least one of the substrates and a portion of the elastic elements 306. The various texture zones may be located at any suitable location on the absorbent articles, such as on the belt portions or on other elasticized portions, for example. Some specific examples embodiments of texture zones forming background and macro patterns are provided below for illustration in various non-limiting embodiments.

In various embodiments, FIGS. 11-15, illustrate examples of absorbent articles 312 with texture zones or elasticized texture zones (hereinafter "texture zones") forming background patterns and macro patterns in belt portions 300 and 308. The garment-facing surface is facing towards the viewer in FIGS. 11-15, however it is to be understood that the texture zones forming the background and macro patterns may be viewable on one or both of the wearer-facing surface and the garment-facing surface and that the texture zones may be positioned in the same areas or different areas if the wearer-facing surface was facing toward the viewer. Although, the absorbent articles 312 are illustrated as pant diapers, it will be understood that the absorbent articles 312 may also be taped diapers and may comprise fastening components 326 on at least one belt portion (see e.g., FIG. 15). The various macro and background patterns may be suitable to receive or be attached to a fastening component. The various background and macro patterns formed by texture zones in FIGS. 11-15 are indicated by shading. The white portions (chassis 310 in FIGS. 11-15) may be non-texture zones for purposes of this disclosure. Non-texture zones are zones that are not texture zones and that generally do not have the "texture" with elastically extensible rugosities discussed in the present disclosure. While FIGS. 11-15 are merely examples of texture zones forming background and macro patterns, the present disclosure contemplates a plurality of configurations of texture zones forming background and macro patterns on belt portions. It is also within the scope of the present disclosure to have one belt portion or portions of one or both belt portions having non-texture zones.

In an embodiment, referring to FIG. 11, an absorbent article 312 may comprise a belt portion 300 having two different texture zones. The first texture zone may form a background pattern 334 in the belt portion 300 and the second texture zone may form a macro pattern 336 in the belt portion 300. The same background pattern 334 and macro pattern 336 may be formed on the second belt portion 308 as well (although not illustrated) or texture zones forming other background and macro patterns may be formed on the second belt portion 308. The macro pattern 336 may be formed of a plurality of discrete, linear or substantially linear elements. The discrete, linear elements may separate portions of the background pattern 334 from each other. Each of the discrete, linear elements may be surrounded by, or at least partially surrounded by, a portion of the background pattern 334. The macro pattern 336 may be formed in a different texture zone as the background pattern 334 owing to at least one of: (1) different primary fiber bond patterns in the substrates 302 and 304 in portions forming the macro pattern 336 and in portions forming the background pattern 334; (2) different adhesive patterns disposed between the substrates 302 and 304 in portions forming the macro pattern 336 and in portions forming the background pattern 334; (3) different adhesive attachment of the elastic elements 306 to the substrates 302 and 304 in portions forming the macro pattern 336 and in portions forming the background pattern 334; (4) different densified region patterns in the substrates 302 and 304 in portions forming the macro pattern 336 and in portions forming the background pattern 334, and (5) any combination of items 1-4. Other texture zones forming other patterns may also be provided in the belt portions 300 and 308.

Figure 12:
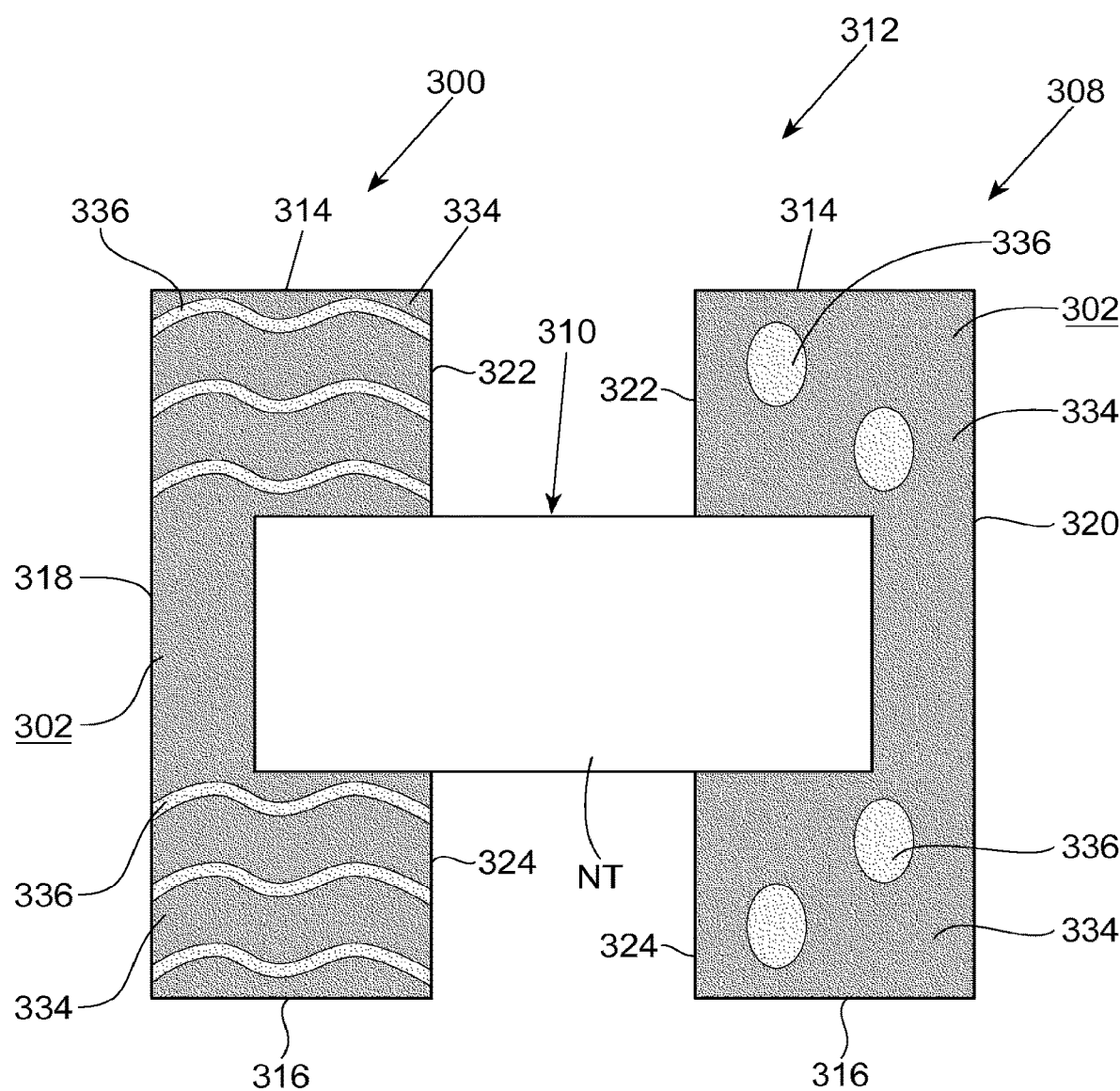

In an embodiment, referring to FIG. 12, an absorbent article 312 may comprise a belt portion 300 comprising two texture zones. The first texture zone may form a background pattern 334 in the belt portion 300 and the second texture zone may form a macro pattern 336 in the belt portion.

The macro pattern 336 may be formed of discrete, wavy lines or shapes, for example. The background pattern 334 may at least partially, or fully, surround the macro pattern 336, or portions thereof, and the macro pattern 334 may separate portions of the background pattern 334 from each other. The second belt portion 308 may also comprise two texture zones, at least one of which may be different than the two texture zones in the belt portion 300. The first texture zone may form a background pattern 334 in the belt portion 308 and the second texture zone may form a macro pattern 336 in the belt portion 308. The macro pattern 336 in the second belt portion 308 may be formed of ovals, for example, and may be surrounded by the background pattern 334. The various texture zones may be formed as discussed herein. In an embodiment, the macro patterns and/or the background patterns on the belt portions 300 and 308 may indicate the appropriate orientation of the absorbent article about a lower torso of a wearer. For example, the wavy line macro pattern 336 may be a front portion of the absorbent article 312, while the oval macro pattern 336 may be a back portion of the absorbent article 312. By providing such features, a caregiver can easily recognize how to appropriately don the absorbent article 312 on a lower torso of a child or other individual. Other texture zones forming other patterns may also be provided in the belt portions 300 and 308.

Figure 13:
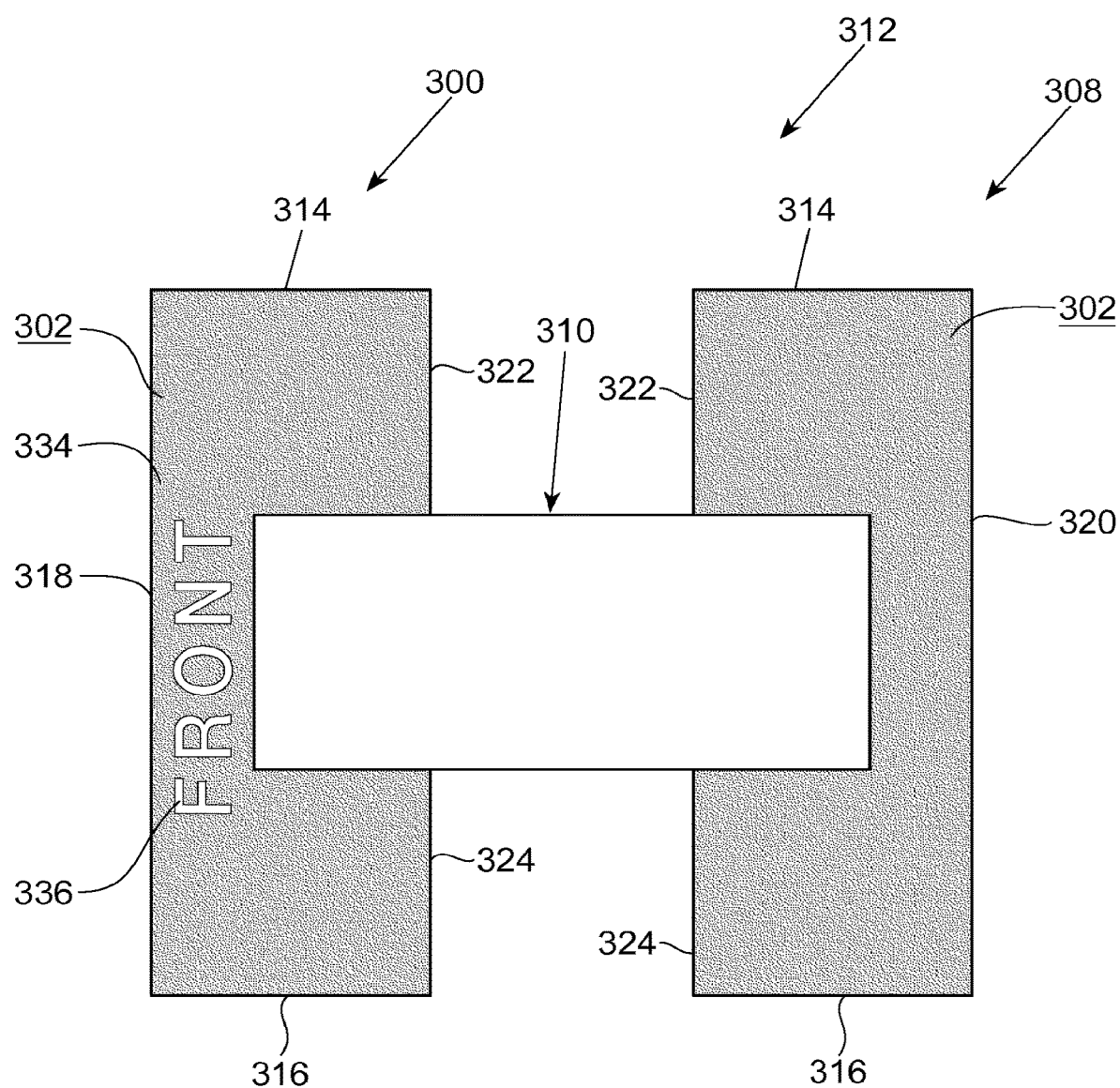

In an embodiment, referring to FIG. 13, an absorbent article 312 may comprise a belt portion 300 comprising two texture zones. The two texture zones may form a background pattern 334 and a macro pattern 336 in the belt portion 300. The macro pattern 336 may comprise indicia, logos, branding indicia, and/or text, such as the word "FRONT," for example. The word "FRONT" may indicate to a caregiver the appropriate orientation of the absorbent article 312 on a wearer. In an embodiment, although not illustrated, the second belt portion 308 may also comprise indicia, logos, branding indicia, and/or text, such as the word "BACK" or "REAR." The words "BACK" or "REAR" may indicate to a caregiver the appropriate orientation of the absorbent article 312 on a wearer. The two texture zones may be formed as discussed herein. Other texture zones forming other patterns may also be provided in the belt portions 300 and 308.

Figure 14:
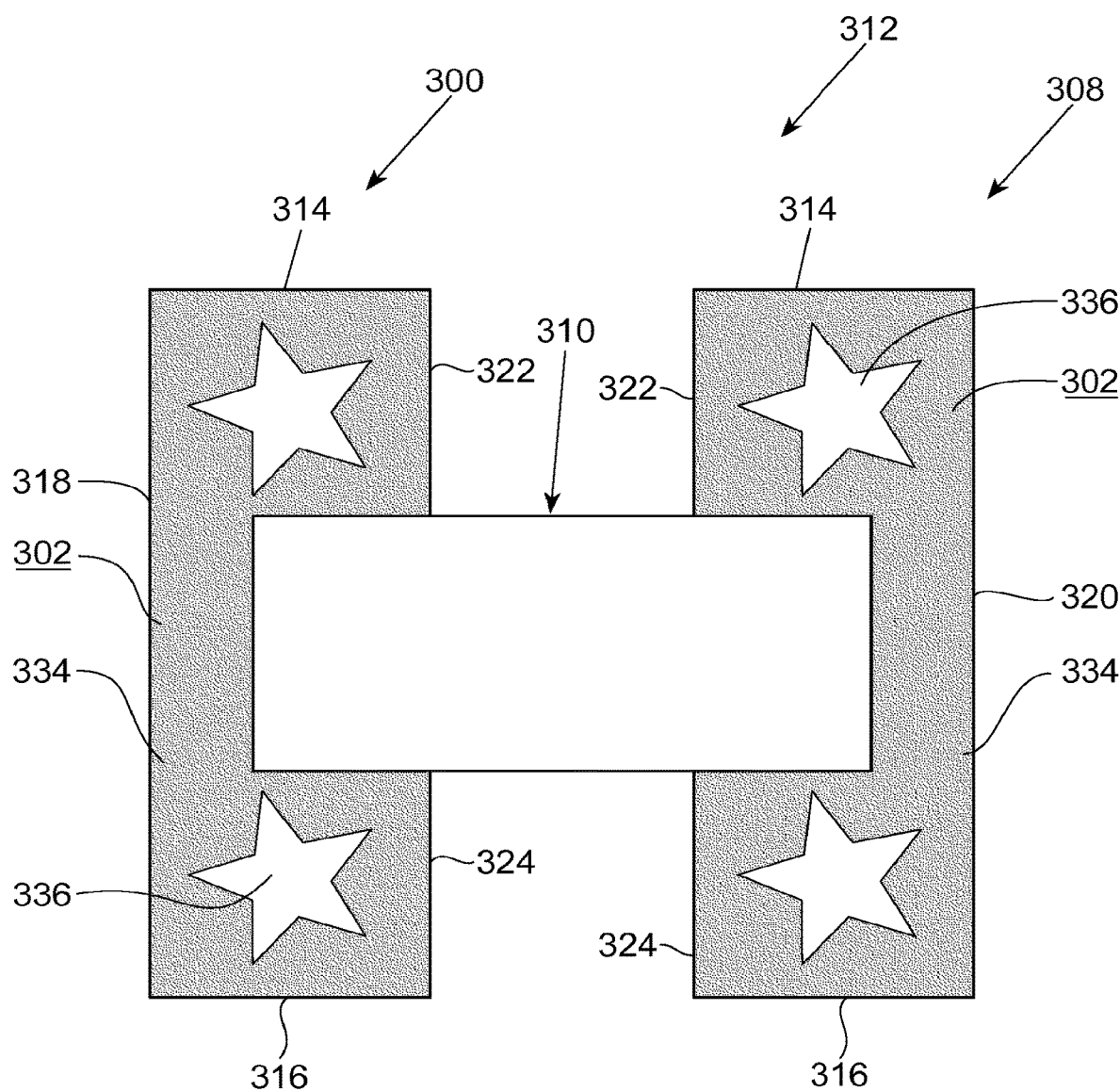

In an embodiment, referring to FIG. 14, an absorbent article 312 may comprise a belt portion 300 and a second belt portion 308. Each of the texture zones of the belt portions 300 and 308 may comprise a background pattern 334 and a macro pattern 336. The macro pattern 336 may comprise any suitable shapes, such as stars, for example. The macro pattern 336 may be fully or partially surrounded by the background pattern 334. In various embodiments, the macro pattern 336 and the background pattern 334 may be the same on the first belt portion 300 and the second belt portion 308. Other texture zones forming other patterns in the belt portions 300 and 308 may also be provided, such as other texture zones forming indicia, logos, branding indicia, or text, for example.

Figure 15:
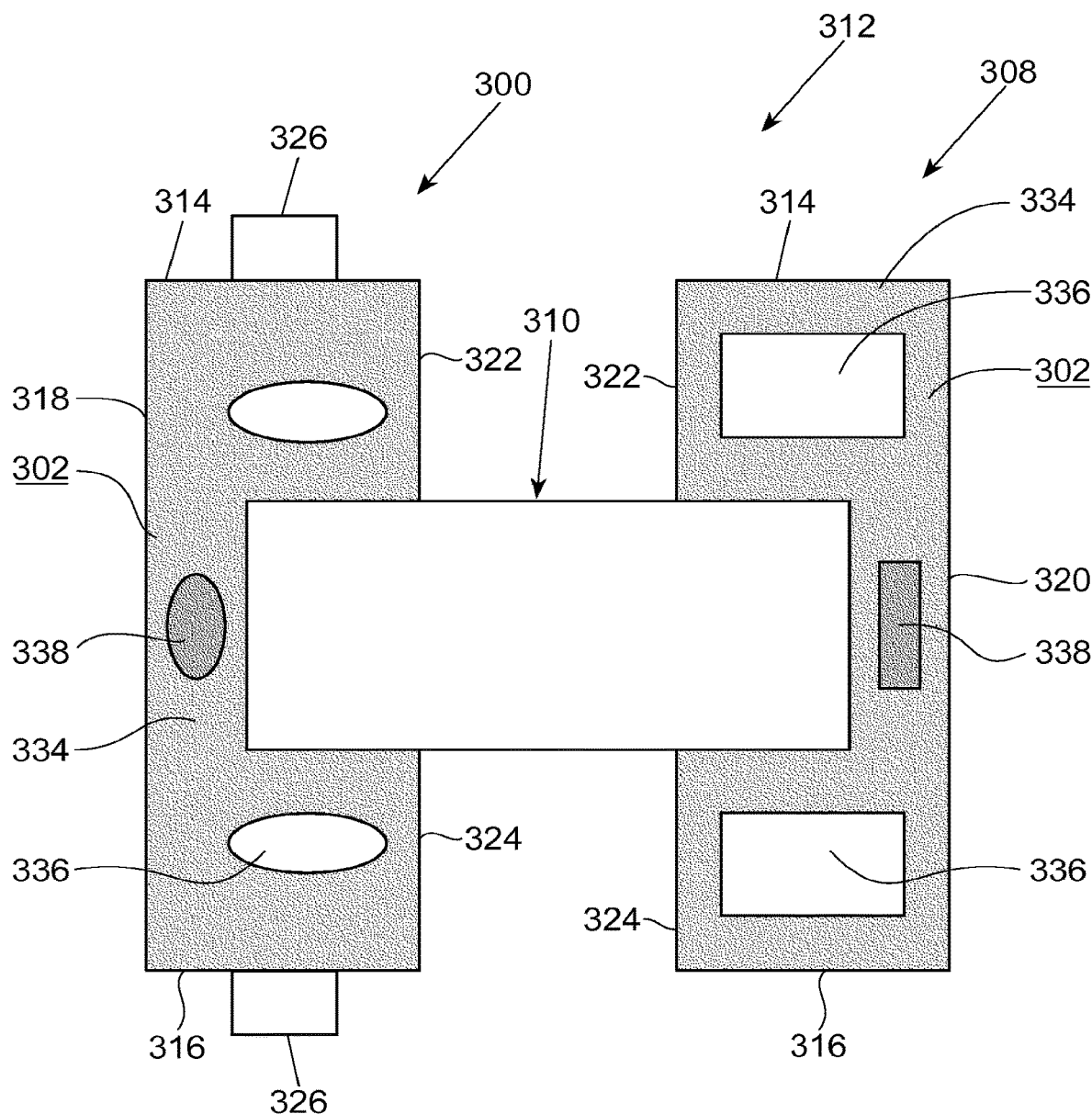

In an embodiment, referring to FIG. 15, an absorbent article 312 may comprise a belt portion 300 and a second belt portion 308. Each belt portion 300 and 308 may comprise three texture zones. The first texture zone may form a background pattern 334 in the belt portions 300 and 308. The second texture zone may form a first macro pattern 336 in the belt portions 300 and 308 and the third texture zone may form a second macro pattern 338 in the belt portions 300 and 308. The background pattern 334 in the belt portions 300 and 308 may be the same, substantially the same, or different. Likewise, the first macro pattern 336 in the belt portions 300 and 308 may be the same, substantially the same, or different. If they are different, they may form different shapes and may have different areas, for example. In the example embodiment illustrated, the first macro pattern 336 in the first belt portion 300 forms a different shape and has a different area than the first macro pattern 336 in the second belt portion 308. Also, the second macro pattern 338 in the first belt portion 300 may form a different shape and may have a different area than the second macro pattern 338 in the second belt portion 308. Other configurations of macro patterns and additional macro patterns are within the scope of the present disclosure.

The various macro patterns and background patterns referenced herein may extend over all of or a portion of the area of the belt portions 300 or 308. In an embodiment, the background patterns may form a grid-like structure (see e.g., FIG. 16) and the macro patterns may form discrete elements positioned between the grid-like structure. The macro patterns and/or the background patterns may extend from a first side edge 314 to a second side edge 314, or partially between the same. Likewise, the macro patterns and/or the background patterns may extend from a waist opening edge 318 or 320 to a leg opening edge 322 or 324, or partially between the same. In an embodiment, the macro pattern and the background pattern may alternate about one or more of the belt portions 300 and 308. For example, in the direction between the first side edge 314 and the second side edge 316 or in the direction between the waist opening edge 318 and/or 320 and the leg opening edges 322 and/or 324, the pattern may be background pattern, macro pattern, background pattern, macro pattern, and so forth. In an embodiment, the background pattern may form an outer portion or border of the belt portions 300 and 308 and the macro pattern may form the area surrounded by the outer portion or border or vice versa. Other configurations of background and macro patterns on belt portions are contemplated by the present disclosure.

Figure 16:
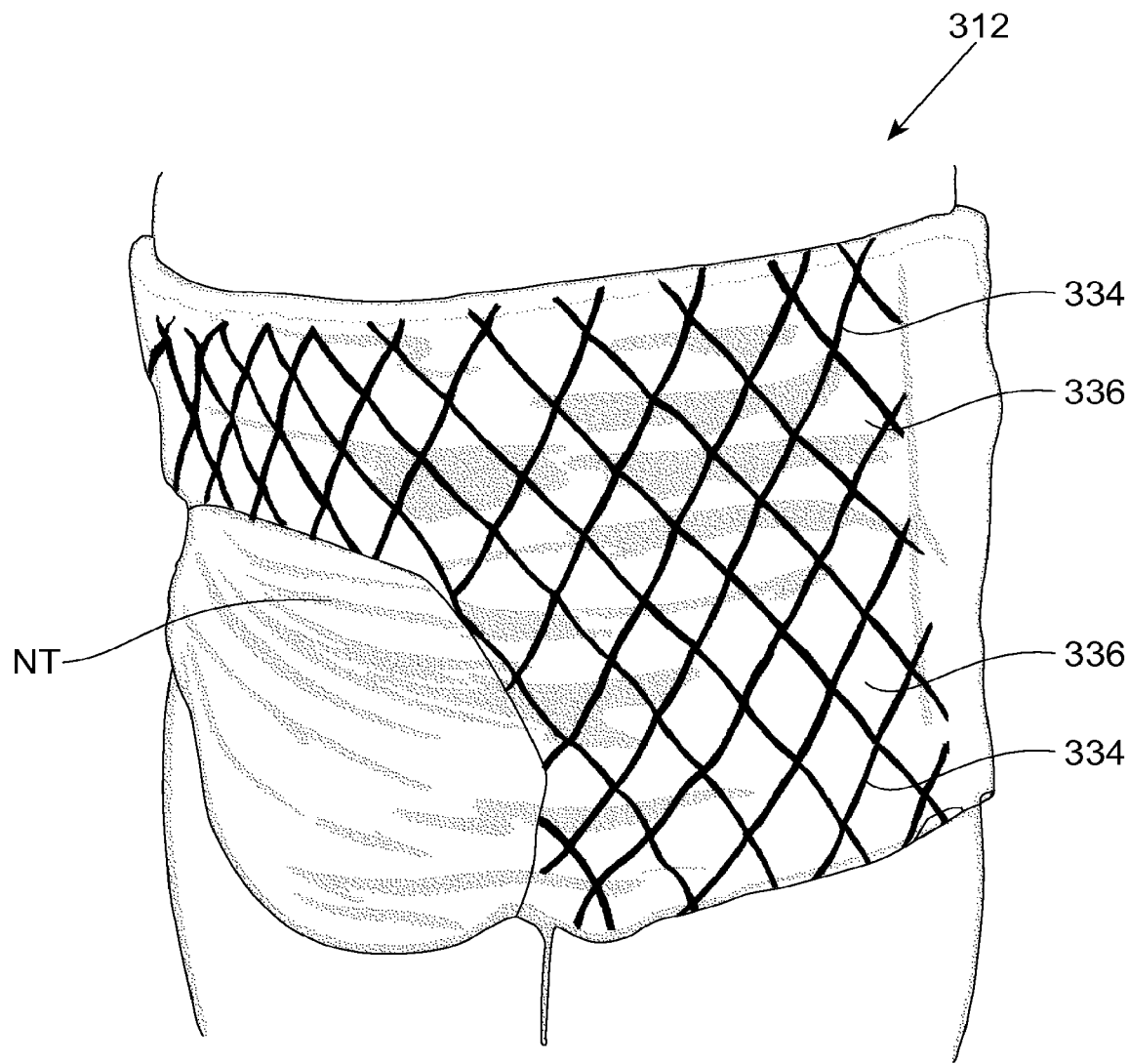
FIGS. 16-18 are illustrations of absorbent articles with belt portions comprising texture zones, forming background patterns and macro patterns, and non-texture zones in accordance with various non-limiting embodiments.
Figure 17:
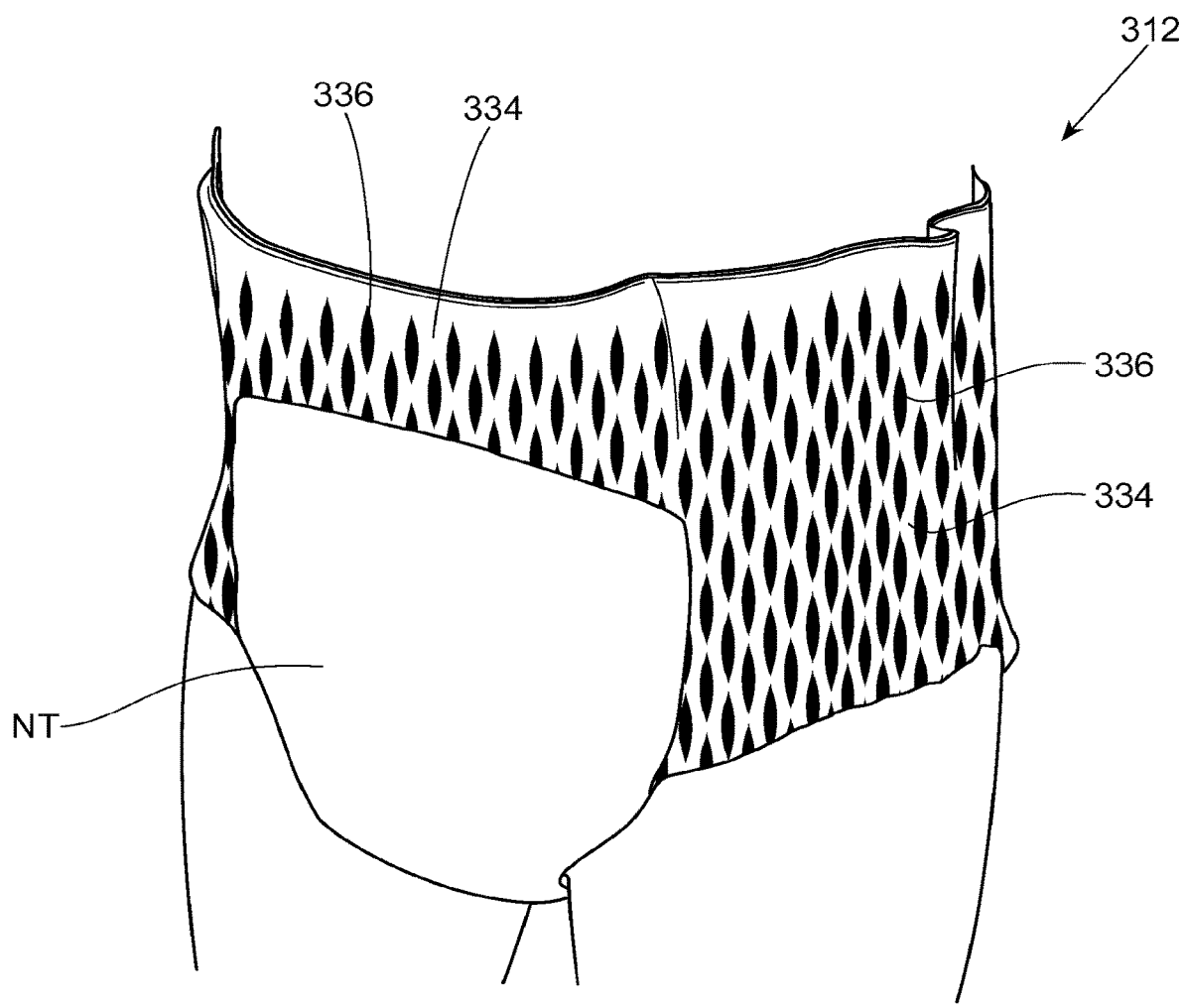
Figure 18:
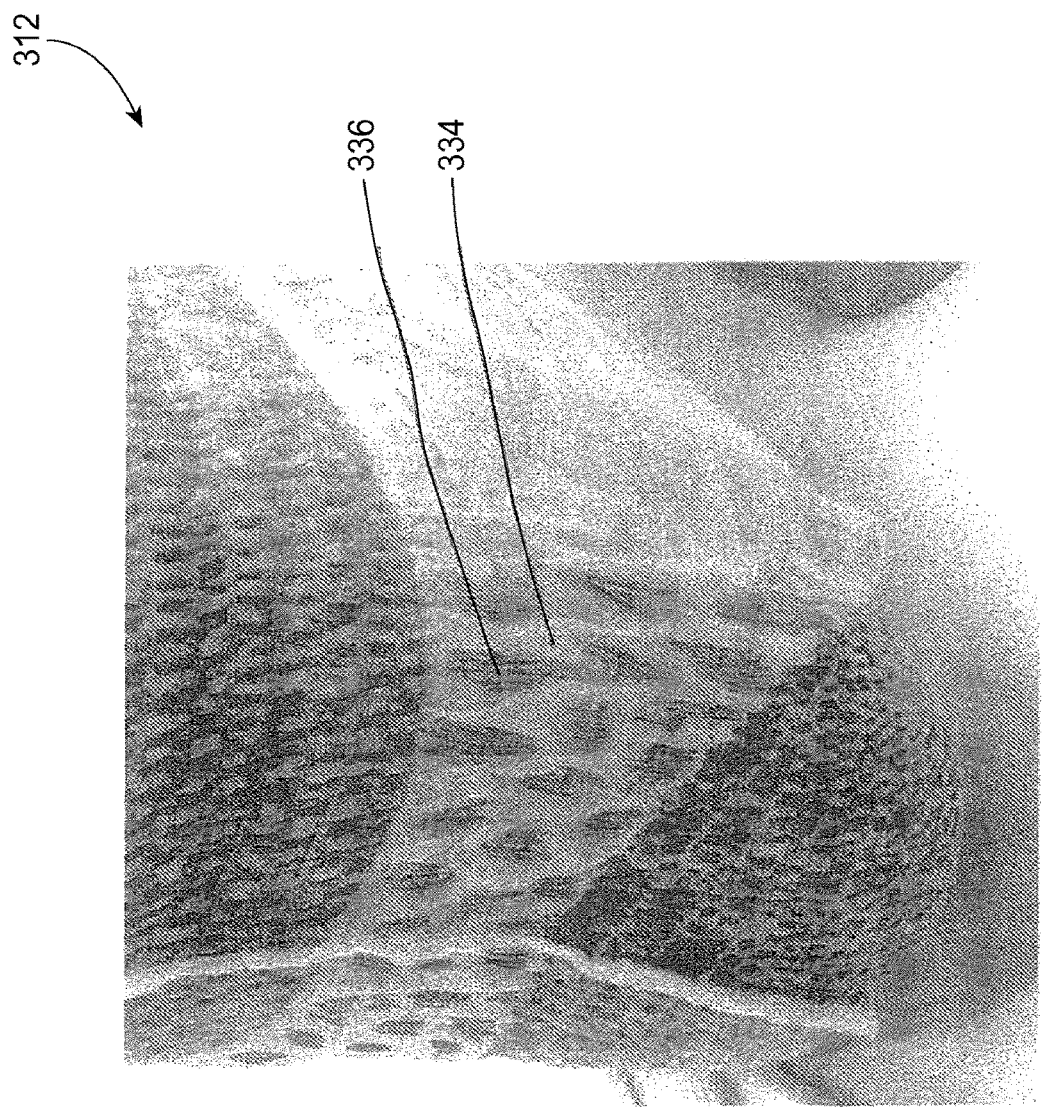

Some example appearances of the texture zones forming background patterns 334 and macro patterns 336 of the present disclosure on absorbent articles 312 are illustrated in FIGS. 16-18. As can be seen, in various embodiments, the texture zones forming background patterns 334 and macro patterns 336 may extend about a waist opening and about leg openings of the absorbent article 312. Of course, the texture zones may also extend through any other areas, belted portions, or other portions of the absorbent articles 312 with elastic elements disposed on at least one, and possibly between two, substrates. In various embodiments, as illustrated in some of the figures, printing, outlining, painting, dying, tinting, and/or other techniques may also be used to enhance the visibility of the various texture zones.

Figure 19:
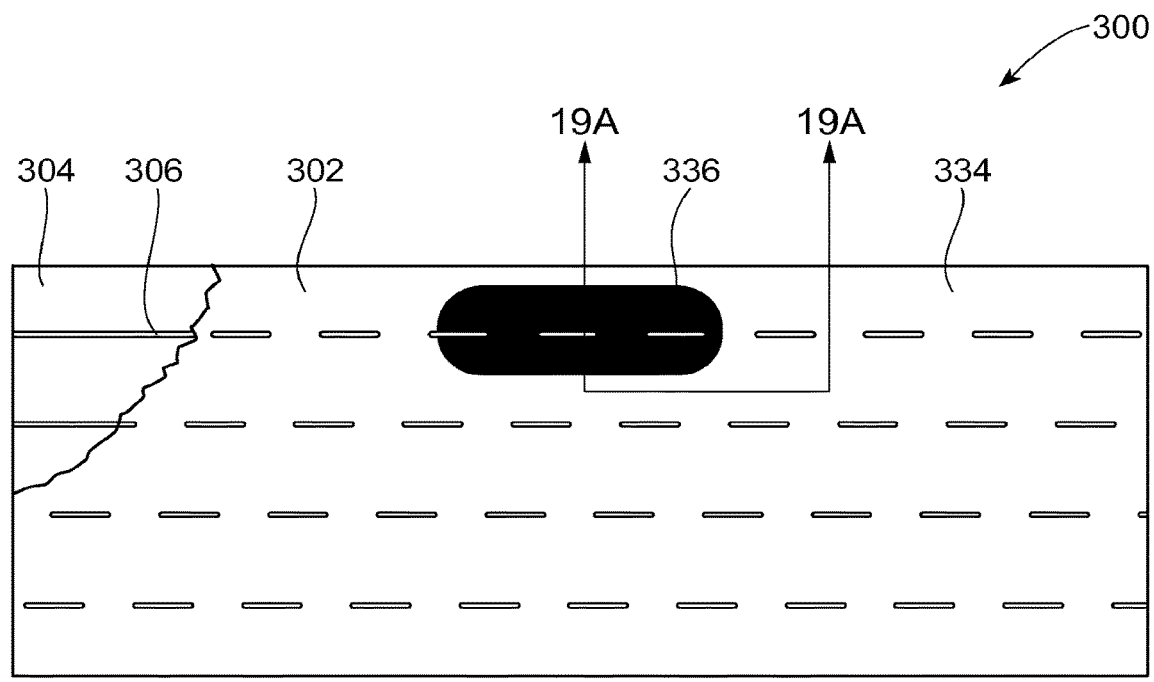
FIG. 19 is a partially cut away plan view of a belt portion comprising two texture zones in accordance with one non-limiting embodiment.

In an embodiment, referring to FIG. 19, another example belt portion 300 for an absorbent article is illustrated. The absorbent article comprises texture zones forming a background pattern 334 and a macro pattern 336 therein. The background pattern 334 has a different texture as the macro pattern 336. The belt portion 300 comprises a first substrate 302, a second substrate 304, and a plurality of elastic elements 306 disposed intermediate the first and second substrates 302 and 304.

Figure 19A:
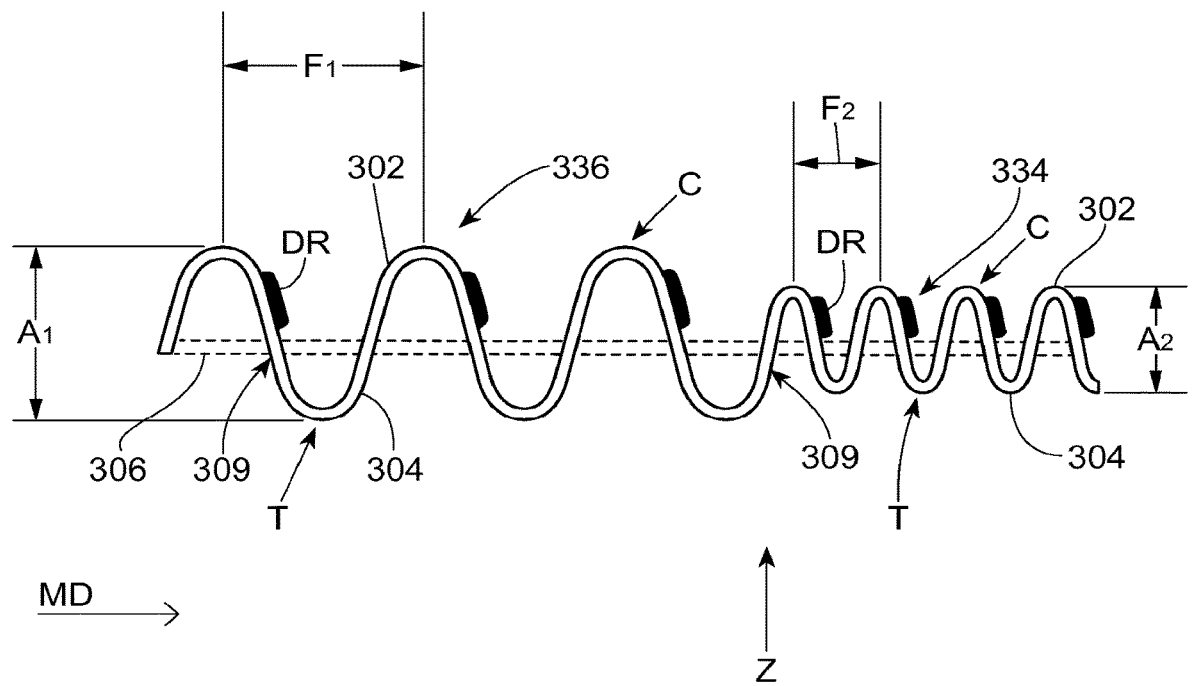
FIG. 19A is an example cross-sectional view of the two texture zones of FIG. 19 taken about line 19A-19A in accordance with one non-limiting embodiment.

In an embodiment, referring to FIG. 19A, an example cross-section taken about line 19A-19A of FIG. 19 is illustrated. FIG. 19A illustrates the macro pattern 336 and the background pattern 334. The macro pattern 336 has a first rugosity frequency or rugosity frequency range F1 and a first rugosity amplitude or rugosity amplitude range A1 and the background pattern 334 has a second rugosity frequency or second rugosity frequency range F2 and a second rugosity amplitude or rugosity amplitude range A2. The first rugosity frequency F1 is different than the second rugosity frequency F2 and, likewise the first rugosity amplitude A1 is different than the second rugosity amplitude A2. It is to be understood that each rugosity within a particular macro or background pattern may not have exactly the same frequency or amplitude, as such frequency and amplitude ranges of rugosities may be formed in a specific macro and background patterns. The rugosity frequency and rugosity amplitude ranges in a particular macro or background pattern may be different than, the same as, or at least partially overlap the rugosity frequency and rugosity amplitude ranges in one or more other macro or background patterns in the same absorbent article. Densified regions "DR" are illustrated in FIG. 19A. The densified regions in a substrate may have a thickness that is less than about ⅓ of the thickness of the non-densified areas of the substrate, for example. The dimensions of the densified regions DR in the macro pattern 336 may be different than the dimensions of the densified regions DR in the background pattern 334. The elastic elements 306 are in their relaxed state in FIG. 19A.

In an embodiment, a first substrate of a belt portion may comprise a nonwoven material comprising a plurality of densified regions. The belt portion may also comprise a second substrate that may comprise a nonwoven material and may comprise a plurality of densified regions or may be free of the plurality of densified regions. The first substrate and/or the second substrate may have a rugosity frequency of greater than about 7, 7, about 8, 8, about 9, or 9 and less than about 25 rugosities per centimeter. The plurality of densified regions in the first and/or second substrates may define the rugosity frequency of one or more texture zones formed in the first and/or second substrates. The various densified regions may be continuous and/or discontinuous. A substrate may have densified regions that are continuous and densified regions that are discontinuous. The belt portions may also comprise elastic elements disposed at least partially intermediate the first and second substrates.

In an embodiment, a substrate of a belt portion may comprise a laminate comprising two layers or materials joined together by a primary fiber bonds and/or a densified regions that define a rugosity frequency of a texture zone of the belt portion.

In an embodiment, referring to FIG. 19A, the rugosities in a texture zone may be described by a sinusoidal shape. Each rugosity may be described to have a crest, C, at its highest point and a trough, T, at its lowest point. The rugosity length is defined by the linear distance in the machine direction, MD, between two adjacent crests and is determined as described below in the Rugosity Length, Rugosity Frequency, Rugosity Amplitude, Elastic Element Spacing, and Texture Ratio Method. The rugosity amplitude is defined by the linear distance in the "Z" direction between an adjacent crest, C, and a trough, T and is determined as described below in the Rugosity Length, Rugosity Frequency, Rugosity Amplitude, Elastic Element Spacing, and Texture Ratio Method. The rugosity frequency is described by rugosity length per a unit length, resulting as the number of rugosities per cm.

Suitable rugosity frequencies used to create macro and background patterns or other texture zones, such as single uniform texture zones, may range from about 0.1 rugosities per cm to about 50 rugosities per cm, alternatively, about 0.5 rugosities per cm to about 25 rugosities per cm, alternatively, about 1 rugosity per cm to about 10 rugosities per cm, and alternatively, about 5 rugosities per cm to about 10 rugosities per cm, specifically reciting all 0.1 rugosity per cm increments within the above-recited ranges and all ranges formed therein or thereby. Suitable rugosity amplitudes may be in the range of about 0.25 mm to about 15 mm, alternatively about 0.5 mm to about 10 mm, and alternatively, about 1 mm to about 5 mm, specifically reciting all 0.1 mm increments within those ranges and all ranges formed therein or thereby.

The elastic element spacing may be measured according to the Rugosity Length, Rugosity Frequency, Rugosity Amplitude, Elastic Element Spacing, and Texture Ratio Method described below. Example elastic element spacing may be in the range of about 2 mm to about 20 mm, about 4 mm to about 18 mm, about 4 mm to about 15 mm, about 5 mm to about 15 mm, about 6 mm to about 15 mm, greater than 4 mm and less than 15 mm, about 4 mm, about 5 mm, about 6 mm, about 7 mm, about 8 mm, about 9 mm, or about 10 mm, specifically reciting all 0.5 mm increments within the specified ranges and all ranges formed therein or thereby. These elastic elements may be uniformly spaced or non-uniformly spaced relative to each other in various embodiments. In an embodiment of a belt portion, the elastics elements may be uniformly spaced in portions and non-uniformly spaced in other portions. The elastic elements may be straight or may be curvilinear.

The various belt portions of the absorbent articles of the present disclosure may have one or more texture zones having texture ratios. The texture zones may be uniform or non-uniform. The texture ratios are determined by the Rugosity Length, Rugosity Frequency, Rugosity Amplitude, Elastic Element Spacing, and Texture Ratio Method described below. Some example texture ratios may be about 2 to about 35 (units—Average Elastic Element Spacing(cm)/ Average Rugosity Length (cm)) or about 4 to about 30. A higher texture ratio enables a slimmer fitting product at a lower cost and increased comfort of the wearer in addition to the other advantages described herein. As such, some ranges of texture ratios are about 4 to about 25, about 4.5 to about 25, about 5 to about 25, about 5 to about 20, about 5.5 to about 20, about 6 to about 20, about 7 to about 20, above about 4, above about 5, above about 5.5, above about 6, or above about 7, specifically reciting all 0.1 increments within the ranges specified in this paragraph and all ranges formed therein or thereby.

Figure 20A:
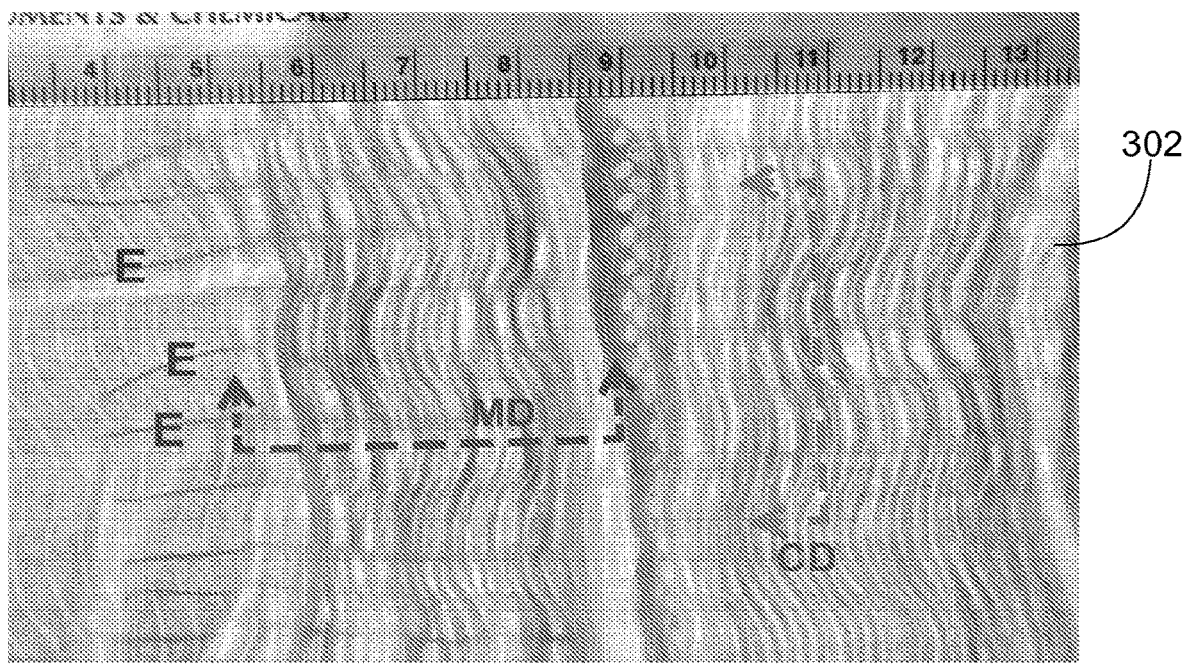
FIG. 20A is a perspective view of an example texture zone in an absorbent article in accordance with one non-limiting embodiment.
Figure 20B:
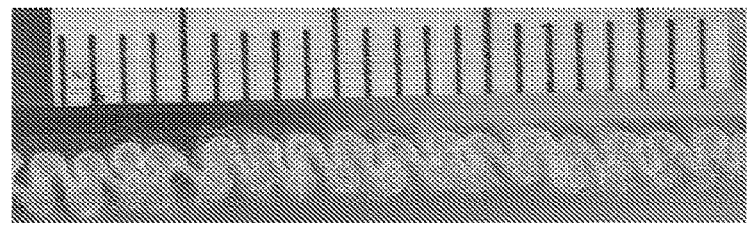
FIG. 20B is a cross-sectional view of the texture zone of FIG. 20A taken about line MD using a first order of magnification in accordance with one non-limiting embodiment.
Figure 20C:
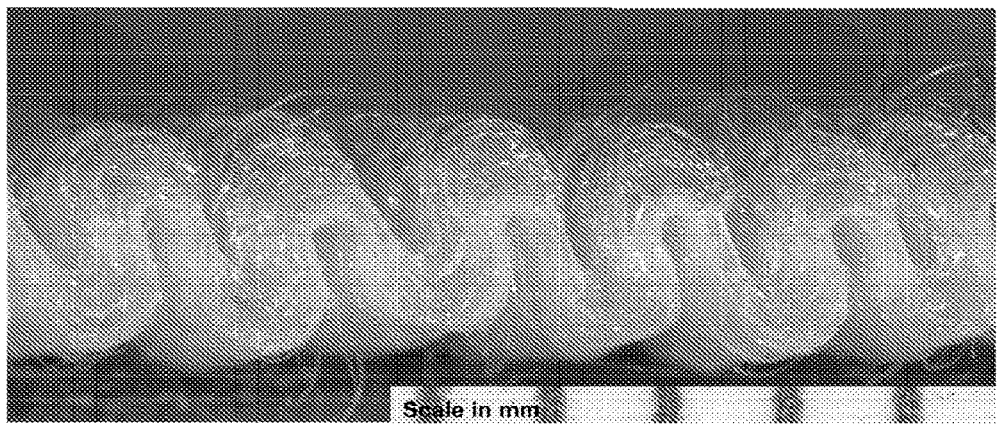
FIG. 20C is a cross-sectional view of the texture zone of FIG. 20A taken about line MD using a second order of magnification in accordance with one non-limiting embodiment.
Figure 20D:
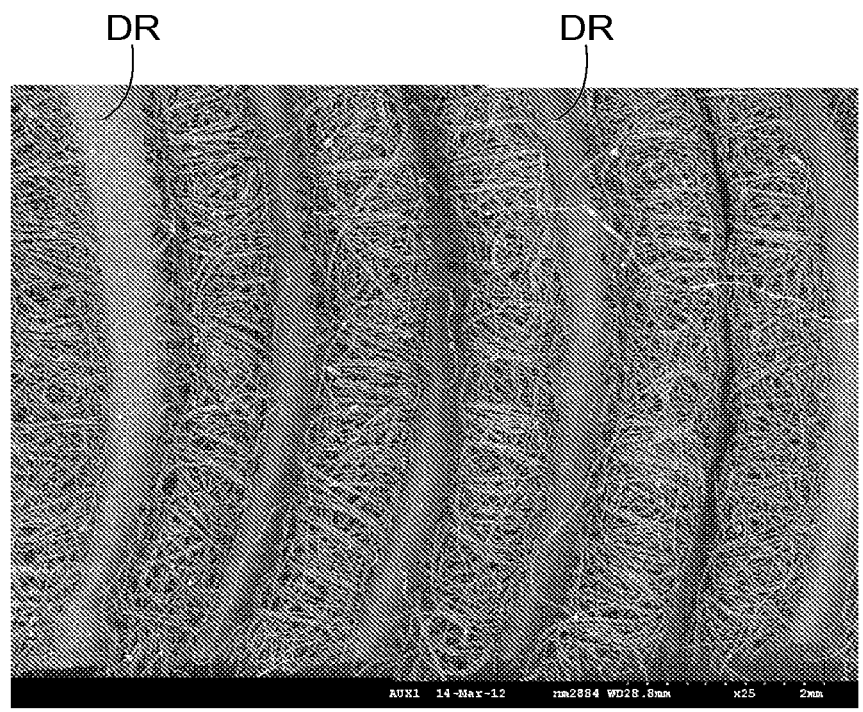
FIG. 20D is a perspective view of a portion of the texture zone of FIG. 20A about line MD in accordance with one non-limiting embodiment.
Figure 20E:
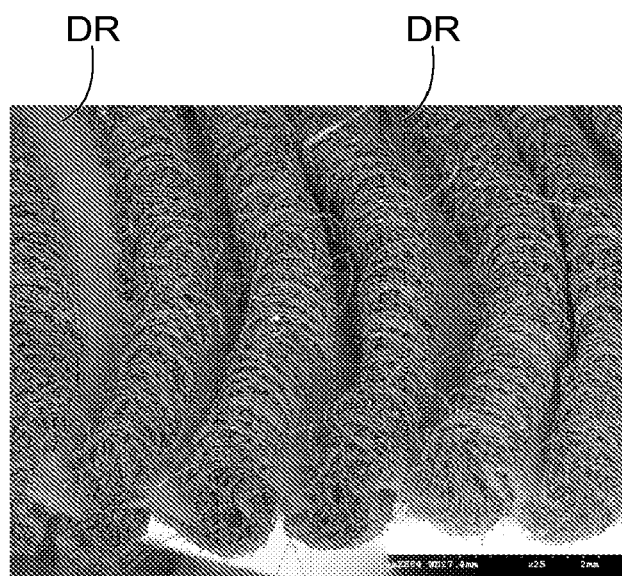
FIG. 20E is another perspective view of a portion of the texture zone of FIG. 20A about line MD in accordance with one non-limiting embodiment.
Figure 20F:
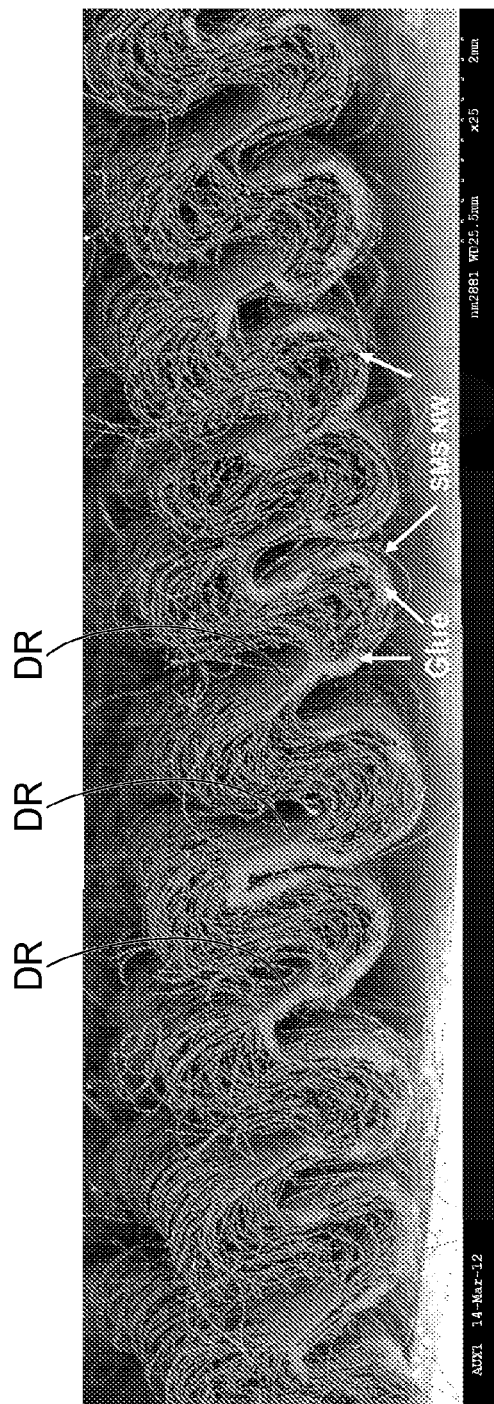
FIG. 20F is a cross-sectional view of the texture zone of FIG. 20A taken about line MD using a third order of magnification in accordance with one non-limiting embodiment.

FIG. 20A illustrates an example texture zone having a plurality of rugosities under magnification on an absorbent article. The scale shown in FIG. 20A is in centimeters. The example texture zone illustrates a macro pattern or a background pattern. Either pattern may have similar characteristics and structural properties, only the rugosity frequency and rugosity amplitude, or ranges thereof, may change. The elastic elements are indicated as "E" in FIG. 20A. MD is the machine direction and CD is the cross-direction, as explained in further detail herein. The first substrate 302 is facing the viewer in FIG. 20A. FIG. 20B is a cross-sectional view taken about line MD of FIG. 20A using a first order of magnification, while FIG. 20C is a cross-sectional view taken about line MD of FIG. 20A using a second order of magnification. The second order of magnification is greater than the first order of magnification. FIGS. 20B and 20C illustrate the rugosities in the texture zone. FIGS. 20D and 20E are perspective views of a portion of the texture zone of FIG. 20A taken about line MD. FIG. 20F is a cross-sectional view taken about line MD of FIG. 20A using a third order of magnification. The densified regions are indicated as DR in FIGS. 20D-20F. In FIGS. 20A-20F, the elastic elements E are in their relaxed state.

Figure 21A:
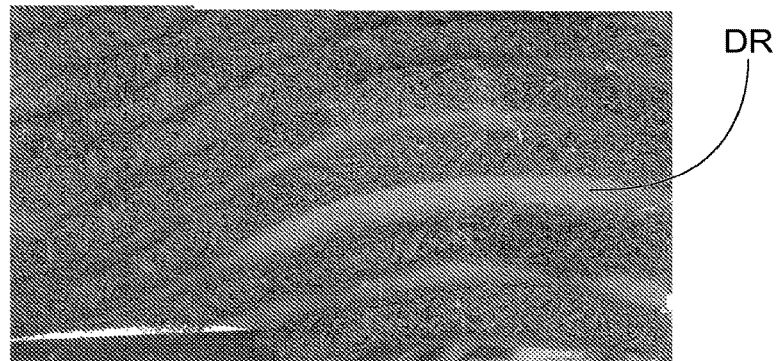
FIG. 21A is a perspective view of a portion of the texture zone of FIG. 20A about line CD in accordance with one non-limiting embodiment.
Figure 21B:
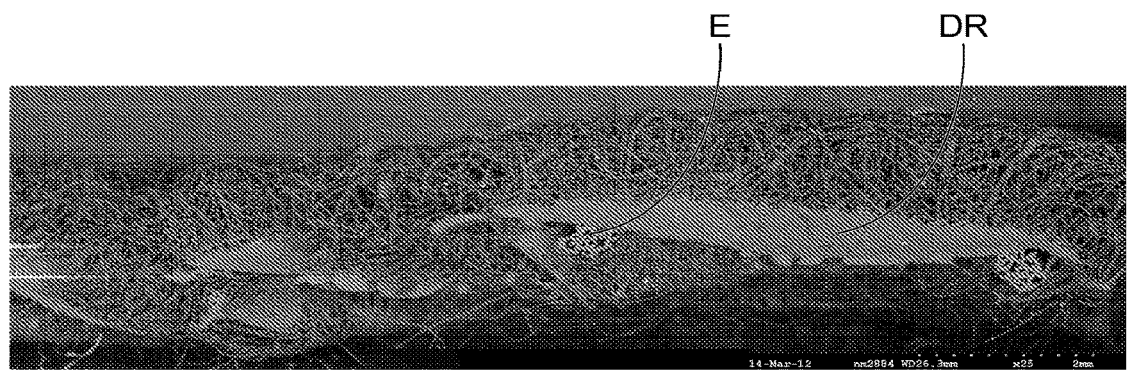
FIGS. 21B and 21C are cross-sectional views of the texture zone of FIG. 20A taken about line CD using a first order of magnification in accordance with various non-limiting embodiments.
Figure 21C:
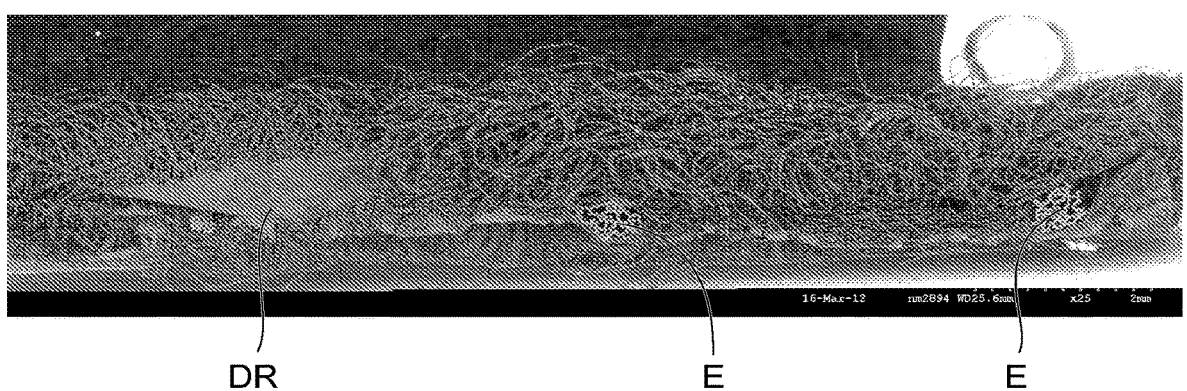
Figure 21D:
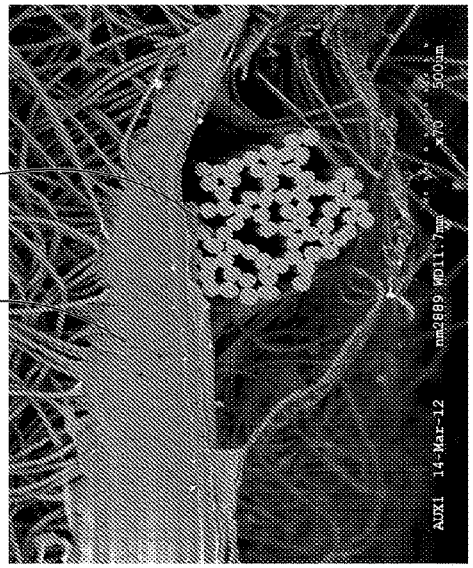
FIGS. 21D-21G are cross sectional views of the texture zone of FIG. 20A taken about line CD using a second order of magnification in accordance with various non-limiting embodiments.
Figure 21F:
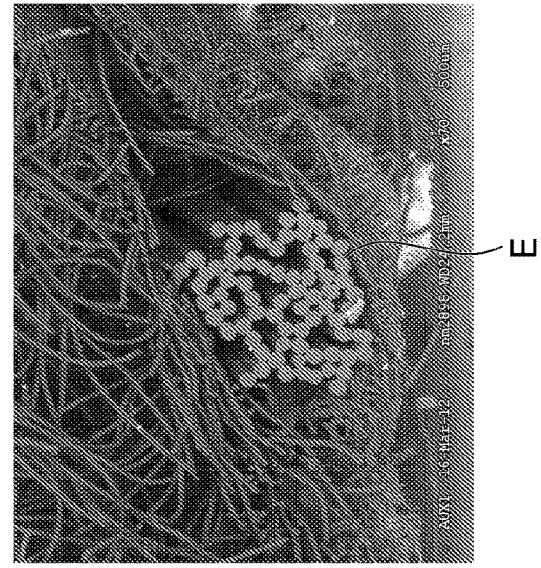
Figure 21E:
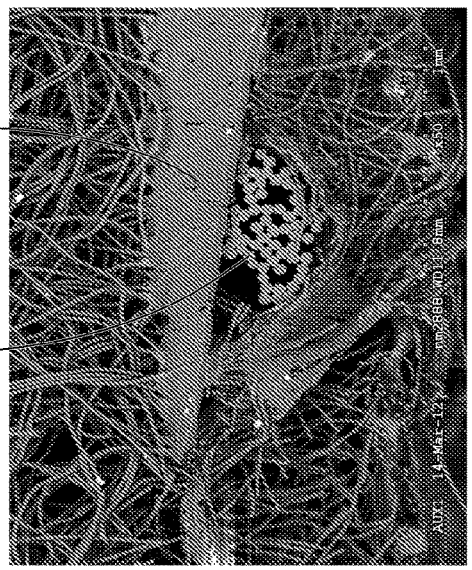
Figure 21G:
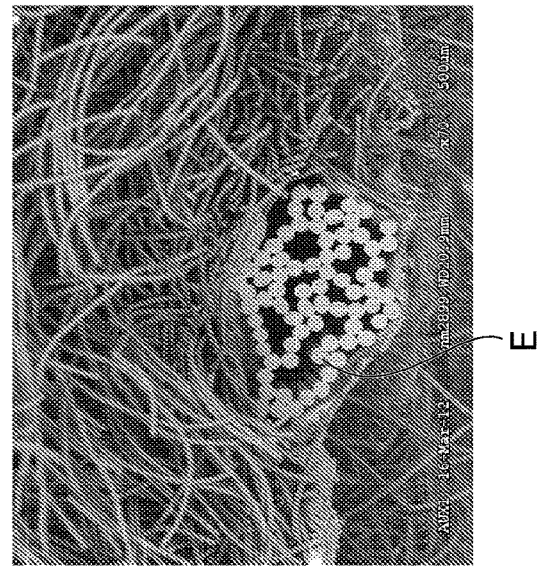

FIG. 21A is a top perspective view of the texture zone of FIG. 20A taken about line CD illustrating the rugosities and the densified regions, DR. FIGS. 21B and 21C are cross-sectional views of FIG. 20A taken about line CD using a first order of magnification. FIGS. 21D and 21F are cross-sectional views of FIG. 20A taken about a portion of line CD using a second order of magnification. FIGS. 21E and 21G are additional cross-sectional view of FIG. 20A taken about a portion of line CD using the second order of magnification. The elastic elements "E" are illustrated in FIGS. 21B-21G in their relaxed state. The densified regions DR or densified region patterns of FIGS. 20A-21G may be formed using the pattern of densified regions illustrated in FIG. 24.

In an embodiment, referring again to FIGS. 19 and 19A, within the background pattern 334 and the macro pattern 336 a rugosity frequency and/or a rugosity amplitude range in the first substrate 302 and the second substrate 304 may be different. For example, larger rugosity frequencies or rugosity amplitudes, or ranges thereof, may be provided on the substrate on the garment-facing surface to connote stretch and smaller rugosity frequencies or rugosity amplitudes, or ranges thereof, may be provided on the substrate on the wearer-facing surface to create a smoother surface on the skin of a wearer to prevent, or at least inhibit, skin markings associated with the rugosities. The "rugosities" are formed by the pleats or folds in the first and second substrates 302 and 304 when the elastic elements 306 are contracted into a relaxed, or partially relaxed, state. The first and second substrates 302 and 304 may be bonded to or adhesively attached (e.g., using glue) to the elastic elements 306 at bond sites 309. In some embodiments, the first and second substrates, or portions thereof, may also be bonded directly to each other. The elastic elements 306 in FIGS. 19 and 19A are shown in their relaxed or contracted state. If the elastic elements 306 where partially elongated in the directions of arrow A, the rugosities in the first and second substrates 302 and 304 would begin to flatten (i.e., reduce in rugosity amplitude). If the elastic elements 306 where fully elongated, or mostly elongated, in the directions of arrow A, the first and second substrates 302 and 304 may be generally flat or substantially flat. As such, to form the rugosities in the first and second substrates 302 and 304, the elastic elements 306 are attached to one or both of the first and second substrates 302 and 304 in their expanded or prestrained state and then allowed to contract into a state of lower energy.

In an embodiment, the rugosity of one texture zone (whether forming a background pattern or a macro pattern) may be the same as or different than the rugosity of at least one other texture zone (whether forming a background pattern or a macro pattern) in a belt portion. In other embodiments, the rugosity of one texture zone may be the same as or different than the rugosity in all of the other texture zones in a belt portion or in an absorbent article (e.g., two belt portions). A rugosity in a first texture zone may have a first range of amplitudes and/or a first range of frequencies and a rugosity in a second texture zone may have a second range of amplitudes and/or a second range of frequencies. The ranges of amplitudes in two or more of the texture zones may overlap, not overlap, be the same, or be different. Likewise, the ranges of frequencies in two or more of the texture zones may overlap, not overlap, be the same, or be different. In other embodiments, the shapes of the rugosities may impact the texture appearance by being angular, trapezoidal, asymmetric, round, triangular, or any other suitable geometric form. In still other embodiments, the rugosities may have the same, or a very similar, frequencies, but may have different shapes (e.g., triangular, rounded, trapezoidal).

As described herein, the various texture zones (whether forming a background or macro pattern or a single texture zone) may be formed in a belt portion comprising a first substrate, a second substrate, and a plurality of elastic elements disposed therebetween. The first substrate may be attached to the second substrate and/or to at least some of the elastic elements. In other embodiments, the first and second substrates may be attached to each other and/or to the elastic elements. In any event, the elastic elements may be attached to at least one of the substrates. In an embodiment, the elastic elements may cause a first rugosity to be created in the first substrate and a second, different rugosity to be created in the second substrate in the same area of a belt portion but on opposing surfaces of the belt portion. This type of texturing may be caused by the primary fiber bond patterns or other larger bond patterns (i.e., densified regions) in each of the first substrate and the second substrate. In such an embodiment, the first substrate may have a different primary fiber bond pattern than the second substrate. In various embodiments, the bond areas in a first primary fiber bond pattern of a first substrate may be larger or smaller when compared to the bond areas in a second primary fiber bond pattern of a second substrate.

In an embodiment, referring again to FIG. 11, the absorbent article 312 may comprise the chassis 310, the first belt portion 300 extending from a first end portion of the chassis 310, and the second belt portion 308 extending from a second end portion of the chassis 310. FIG. 11 is oriented such that a garment-facing surface is directed toward the viewer. The chassis 310 may overlap a portion of the first belt portion 300 and/or the second belt portion 308 such that a backsheet 330 of the chassis 310 may form a portion of the garment-facing surface. Stated another way, the belt portions 300 and 308 may be in a face-to-face relationship with a topsheet 332 of the chassis 310. The chassis 310 may also comprise an absorbent core 350 positioned between at least a portion of the topsheet 332 and the backsheet 330, as described in greater detail above. In an embodiment, the belt portions 300 and 308 may comprise a first texture zone forming a background pattern 334, a second texture zone forming a macro pattern 336, and optionally one or more other texture zones. The first texture zone form the background pattern 334 may have a different texture as the backsheet 330 and a different or the same texture as the second texture zone forming the macro pattern 336. In an embodiment, the first texture zone may have a first range of rugosities, the second texture zone may have a second range of rugosities, and the backsheet's texture may be substantially flat (i.e., does not have a rugosity). The backsheet 330 may be one example of a "non-texture zone." In other embodiments, the backsheet 330, or portions thereof, may have a range of rugosities that is the same as or different than the range of rugosities in one or both of the first and second texture zones. If the belt portions 300 and 308 are in a face-to-face relationship with the backsheet 330, then the topsheet 332 may have similar features as the backsheet 330 discussed above. In other embodiments, the elastic elements 306 in the belt portions 300 and 308 may not be "activated" by not bonding elastic elements to the substrate(s) in some areas and cutting or breaking the elastic elements 306, thereby creating additional "non-texture zones." In an embodiment, this non-activated zone may occur over an area or portion of the area of the absorbent core 350, for example.

In an embodiment, referring to FIGS. 9 and 11, the absorbent article 312 may comprise a first belt portion 300 and a second belt portion 308. The first belt portion 300 may comprise a first substrate 302, a second substrate 304 joined to at least a portion of the first substrate 302, and a plurality of elongate elastic elements or strands 306 disposed at least partially intermediate the first substrate 302 and the second substrate 304. The second belt portion 308 may comprise a third substrate and a fourth substrate (similar to or the same as the substrates 302 and 304). The fourth substrate may be joined to at least a portion of the third substrate. The second belt portion 308 may comprise a plurality of elongate elastic elements or strands disposed at least partially intermediate the third substrate and the fourth substrate. The first and second belt portions 300 and 308 may each have a texture zone having a texture ratio of greater than 5 and less than 25 or greater than 5, specifically reciting all 0.5 mm increments within the specified ranges and all ranges formed therein or thereby and specifically including all texture ratio ranges set forth herein. Portions of the first belt portion 300 may be joined to portions of the second belt portion 308 to form a pant. The texture zones of the first and second belt portions 300 and 308 may be continuous and uniform at least proximate to where the portions of the first belt portion 300 are joined to the portions of the second belt portion 308. In other embodiments, the texture zones of the first and second belt portions 300 and 308 may be discontinuous and uniform or non-uniform at least proximate to where the portions of the first belt portion 300 are joined to the portions of the second belt portion 308. The texture zones on the first and second belt portions may have the same texture ratio or a different texture ratio. The portions of the first belt portion 300 may be releasably or permanently joined to the portions of the second belt portion 308.

In various embodiments, referring again to FIG. 19, for example, the elastic elements 306 may be disposed intermediate at least a portion of the first substrate 302 and the second substrate 304 and may be attached to one or both of the substrates 302 and 304 using an adhesive or other material as described in greater detail above. The elastic elements 306 may also be bonded to or otherwise attached to one or both of the substrates 302 and 304. If an adhesive is used, the adhesive can be disposed on one or both of the substrates 302 and 304 and/or on at least portions of the elastic elements 306 in a pattern. The adhesive may be sprayed on, rolled on, or printed on one of the substrates 302 and 304 in the pattern. The pattern may be continuous or discontinuous or may have portions that are continuous or discontinuous. The pattern may also be linear or non-linear or may comprise discrete shapes. In an embodiment, the adhesive may be applied by contacting an adhesive applying device with one or both of the substrates 302 and 304 or a plurality of the elastic elements 306. The adhesive and/or the adhesive applying device may be heated to aid in the distribution or application of the adhesive. Some example techniques and equipment for applying the adhesives of the present disclosure are disclosed in U.S. Patent Publ. No. 2011/0274834, published on Nov. 10, 2011, to Brown et al.

Figure 22D:
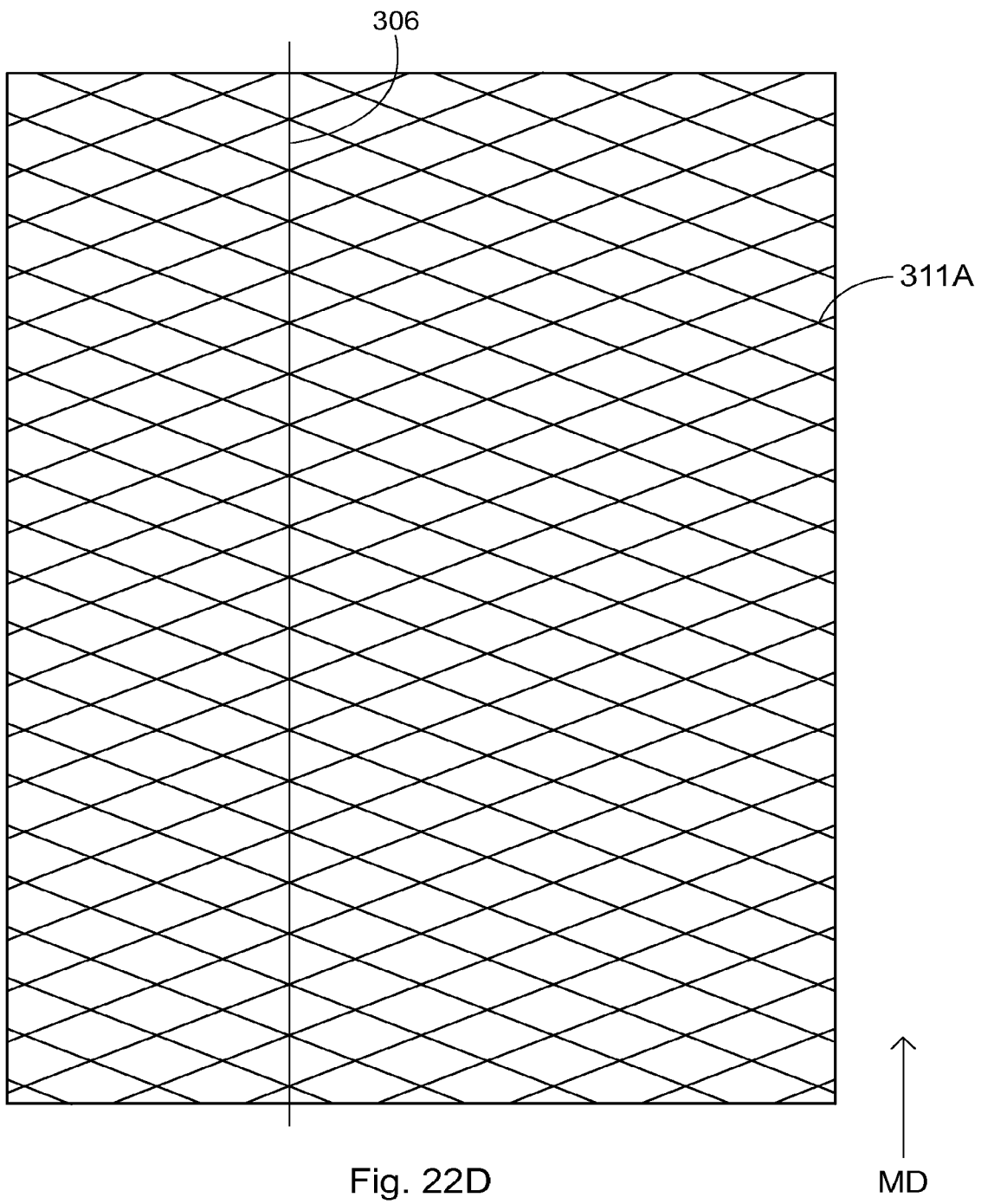
Figure 22E:
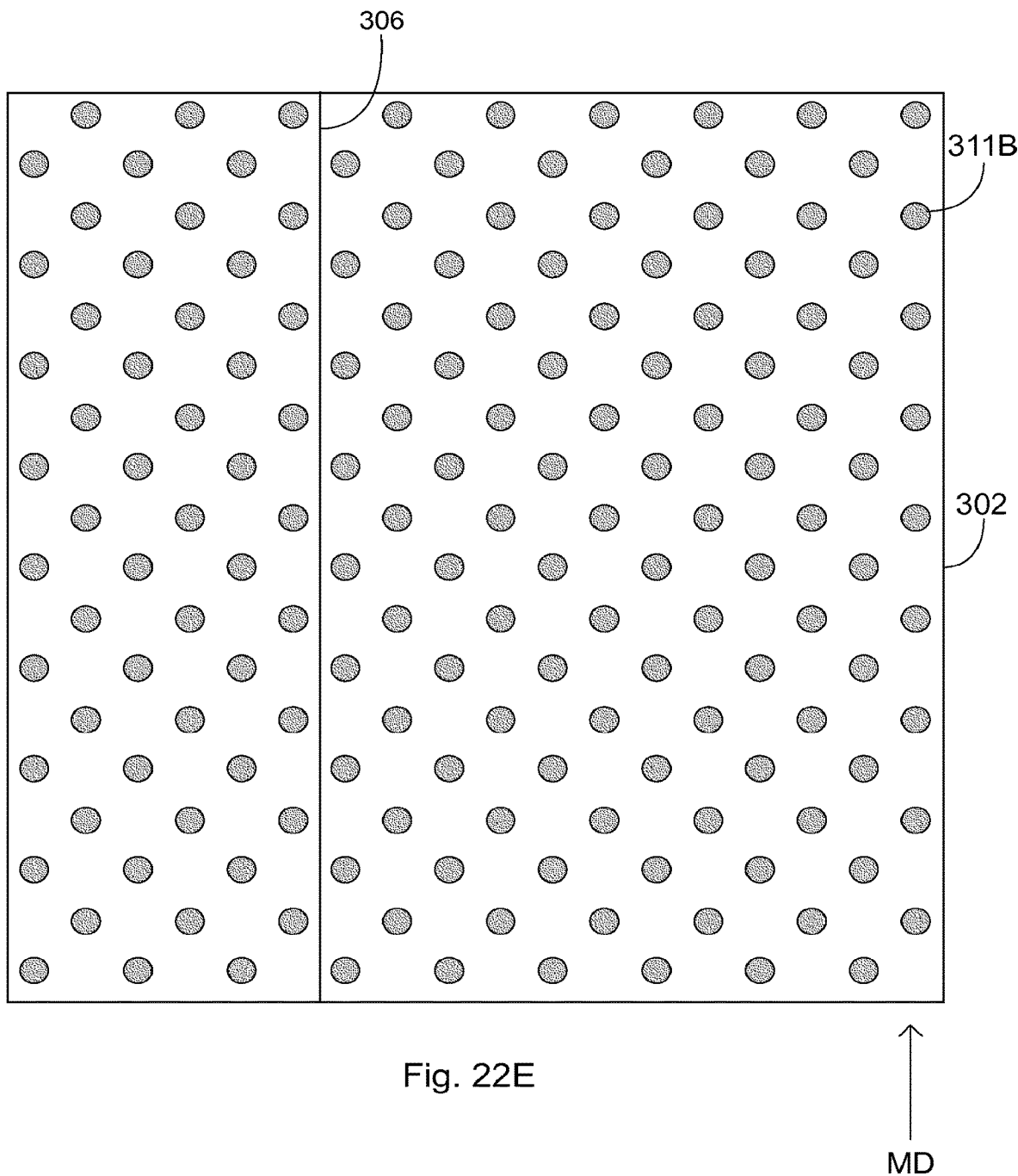
Figure 22F:
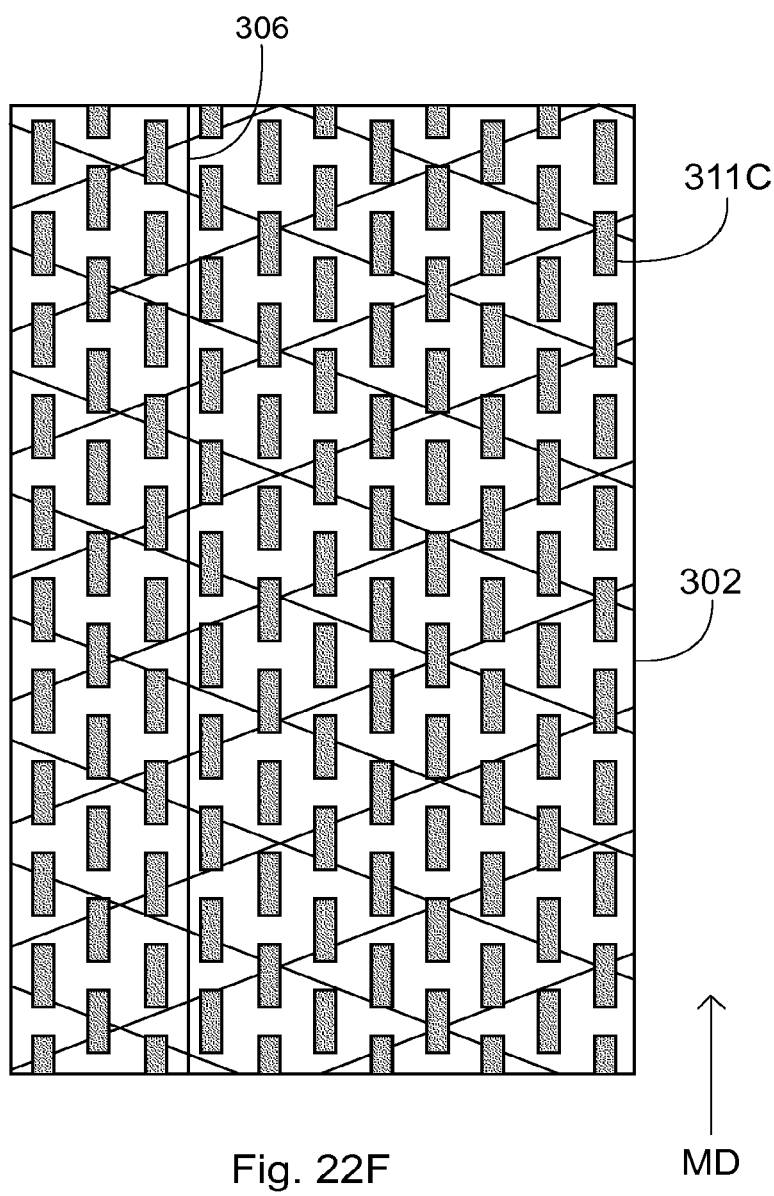

In various embodiments, referring to FIGS. 22A-22F, some example adhesive patterns of elements are disclosed on portions of a first substrate 302, for example. The machine direction (MD) is illustrated. FIG. 22A illustrates an adhesive pattern of elements 311 that may be less desirable to create the texture zones (whether macro patterns or background patterns) of the present disclosure (but that could still be used with various primary fiber bond patterns at a suitable scale of the rugosities), while the adhesive patterns of elements 311' and 311'' of FIGS. 22-22E illustrate adhesive patterns of elements 311', 311'', 311A, and 311B, respectively, that may be more desirable to create the texture zones of the present disclosure. In an embodiment, a first adhesive pattern of elements 311', such as the pattern illustrated in FIG. 22B, may be applied to one of the substrates 302 or 304 in an area of a macro pattern, while a second adhesive pattern of elements 311', such as the pattern illustrated in FIG. 22C, may be applied to one of the substrates 302 or 304 in an area of the background pattern. In another embodiment, a first adhesive pattern of elements 311A, such as the pattern illustrated in FIG. 22D, may be applied to one of the substrates 302 or 304 in an area of a macro pattern, while a second adhesive pattern of elements 311B, such as the pattern illustrated in FIG. 22E, may be applied to one of the substrates 302 or 304 in an area of the background pattern. Any of the various adhesive patterns of FIGS. 22A-22E or other adhesive patterns may be used in creating macro and background patterns in various texture zones. The patterns of elements 311C may overlap, or partially overlap, each other as illustrated in FIG. 22F. The overlapped patterns may be applied in a single adhesive application step, or applied separately. The various adhesive patterns of elements may comprise elements or discrete elements having a size and a shape. The patterns may also have different spacing between the elements. A first adhesive pattern of elements may comprise elements having a first size and a first shape and a second adhesive pattern of elements may comprise elements having a second size and a second shape. The first and second sizes and/or the first and second shapes may be the same or different. In an embodiment, the elements of the adhesive patterns of elements may be positioned on a portion of the elastic elements 306 (only one elastic element 306 is shown in FIGS. 22A-22E) in a non-continuous fashion. The elastic elements 306, in their expanded state, may be disposed over a portion of, or all of, the first substrate 302 prior to the application of the adhesive pattern(s) of elements. The second substrate 304 (not illustrated in FIGS. 22A-22E) may then be joined to portions of the first substrate 302 and/or to portions of the elastic elements 306 having the adhesive disposed thereon. As such, the elastic elements 306 may be intermittently adhesively attached to the first and second substrates 302 and 304 while in their expanded state. The different adhesive patterns of elements may be used to create the different textures in the various texture zones (whether forming background or macro patterns). These different texture zones may be created based on the location and/or area of adhesive attachment of the elastic elements 306 to one or more of the substrates 302 and 304. By attaching the elastic elements 306 differently in different texture zones, the non-attached material in the substrates 302 and 304 intermediate portions of the adhesive patterns of elements may be folded or pleated (i.e., rugosity created) when the elastic elements 306 contract to their lower or lowest energy state. The spacing between various elastic elements 306 may be the same or substantially the same and different texture zones may still be created. Also, by attaching the second substrate 304 to the elastic elements 306 differently than the attachment of the elastic elements 306 to the first substrate 302 in different texture zones, the non-attached material in the second substrate 304 intermediate portions of the adhesive patterns of elements may be folded or pleated (i.e., rugosity created) when the elastic elements 306 contract to their lower energy state. As referenced above, the elastic elements 306 may be attached to one or both of the substrates 302 and 304 via the adhesive patterns of elements when they are prestrained or expanded. Upon release of the strain on the elastic elements 306 (post-adhesive attachment), the elastic elements 306 may contract causing the non-attached material of the substrates 302 and 304 to essentially form a pattern of wrinkles, buckles, pleats, folds, or rugosities in the first and second substrates 302 and 304, thereby creating the texture zones. The wrinkles, buckles, pleats, folds, or rugosities may be formed of gathered material that can accommodate lateral stretching and contraction of the belt portions 300 and 308. The wrinkles, buckles, pleats, fold, or rugosities may be oriented along lines that may be roughly transverse or perpendicular to the direction of lateral contraction of the elastic elements 306. In the example shown, the elastic elements 306 are to contract about the machine direction. If additional texture zones are provided, more than two adhesive patterns of elements may be applied to one or both of the substrates 302 and 304 in different areas of the belt portions 300 and 308. In another embodiment, only one adhesive pattern of elements may be applied to one or both of the substrates 302 and 304 and the elastic elements 306 may be attached to the elastic elements 306 differently in each of the texture zones. In various embodiments, if the first and second substrates 302 and 304 have different primary fiber bond patterns or densified regions, as discussed below, one adhesive pattern of elements may be applied to one of both of the substrates 302 and 304 while still creating two or more texture zones in a belt portion. Different adhesive patterns of elements may also be applied to the first and second substrates 302 and/or 304 having different or the same primary fiber bond patterns or densified regions to create two or more texture zones in a belt portion.

Figure 23A:
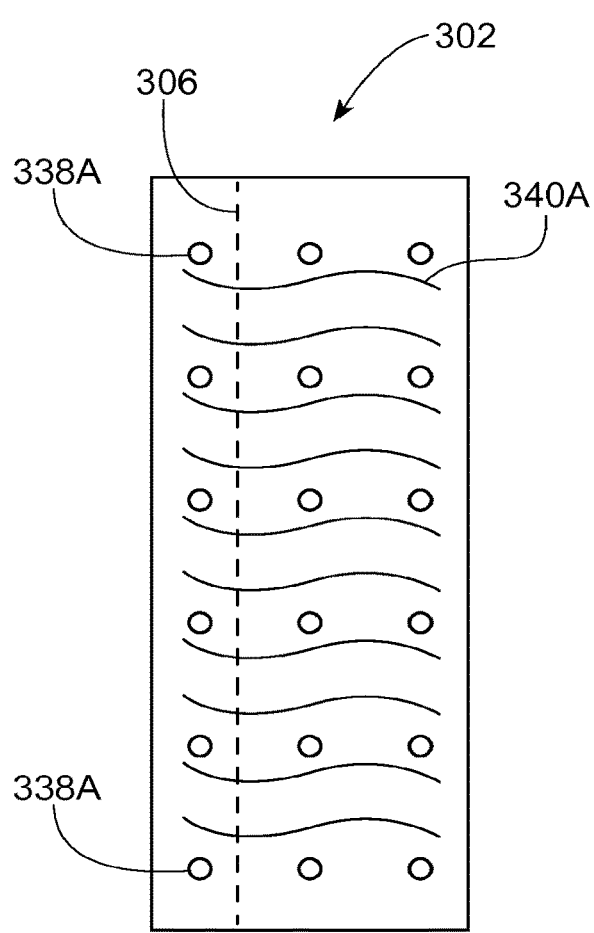
FIGS. 23A and 23B are plan views of substrates used to form a belt portion of the absorbent article, wherein the substrates comprise primary fiber bond patterns and densified regions formed therein in accordance with various non-limiting embodiments.
Figure 23B:
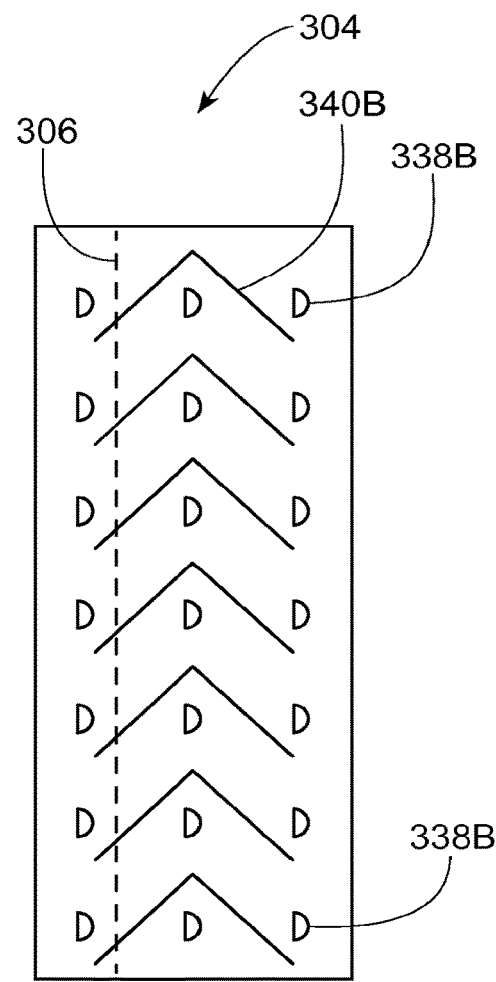

As referenced above, another way to create the rugosities in the first and second substrates 302 and 304 in various texture zones (whether forming background or macro patterns or a single texture zone) is to use substrates with different primary fiber bond patterns and/or densified regions. In such an embodiment, the adhesive pattern of elements may be the same, or substantially the same, or different, throughout the belt portions 300 and 308. In an embodiment, the first substrate 302 may have a first primary fiber bond pattern and the second substrate 304 may have a second primary fiber bond pattern. These first and second primary fiber bond patterns may be the same or different. Example primary fiber bond patterns 338A and 338B are illustrated, respectively, in FIGS. 23A and 23B on the first and second substrates 302 and 304. The patterns include the shape of the bonds, the size of the bonds, and/or the spacing between the bonds, for example. Those of skill in the art will recognize that there are a plurality of primary fiber bond patterns available or creatable on nonwoven materials and that the present disclosure is not limited to the illustrated primary fiber bond patterns. The primary fiber bonds that form the primary fiber bond patterns are the bonds that hold the fibers of materials, such as nonwoven materials, together and provide strength and structure to the substrates. The primary fiber bonds that form the primary fiber bond patterns may be thermal bonds, mechanical bonds, and/or densified regions for example. The elastic elements 306 (only 1 illustrated in each of FIGS. 23A and 23B), or portions thereof, may be adhesively attached to the first and/or second substrates 302 and 304 at some of the primary fiber bond sites or at areas in the first and second substrates 302 and 304 that do not have primary fiber bond sites. In an embodiment, some of the elastic elements 306 may be adhesively attached to the first substrate 302 and others of the elastic elements 306 may be adhesively attached to the second substrate 304. Some of the elastic elements 306, or portions thereof, may be adhesively attached to both the first and second substrates 302 and 304.

Figure 24:
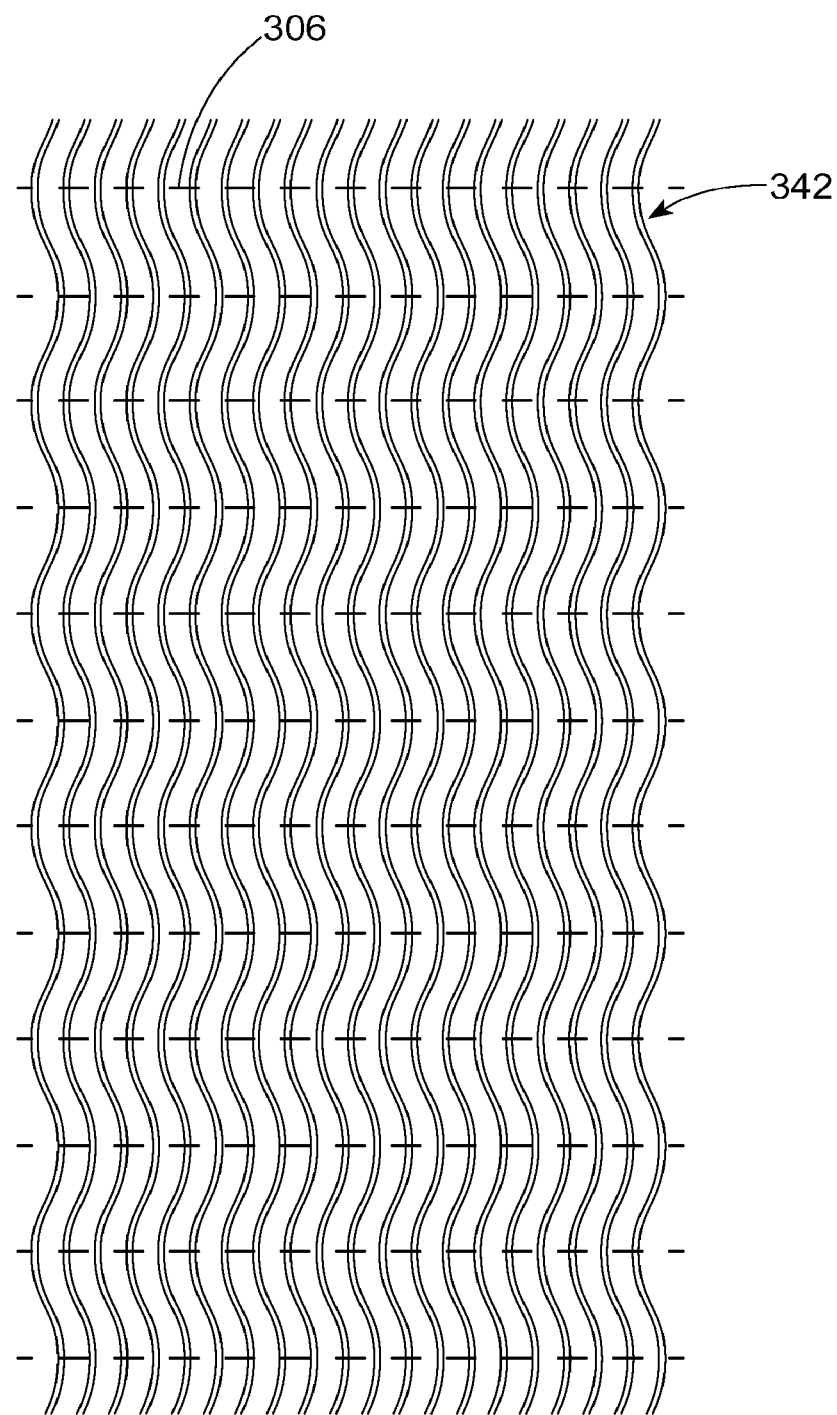
FIG. 24 is a plan view of a densified region pattern and elastic elements in accordance with one non-limiting embodiment.

In an embodiment, referring again to FIGS. 23A and 23B, in addition to or in lieu of the primary fiber bond patterns 338A and 338B, one or both of the first and second substrates 302 and 304 may comprise patterns of densified regions, such as densified regions 340A and 340B. The patterns may include the shape of the densified regions, the size of the densified regions, and/or the spacing between the densified regions, for example. In an embodiment, the densified regions may also function to form primary fiber bonds in the substrates. The densified regions may be formed by calendering, embossing, heating, other mechanical or thermal deformation, and/or densification. The densified regions may have a larger area, length dimension, and/or width dimension when compared to the areas and length and width dimensions of the primary fiber bonds 338A and 338B. In an embodiment, the densified regions, or portions thereof, may extend transverse or perpendicular to the longitudinal axis of at least one elastic element 306. Only 1 elastic element 306 is illustrated in each of FIGS. 23A and 23B to simplify the figures. In an embodiment, the densified regions may form shapes or other indicia. Various densified regions may be continuous, substantially continuous, or discontinuous throughout their length. Some densified regions may be continuous while others may be discontinuous, for example. The densified regions may be linear or nonlinear (e.g., arcuate) or may have linear or non-linear portions and may form patterns in one or both of the first and second substrates 302 and 304. The pattern of densified regions in the first substrate 302 may be the same as or different than the pattern of densified regions in the second substrate 304. In an embodiment, densified regions in a single substrate may also be bonded between two or more material layers of the substrate, if the substrate is a composite. Some example patterns of densified regions 340A and 340B are illustrated in the substrates 302 and 304 in FIGS. 23A and 23B. The densified regions 340A and 340B, at some locations, may intersect with the primary fiber bonds 338A and 338B. Another pattern of densified regions 342 is illustrated in FIG. 24 without any additional primary fiber bonds being present. The elastic elements 306 are shown in dash in FIG. 24 for reference. The distance between various densified regions may be the same or consistent or different. If they are the same or consistent, different texture zones may still be provided by using different adhesive patterns of elements, for example. In various embodiments, primary fiber bonds and/or densified regions may be provided in one or both of the first and second substrates 302 and 304. In an embodiment, primary fiber bonds may be provided in the first substrate 302 and densified regions may be provided in the second substrate 304, for example. In various embodiments, the densified regions, or portions thereof, may extend in a direction generally transverse, perpendicular, or substantially perpendicular to, the direction of extension of the elastic elements 306.

The terms "primary fiber bond" and "densified region" each refer to bonds formed in a substrate. The primary fiber bonds and densified regions will each have a thickness in a direction perpendicular to a plane of the substrate in which they are formed that is less than any areas of the substrate not comprising primary fiber bonds or densified regions (i.e., unbonded areas). In an embodiment, the primary fiber bonds may have the same or a different thickness as the densified regions. In various embodiments, the densified regions may have a larger perimeter, length (L), and/or width (w) than the primary fiber bonds. The terms "primary fiber bond pattern" and "pattern of densified regions" refer to a pattern of primary fiber bonds or a pattern of densified regions, respectively, imparted to a substrate. The term "bond" refers to a distinct location, on a bonded fibrous substrate, at which the fibers or filaments of the substrate are substantially more interconnected, when compared with the fibers or filaments of the unbonded areas of the substrate. The term "bond perimeter" refers to the outermost edge of the bond (either a primary fiber bond or a densified region) that defines the boundary between the primary fiber bond or densified region and the surrounding unbounded or undensified area. As discussed below, the perimeter may be measured by measuring the sides of the bonds and then taking the sum of those sides.

A primary fiber bond pattern and a pattern of densified regions may be imparted to a fibrous web in various ways, such as by using heat, pressure, ultrasonic bonding, adhesives, or other bonding techniques known to those of skill in the art, or combinations of any of these. For example, a fibrous substrate may be bonded by passing the fibrous substrate through a nip formed by a heated calender roll (with a plurality of raised lands) and another roll, such that the lands form primary fiber bonds or densified regions on the fibrous substrate.

Figure 25A:
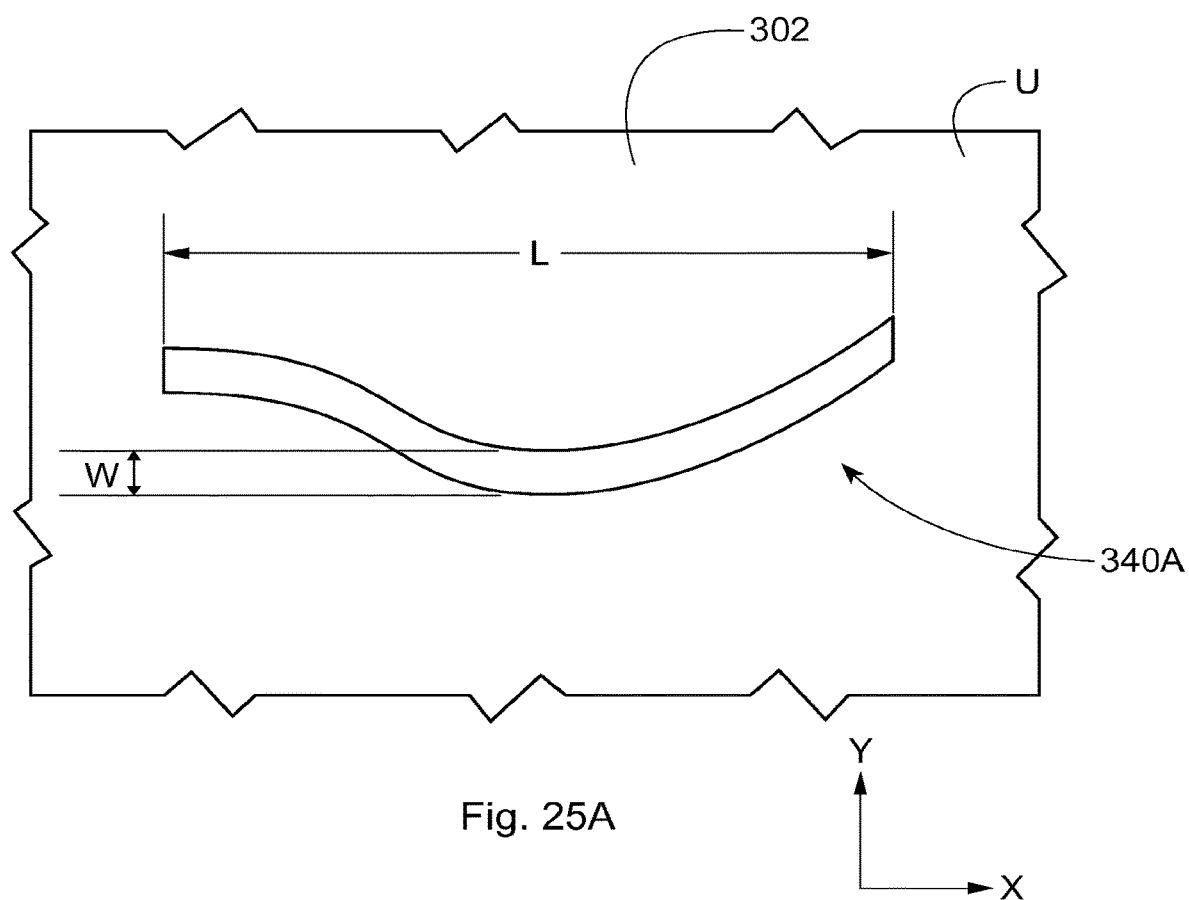
FIG. 25A is a plan view of a densified region on a first substrate in accordance with one non-limiting embodiment.
Figure 25B:
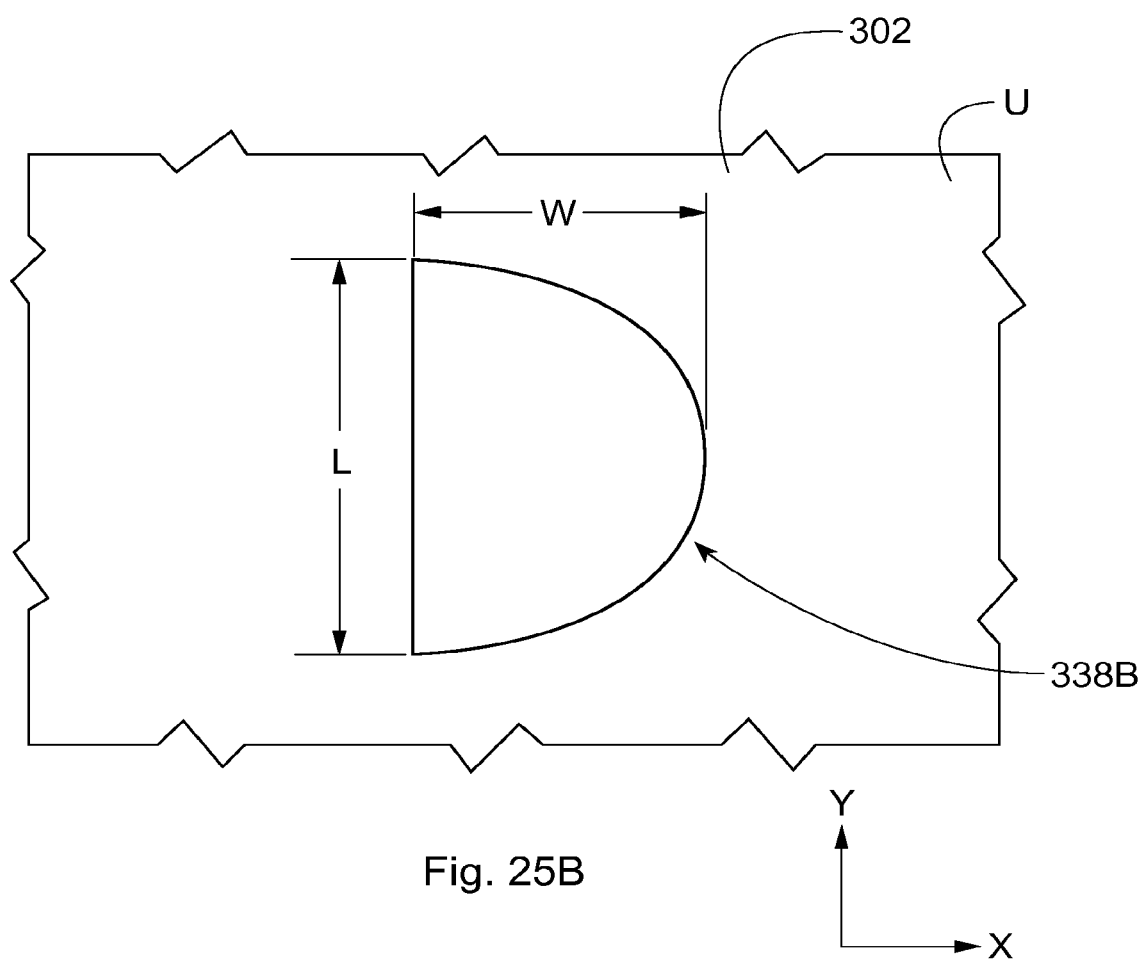
FIG. 25B is a plan view of a primary fiber bond on a first substrate in accordance with one non-limiting embodiment.

Referring to FIGS. 25A and 25B, an example of a densified region 340A (FIG. 25A) and a primary fiber bond 338B (FIG. 25B) each having a length (L) and a width (W) are illustrated. Unbonded areas (U) are also shown. The length (L) is measured linearly, from one end of the primary fiber bond or densified region to the other end of the primary fiber bond or densified region in the X or Y direction of the Cartesian coordinate system. The length (L) forms the primary fiber bond's or densified region's longest dimension regardless of whether it is in the X or Y direction. The width (W) is measured linearly from one side of the primary fiber bond or densified region to the other side of the primary fiber bond or densified region. The width is measured about the Y or X direction (in the opposite direction of how the length (L) was measured) perpendicular to the length (L). If the primary fiber bond or densified region forms a circle, the width (W) will be equal to the length (L).

In various embodiments, each of the densified regions, no matter what configuration they take on may have a perimeter and an area. In an embodiment, each of the densified regions may have a perimeter of greater than about 1 mm, greater than about 2 mm, greater than about 3 mm, greater than about 4 mm, or greater than about 5 mm. In other embodiments, the perimeter of the densified regions may be in the range of about 1 mm to about 100 mm, or alternatively about 1 mm to about 50 mm, specifically reciting all 0.1 mm increments within the specified ranges and all ranges formed therein or thereby. The perimeter can be measured by measuring each of the sides of the densified regions and taking the sum of those sides. In an embodiment, each of the densified regions may have an area greater than about 2 $mm^2$, greater than about 4 $mm^2$, greater than about 5 $mm^2$, greater than about 6 $mm^2$, or greater than about 7 $mm^2$. In other embodiments, the area of the densified regions may be in the range of about 0.5 $mm^2$ to about 150 $mm^2$, or alternatively about 2 $mm^2$ to about 100 $mm^2$, specifically reciting all 0.1 $mm^2$ increments within the specified ranges and all ranges formed therein or thereby. The perimeter and area of each of the densified regions may be greater than the perimeter and area of the each of the primary fiber bonds. In various embodiments, the densified regions may each have a minimum dimension or narrowest dimension that is about 0.5 mm, alternatively in the range of about 0.5 mm to about 20 mm, specifically reciting all 0.1 mm increments within that range and all ranges formed therein. The densified regions may each have a longest dimension of 0.5 mm to about 30 mm, specifically reciting all 0.1 mm increments within that range and all ranges formed therein. The densified regions in a substrate may have the same dimensions or may have different dimensions. If the densified regions are continuous, the length in the maximum dimension of the densified regions may be assumed equal to the sample size measured. A suggested sample size is 25 mm in length. All dimensions discussed herein may be measured by hand, using a measuring tape, or by using a measuring machine. Furthermore, the densified regions in one substrate of a laminate may be the same as or different than the densified regions in the second substrate of the laminate. In other embodiments, only one substrate of a laminate may have densified regions.

In various embodiments, the densified regions may each have an aspect ratio. The aspect ratio is the ratio of the densified region's length at its longest point to its width at its widest point. In various embodiments, a densified region has a length, L and a width, W. The aspect ratio of the densified region is L/W. The length and width of a densified region may be measured by hand, using a measuring tape, or by using a measuring machine. As some examples, the aspect ratio of densified regions of the present disclosure may be 1, 2, 3, 4, 5, 6, 7, 8, in the range of about 2 to about 100, or in the range of about 2 to about 200, specifically reciting all 0.1 increments within those ranges and all ranges formed therein or thereby.

The pattern of densified regions or primary fiber bonds and their positioning throughout one or both of the substrates 302 and 304 may dictate what texture or range of rugosities a particular texture zone, forming either a background pattern or a macro pattern, may have. The type of texture or range of rugosities in a particular texture zone may also be a result of a combination of two of the pattern of densified regions in one or more of the substrates, the pattern of primary fiber bonds in one or more of the substrates, and the adhesive pattern within a particular texture zone.

In an embodiment, a method of making a belt portion comprising one or more texture zones (e.g., one, two, three, four etc.) is disclosed. The texture zones may form background patterns or macro patterns in the belt portion. The belt portion may comprise a plurality of elastic elements or elastic stands disposed between a first substrate, or a first nonwoven substrate, and a second substrate, or a second nonwoven substrate. The substrates may also be formed by other materials as discussed herein. The method may comprise applying an adhesive to the first substrate in a first pattern of elements and in at least a second pattern of elements. The first pattern of elements may be positioned on a first area of the first substrate and the second pattern of elements may be positioned on a second area of the first substrate. In an embodiment, the patterns may not overlap, while in other embodiments, the patterns may overlap or intersect. The elements in the adhesive patterns of elements may be discrete elements, non-linear elements, and/or linear elements. The adhesive may be applied to the first substrate by intermittently compressing the first substrate between a slot die applicator and a substrate carrier comprising a plurality of raised members, for example. A first portion of the raised members may be situated in the first pattern of elements, while a second portion of the raised members may be situated in the second pattern of elements. The method may also comprise adhesively attaching portions of the elastic elements to the first substrate using the elements. The elastic elements may be applied to the first substrate when they are in their stretched or expanded state and then allowed to contract into a non-expanded or partially expanded state to, in part, create the various texture zones in the first substrate. In other embodiments, the adhesive may be applied to the elastic elements in the first and second patterns of elements and then the elastic elements, in their stretched or expanded state, may be applied to the first and/or second substrates and then allowed to contract into a non-expanded or partially expanded state thereby creating, in part, the various texture zones in the first substrate. The method may also comprise attaching the second substrate to the first substrate and/or to portions of at least some of the elastic elements. This attachment may be made by bonding portions of the first substrate to portions of the second substrate and/or by attaching portions of at least some of the elastic elements to both the first and second substrates. The first and second patterns of elements may, in part, form two, different texture zones in the first and second substrates. The first pattern of elements may form the first texture zone forming a background pattern and the second pattern of elements may form the second texture zone forming a macro pattern. The first texture zone forming the background pattern may have rugosities having a first frequency and/or amplitude range and the second texture zone forming the macro pattern may have rugosities having a second, different frequency and/or amplitude range. If additional different texture zones are desired, more than two adhesive patterns of elements may be applied to the elastic elements or to the first or second substrates.

In an embodiment, another method for making a belt portion comprising one or more texture zones is disclosed. A first texture zone may form a background pattern and a second texture zone may form a macro pattern in the belt portion. The belt portion may comprise one or more elastic elements or elastic stands disposed between a first substrate and a second substrate. The method may comprise applying an adhesive to the first substrate by intermittently compressing the first substrate between a slot die applicator and a substrate carrier. The substrate carrier may comprise a plurality of raised elements situated in a pattern and the adhesive may be applied to the first substrate in the pattern. The substrate carrier may be an endless belt or a roller. The adhesive may be applied to the first substrate in a first pattern of elements and in a second pattern of elements. The first pattern of elements may be positioned on a first area of the first substrate and the second pattern of elements may be positioned on a second area of the first substrate. In an embodiment, the patterns may not overlap, while in other embodiments, the patterns may overlap or intersect. The elements may be discrete elements, non-linear elements, and/or linear elements. The method may also comprise engaging portions of at least some of the elastic elements with the adhesive when the elastic elements are in their stretched or expanded state. The method may also comprise attaching the second substrate to the first substrate and/or to the one or more elastic elements. After the elastic elements are adhesively attached to the first and/or second substrates, the elastic elements are allowed to relax or contract, thereby creating texture zones (forming background and macro patterns) in the first and/or second substrates. The first pattern of elements may be associated with a first texture zone forming a background pattern and a second pattern of elements may be associated with a second texture zone forming a macro pattern in the first and/or second substrates.

A first texture zone may have rugosities having a first frequency and/or amplitude range and a second texture zone may have rugosities having a second, different frequency and/or amplitude range. If additional different texture zones are desired, more than two adhesive patterns of elements may be applied to the elastic elements or to the first or second substrates.

In an embodiment, a belt portion may comprise a first adhesive pattern of elements adhesively engaging a first portion of one or more elastic elements in a first texture zone forming a background pattern in the belt portion and a second adhesive pattern of elements adhesively engaging a second portion of the one or more elastic elements in a second texture zone forming a macro pattern. The first adhesive pattern of elements may be the same as or different than the second adhesive pattern of elements. If the first adhesive pattern of elements is the same as, or substantially the same as, the second adhesive pattern of elements, a first pattern of primary fiber bonds and/or densified regions in a first substrate of a belt portion may be different than a second pattern primary fiber bonds and/or densified regions in a second substrate of the belt portion. In other embodiments, still with the adhesive patterns of elements being the same, or substantially the same, one of the substrates may have a first pattern of primary fiber bonds and/or densified regions and a second pattern of primary fiber bonds and/or densified regions formed therein. The first pattern of primary fiber bonds and/or densified regions may be different than the second pattern of primary fiber bonds and/or densified regions. If the first adhesive pattern of elements is different than the second adhesive pattern of elements, a first pattern of primary fiber bonds and/or densified regions in a first substrate of a belt portion may be the same as, or substantially the same as, a second pattern of primary fiber bonds and/or densified regions in a second substrate of the belt portion. Also, still with different adhesive patterns of elements, a first pattern of primary fiber bonds and/or densified regions in a first substrate of a belt portion may be different than a second pattern of primary fiber bonds and/or densified regions in a second substrate of the belt portion. Furthermore, still with different adhesive patterns of elements, one of the substrates may have a first pattern of primary fiber bond and/or densified regions and a second, different pattern of primary fiber bonds and/or densified regions. In an embodiment, the densified regions may act as primary fiber bonds and additional primary fiber bonds may not need to be required.

In an embodiment, a belt portion may comprise a first substrate, a second substrate, and at least a third substrate. One or more elastic elements may be positioned intermediate any or all of the substrates may form at least one or two texture zones on at least one of the outer substrates of the structure or throughout the entire structure.

In an embodiment, referring generally to FIG. 17 as an example, an absorbent article may comprise a chassis comprising a topsheet, a backsheet, and a core disposed intermediate the topsheet and the backsheet. The absorbent article may comprise two belt portions extending from the chassis. Each of the belt portions may comprise a first substrate, a second substrate, and one or more elastic elements disposed intermediate the first substrate and the second substrate. Portions of the elastic elements may be joined to the first substrate. The second substrate may be joined to the first substrate or to portions of the elastic elements. The belt portion may also comprise a first texture zone comprising a plurality of rugosities formed in the first substrate. The plurality of the rugosities may have a first frequency range. The first texture zone may form a background pattern in the belt portion. The belt portion may also comprise a second texture zone comprising a plurality of rugosities formed in the first substrate. The plurality of rugosities may have a second, different frequency range. The second texture zone may form a macro pattern in the belt portion. The absorbent article of FIG. 17 may provide many benefits over related art absorbent articles such as not using additional substrates to form texture zones, providing an improved fit and comfortable feel, having an aesthetically pleasing appearance, and more closely resembling clothing or underwear, without adding cost, or significant cost, to the absorbent article and its manufacturing process.

In an embodiment, an absorbent article may comprise a chassis comprising a topsheet, a backsheet, and a core disposed at least partially intermediate the topsheet and the backsheet. The absorbent article may comprise one or two belt portions extending from the chassis. The belt portions may each comprise an elasticized portion having a texture ratio in the range of about 5 to about 20 or about 5 to about 25 (or other texture ratios specified herein). The elasticized portion may form a single uniform texture. The absorbent article comprises a longitudinal axis. The single uniform texture may be linear or nonlinear in a direction parallel to the longitudinal axis. The elasticized portion may comprise two or more substrates or two or more nonwoven substrates that are adhesively or otherwise joined to each other. The total basis weight of the belt portion may be in the range of 20 gsm to 100 gsm, 25 gsm to 90 gsm, 35 gsm to 70 gsm, or 40 gsm to 60 gsm, measured according to the Basis Weight Method described below, specifically reciting all 0.5 gsm increments within the specified ranges and all ranges formed therein or thereby.

In an embodiment, an absorbent article may comprise a chassis comprising a topsheet, a backsheet, and a core disposed at least partially intermediate the topsheet and the backsheet. The absorbent article may comprise one or more belt portions extending from the chassis. The belt portions may each comprise a first substrate, a second substrate joined to the first substrate, and a plurality of elongate elastic elements disposed between the first substrate and the second substrate. The belt portions may each comprise one or more texture zones each having a texture ratio of greater than 5 and less than 25 (and other texture ratios recited herein). The distance intermediate each of the elastic elements may be at least 4 mm and less than 35 mm (or other distances specified herein). The elongate elastic elements may be adhesively joined, or otherwise joined, to portions of the first substrate or to portions of the second substrate.

Densified Region Measurement Method

Dimensional measurements are performed on images generated using a flat bed scanner capable of scanning at a resolution of at least 2400 dpi in reflectance mode (a suitable scanner is the Epson Perfection V750 Pro, Epson, USA). Analyses are performed using ImageJ software (National Institutes of Health, USA) or equivalent image analysis software, and calibrated against a certified NIST ruler. The samples are preconditioned at about 23° C.±2 C.° and about 50%±2% relative humidity for 2 hours prior to testing.

To obtain the specimen, carefully remove the laminate from the garment-facing surface of the absorbent article. Then, extend the laminate to remove the rugosity, cut a square 35 mm by 35 mm from the laminate, and mount the laminate on an opaque black backing with the wearer-facing surface facing toward the backing.

Set the scanner to acquire an 8 bit grayscale image at 2400 dpi in reflectance mode. Place the mounted specimens on the flat bed scanner, garment-facing surface facing downward. Place the ruler directly adjacent to the specimen. Close the scanner's cover and acquire and save an image composed of the laminate specimen and the ruler. Open the image file in the ImageJ software and perform a linear calibration using the imaged ruler.

Dimensional measurements are made in triplicate at random sites on each specimen from corresponding sites on three identical absorbent articles. The nine values are averaged and reported to the nearest 0.01.

Not being bound by the specific densified region, FIG. 25A is referenced as an example to illustrate the following dimension measurements. These measures are equally applicable to other densified shapes and patterns.

Length (L):

The densified region has a profile with a greatest measurable length (i.e., longest portion of the densified region). Identify a shape length line formed from two points on the profile that are farthest apart along the longitudinal length. Draw a line through the profile using these points. With the measuring tool, measure the length along the line segment between the farthest-most points on the profile to the nearest 0.01 mm.

Width (W):

The densified region has a profile with a greatest measurable width (i.e., widest portion of the densified region). Draw two lines, parallel to the shape length line described above, which are tangent to the profile at one or more outermost points that are most distant from the shape length line. With the measuring tool, measure the width between the two tangent lines along a line segment perpendicular to the shape length line to the nearest 0.01 mm.

Aspect Ratio:

The aspect ratio of the densified region is the ratio of the greatest measurable length, L, divided by the greatest measurable width, W. Report the aspect ratio to the nearest 0.01 mm.

Perimeter Length (P):

The perimeter of the densified region or bond site can be measured using the freehand selection tool to manually trace the perimeter. Report the perimeter length to the nearest 0.01 mm.

Basis Weight Method

Remove the belt portion from the absorbent article using freeze spray or suitable method to avoid damaging the substrates of the belt portion. If the absorbent article is a pant, cut the belt along the longitudinal axis of the seams areas to separate the belt into front and back belt portions and lay each belt portion flat on a horizontal bench. For each belt portion, execute the following steps:

Secure the cut belt portion to the bench with tape along one edge of the cut belt portion. The selected edge should extend in a direction perpendicular to or transverse to the longest dimension of the rugosities.

Extend the cut belt portion to remove the rugosities and secure the edge opposing the taped edge to the horizontal bench with tape.

Measure the longitudinal and lateral dimensions of the cut belt portion with a ruler calibrated against a certified NIST ruler and accurate to 0.5 mm. Report the dimensions to the nearest 0.5 mm.

Use the longitudinal and lateral dimensions of each belt portion to calculate the area of the belt portion in square meters to the nearest 0.000001 m2.

Measure the mass of the same cut belt portion in grams using a scale accurate to 0.01 g. Divide the measured mass of the cut belt portion by the calculated area of the cut belt portion.

Repeat this method for 10 absorbent articles having belt portions, taking the samples from the same location on each belt portion of each absorbent article.

Report the average of the 10 samples for each front and back belt portions, if applicable, to the nearest 0.1. g/square meter to obtain the basis weight of a belt portion.

Rugosity Length, Rugosity Frequency, Rugosity Amplitude, Elastic Element Spacing, and Texture Ratio Method Rugosity length (mm) and rugosity amplitude measurements are taken by light microscopy with image analysis. A suitable instrument is a HIROX Microscope (Model KH7700) fitted with Adapter OL-35 and lens MXG 10-C or equivalent. An external white light source is used. Images are acquired and analyzed with HIROX software (Version 2.10C) or equivalent 3D image analysis software. The sample is preconditioned at 23° C.±2 C.° and 50%±2% relative humidity for 2 hours prior to testing.

To obtain a specimen, carefully remove a belt portion from an absorbent article using freeze spray or other suitable method to avoid damaging the substrates of the belt portion. Cut three squares from a single texture zone in the belt portion with each side of the squares equal to 35 mm using scissors or other suitable cutting instrument. If three 35 mm×35 mm squares are not available in a single texture zone, cut additional squares from other identical belt portions from other identical absorbent articles. If a front belt portion is used to obtain the first specimen, front belt portions should also be used to obtain the second and third specimens. The same applies to rear belt portions. The squares are cut with two sides parallel to the machine direction and with two sides parallel to the cross direction of the belt portion, as the belt portion is situated on the absorbent article.

Mount the specimen on a microscope stage of a microscope with the garment-facing surface facing away from the microscope stage. Center the sample on the stage. Turn on the external white light source and focus the image, noting the lower rugosity surface location (bottom of the troughs on the garment facing surface) and the upper rugosity surface location (peaks on the garment-facing surface) to create a three dimensional rendering of the image in the software. Acquire and save the image. Use the measurement tool in the image analysis software to observe the profile at a location midway between 2 elastic elements. Measure the length between rugosity peaks (on rugosities having amplitudes greater than 0.25 mm) (3 measurements per specimen). These length measurements are made in triplicate at random sites on the first specimen and from corresponding sites on the other two specimens. The nine length values are averaged and reported to the nearest 0.001 cm as the Average Rugosity Length. Save the image and measurements and retain the specimens.

Average Rugosity Amplitude is measured using the image analysis software. The amplitude is the vertical distance between a rugosity peak and an adjacent rugosity trough. Use the measurement tool in the image analysis software to observe the profile at a location midway between 2 elastic elements. Measure the vertical (Z-direction) length between a rugosity peak and adjacent rugosity trough (3 measurements per specimen). These amplitude measurements are made in triplicate at the same sites as in the Rugosity Length measurement on the first specimen and from corresponding sites on the other two specimens. The nine rugosity amplitude values are averaged and reported to the nearest to the nearest 0.0001 cm as the Average Rugosity Amplitude.

Rugosity Frequency is defined as the number of rugosities per cm. The Average Rugosity Frequency is calculated by taking the inverse of the Average Rugosity Length and reporting to the nearest 0.1 rugosities/cm.

Using a ruler calibrated against a certified NIST ruler and accurate to 0.5 mm, measure the distance between elastic elements corresponding to the locations of the rugosities measured in the specimen. Measure at least three elastic element spacings per specimen and repeat over the three specimens. Average the 9 values to obtain the Average Elastic Element Spacing (cm) and report to the nearest 0.01 cm.

Divide the Average Elastic Element Spacing (cm) by the Average Rugosity Length (cm) to calculate the "Texture Ratio" and report the Texture Ratio to the nearest 0.1.

EXAMPLE

In a non-limiting example embodiment, a belt portion of the present disclosure uses a first substrate of about 10 gsm nonwoven material supplied by Avgol, Israel, under the trade name XY-S70-26. A second substrate for the belt portion uses a 45 gsm nonwoven material supplied by Mitsui, Japan, under the trade name NW8019.000. Elastic strands with a linear density of about 680 decitex supplied by Hyosung, Korea, under the brand name Creora, are adhesive attached to the first substrate using H2401 adhesive by Bostik, Wis., USA. A first texture zone forming a background pattern is created in the belt portion of the absorbent article by spacing the elastic strands about 7 mm apart and by using a Nordson Universal glue applicator and Nordson sure-wrap glue nozzles prior to combining the first and second substrates. A second texture zone forming a macro pattern is created in the belt portion of the absorbent article by applying H2401 adhesive to the second substrate using about 5 mm diameter dots of adhesive as illustrated FIG. 22E prior to combining the first and second substrates. These background (334) and macro (336) patterns result in the texture illustrated in FIG. 17 and the texture of the white portion of FIG. 18.

Comparative Texture Ratio Examples

Using the Rugosity Length, Rugosity Frequency, Rugosity Amplitude, Elastic Element Spacing, and Texture Ratio Method, various texture zones of competitive absorbent articles and the absorbent articles of the present disclosure were tested, as illustrated in Chart 1 below. In general, the competitive absorbent articles had a uniform texture in the front and the back. In some competitive absorbent articles, the front was used and in other competitive absorbent articles the back was used. If the front/back was used, it was used for the entire test of that particular competitive absorbent article.

Chart 1

| Product | Size | Manufacturer | Rugosity Length Average (cm) | Elastic Element Spacing Average (cm) | Texture Ratio |
|---|---|---|---|---|---|
| Mamy Poko- Waist Band | 4 | Unicharm | 0.14 | 0.63 | 4.6 |
| Mamy Poko- Belt Portion | 4 | Unicharm | 0.18 | 0.8 | 4.5 |
| Kao Relief- Barrier Leg Cuff | Small (Adult Incontinence Product) | Kao | 0.16 | 0.45 | 2.8 |

| Product | Size | Manufacturer | Rugosity Length Average (cm) | Elastic Element Spacing Average (cm) | Texture Ratio |
|---|---|---|---|---|---|
| Walgreens-Belt Portion | 4 | First Quality | 0.20 | 0.7 | 3.6 |
| Moony-Belt Portion | 4 | Unicharm | 0.28 | 0.5 | 1.7 |
| Merries-Belt Portino | 4 | Kao | 0.24 | 0.5 | 2.1 |
| Libero-Waist Band | 4 | SCA | 0.18 | 0.5 | 2.8 |
| Huggies-Side Panel | 4 | Kimberly Clark | 0.10 | 0.3 | 3.0 |
| Present Disclosure-Belt Portion | 4 | NA | 0.12 | 0.7 | 6.0 |

Figure 26:
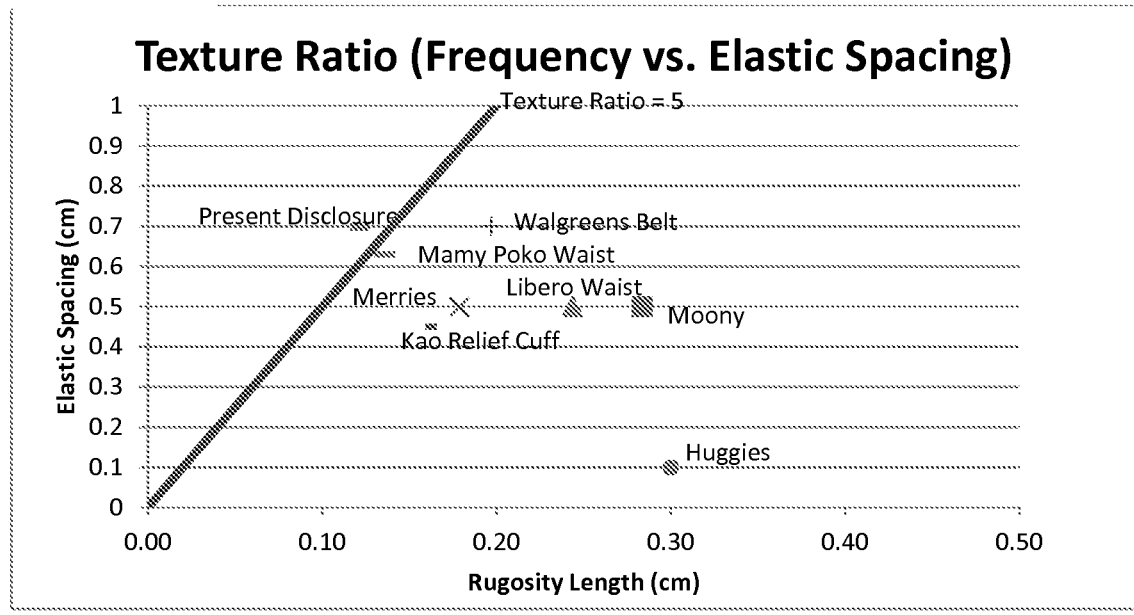
FIG. 26 is a graphical illustration of the texture ratio of various absorbent articles, including the absorbent articles of the present disclosure, in accordance with one non-limiting embodiment.
Figure 27:
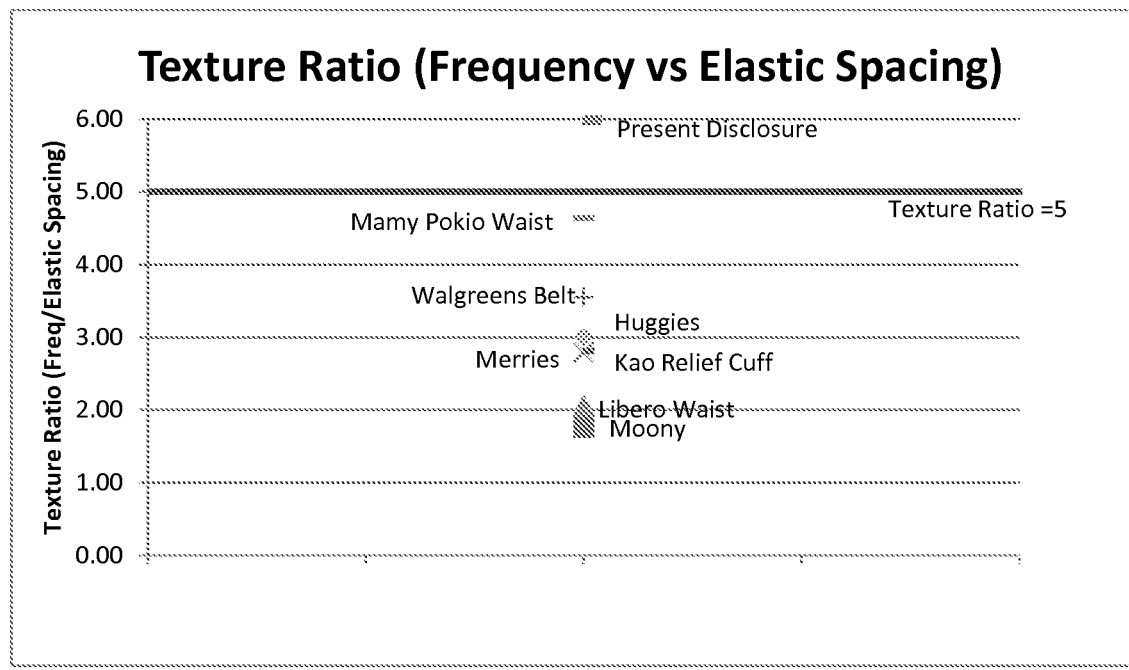
FIG. 27 is another graphical illustration of the texture ratio of various absorbent articles, including the absorbent articles of the present disclosure, in accordance with one non-limiting embodiment.

Samples of the texture zones of the present disclosure exhibited a texture ratio of 6.0 using the Rugosity Length, Rugosity Frequency, Rugosity Amplitude, Elastic Element Spacing, and Texture Ratio Method. The highest texture ratio found in the texture zones of the tested competitive absorbent articles was only 4.6, with most competitive absorbent articles falling significantly below the texture ratio of 4.6. FIGS. 26 and 27 illustrate graphs of the texture ratios of texture zones of the tested competitive absorbent articles compared to the texture ratios of texture zones of the absorbent articles of the present disclosure. FIG. 26 illustrates a graph of Average Rugosity Length (cm) along the x-axis compared to Average Elastic Spacing (cm) along the y-axis. FIG. 27 illustrates another graph of the texture ratios of texture zones of the tested competitive absorbent articles compared to the texture ratios of the texture zones of the absorbent articles of the present disclosure. As can be seen, the texture ratios of the texture zones belt portions of the absorbent articles of the present disclosure are higher than the tested competitive absorbent articles, which provides the absorbent articles of the present disclosure with an improved fit, a comfortable feel, an aesthetically pleasing appearance, and a product that more closely resembles clothing or underwear without adding cost, or significant cost, to absorbent article manufacturing. An example texture zone having a texture ratio of around 6.0 is illustrated in FIG. 20A, for example.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, those of skill in the art will recognize that various other changes and modifications can be made without departing from the spirit and scope of the invention. It is therefore intended to cover in the appended claims all such changes and modifications that are within the scope of this invention.

What is claimed is:

1. An absorbent article comprising:
    a chassis comprising:
        a topsheet;
        a backsheet; and
        a core disposed at least partially intermediate the topsheet and the backsheet; and
    a belt portion extending from the chassis, the belt portion comprising:
        a first substrate;
        a second substrate;
        a plurality of elastic strands disposed at least partially intermediate the first substrate and the second substrate, wherein portions of the elastic strands are joined to the first substrate, wherein the second substrate is joined to the first substrate or to portions of the elastic strands, and wherein the elastic strands have an elastic strand spacing in the range of about 2 mm to about 4 mm, according to the Rugosity Length, Rugosity Frequency, Rugosity Amplitude, Elastic Element Spacing, and Texture Ratio Method described herein;
        a continuous texture grid comprising a first plurality of rugosities formed in the first substrate, wherein the first plurality of the rugosities have a first frequency range and a first amplitude range, and wherein the first plurality of rugosities have a minimum amplitude of 1 mm; and
        a plurality of discrete texture areas each comprising a second plurality of rugosities formed in the first substrate, wherein the second plurality of the rugosities have a second, higher frequency range and a second, smaller amplitude range, and wherein the second plurality of the rugosities have a minimum amplitude of 1 mm;
        wherein a portion of the first substrate is nested with a portion of the second substrate in the first plurality of rugosities or in the second plurality of rugosities.

2. The absorbent article of claim 1, wherein the plurality of discrete texture areas are positioned only within the continuous texture grid.

3. The absorbent article of claim 1, wherein the first substrate comprises a first nonwoven substrate, and wherein the second substrate comprises a second nonwoven substrate.

4. The absorbent article of claim 1, wherein the belt portion comprises:
    a first adhesive pattern of elements on the first substrate and adhesively engaging a first portion of the one or more elastic strands; and
    a second adhesive pattern of elements on the second substrate and adhesively engaging a second portion of the one or more elastic strands.

5. The absorbent article of claim 4, wherein the first adhesive pattern of elements is the same as the second adhesive pattern of elements.

6. The absorbent article of claim 4, wherein the elements of the first adhesive pattern have a first size, wherein the elements of the second adhesive pattern have a second size, and wherein the first size is the same as the second size.

7. The absorbent article of claim 4, wherein the elements of the first adhesive pattern have a first shape, wherein the elements of the second adhesive pattern have a second shape, and wherein the first shape is the same as the second shape.

8. The absorbent article of claim 4, wherein the elements of the first adhesive pattern have a first size or shape, and wherein the elements of the second adhesive pattern have a second, different size or shape.

9. The absorbent article of claim 1, wherein a first pattern of densified regions in the first substrate is different than a second pattern of densified regions in the second substrate.

10. The absorbent article of claim 1, wherein one of the substrates has a first pattern of densified regions and a second pattern of densified regions formed therein, and wherein the first pattern of densified regions is different than the second pattern of densified regions.

11. The absorbent article of claim 1, wherein the continuous texture grid extends in a first direction and in a second, different direction, and wherein the plurality of discrete texture areas each form substantially the same polygonal shape.

12. The absorbent article of claim 1, wherein at least some of the plurality of discrete texture areas form a diamond-like shape.

13. The absorbent article of claim 1, wherein the second substrate within at least a portion of the first and second pluralities of rugosities is nested with the first substrate.

14. An absorbent article comprising:
a longitudinal axis;
a core;
a first substrate;
a second substrate;
one or more elastic strands disposed at least partially intermediate the first substrate and the second substrate, wherein the second substrate is attached to the first substrate and/or portions of one or more of the elastic strands, and wherein the elastic strands have an elastic strands spacing in the range of about 2 mm to about 4 mm, according to the Rugosity Length, Rugosity Frequency, Rugosity Amplitude, Elastic Element Spacing, and Texture Ratio Method described herein;
a pattern of discrete adhesive elements disposed on the first substrate;
a plurality of discrete texture areas each comprising a first portion of the substrates, a first portion of the one or more elastic strands, and one or more of the discrete adhesive elements, wherein at least some of the discrete texture areas comprise a first plurality of rugosities, and wherein the substrates are nested within the first plurality of rugosities; and
a continuous texture grid comprising a second portion of the substrates, a second portion of the one or more elastic strands, wherein the second portion of the substrates and the second portion of the one or more elastic strands within the continuous texture grid are free of the pattern of discrete adhesive elements, and wherein the continuous texture grid comprises a second plurality of rugosities.

15. The absorbent article of claim 14, wherein the continuous texture grid surrounds at least some of the plurality of discrete texture areas.

16. The absorbent article of claim 14, wherein the continuous texture grid is free of the discrete adhesive elements and comprises portions that are angled relative to the longitudinal axis.

17. The absorbent article of claim 14, wherein the first plurality of rugosities have a first frequency range and a first amplitude range in the first portion of the substrates, wherein the second plurality of rugosities have a second frequency range and a second amplitude range in the second portion of the substrates, wherein the first frequency range is different than the second frequency range, and wherein the first amplitude range is different than the second amplitude range.

18. The absorbent article of claim 14, wherein the one or more elastic strands are intermittently bonded to at least one of the substrates.

19. The absorbent article of claim 14, wherein the continuous texture grid forms a repeating diamond pattern in which the discrete texture areas are positioned.

20. An absorbent article comprising:
a chassis comprising:
a topsheet;
a backsheet; and
a core disposed at least partially intermediate the topsheet and the backsheet; and
a belt portion extending from the chassis, the belt portion comprising:
a first substrate;
a second substrate;
one or more elastic strands disposed at least partially intermediate the first substrate and the second substrate, wherein portions of the elastic strands are joined to the first substrate, wherein the second substrate is joined to the first substrate or to portions of the elastic strands, and wherein the elastic strands have an elastic strand spacing in the range of about 2 mm to about 4 mm, according to the Rugosity Length, Rugosity Frequency, Rugosity Amplitude, Elastic Element Spacing, and Texture Ratio Method described herein;
a pattern of discrete adhesive elements at least partially intermediate the first substrate and the second substrate;
a plurality of discrete texture areas each comprising a first plurality of rugosities formed in the first substrate, wherein at least some of the plurality of discrete texture areas form a polygonal shape, wherein the first plurality of the rugosities have a first frequency range, and wherein the first plurality of rugosities have a minimum amplitude of 1 mm; and
a continuous texture grid free of the pattern of the discrete adhesive elements and comprising a second plurality of rugosities formed in the first substrate, wherein the second plurality of the rugosities have a second, different frequency range, and wherein the second plurality of rugosities have a minimum amplitude of 1 mm;
wherein the first substrate is nested with the second substrate in the first plurality of rugosities or the second plurality of rugosities.

21. The absorbent article of claim 20, wherein the plurality of discrete texture areas are positioned within the continuous texture grid, and wherein the plurality of discrete texture areas correspond with the pattern of discrete adhesive elements.

* * * * *